US009404119B2

(12) United States Patent
De Block et al.

(10) Patent No.: US 9,404,119 B2
(45) Date of Patent: Aug. 2, 2016

(54) COTTON FIBERS HAVING POSITIVELY CHARGED OLIGOSACCHARIDES

(71) Applicant: Bayer CropScience N.V., Diegem (BE)

(72) Inventors: Marc De Block, Merelbeke (BE); Frank Meulewaeter, Merelbeke (BE); Rainhard Koch, Kleinmachnow (DE); Bernd Essigmann, Berlin (DE)

(73) Assignee: Bayer CropScience N.V., Diegem (BE)

( * ) Notice: Subject to any disclaimer, the term of this patent is extended or adjusted under 35 U.S.C. 154(b) by 143 days.

(21) Appl. No.: 13/942,204

(22) Filed: Jul. 15, 2013

(65) Prior Publication Data

US 2013/0312141 A1    Nov. 21, 2013

Related U.S. Application Data

(62) Division of application No. 13/187,378, filed on Jul. 20, 2011, now Pat. No. 8,507,755, which is a division of application No. 11/993,816, filed as application No. PCT/EP2006/005853 on Jun. 19, 2006, now Pat. No. 8,008,544.

(60) Provisional application No. 60/698,182, filed on Jul. 11, 2005.

(30) Foreign Application Priority Data

Jun. 24, 2005 (EP) ..................................... 05076488
Apr. 25, 2006 (EP) ..................................... 06008463

(51) Int. Cl.
*C12N 15/82* (2006.01)
*C12N 9/10* (2006.01)
*D02G 3/02* (2006.01)

(52) U.S. Cl.
CPC .......... *C12N 15/8246* (2013.01); *C12N 9/1051* (2013.01); *D02G 3/02* (2013.01); *Y10T 428/249921* (2015.04)

(58) Field of Classification Search
None
See application file for complete search history.

(56) References Cited

U.S. PATENT DOCUMENTS

| | | | |
|---|---|---|---|
| 5,004,863 A | 4/1991 | Umbeck |
| 5,729,933 A | 3/1998 | Strength |
| 6,166,294 A | 12/2000 | Kasukabe et al. |
| 6,259,003 B1 | 7/2001 | Fujisawa et al. |
| 6,483,013 B1 | 11/2002 | Reynaerts et al. |
| 8,008,544 B2 | 8/2011 | De Block et al. |
| 8,507,755 B2 | 8/2013 | De Block et al. |
| 2003/0106097 A1 | 6/2003 | Haigler et al. |
| 2003/0134120 A1 | 7/2003 | Kim et al. |
| 2003/0233675 A1 | 12/2003 | Cao et al. |
| 2006/0136136 A1 | 6/2006 | Karpusas |

FOREIGN PATENT DOCUMENTS

| | | | |
|---|---|---|---|
| EP | 0 433 509 | 6/1991 |
| WO | WO 92/15675 | 9/1992 |
| WO | WO 98/30698 | 7/1998 |
| WO | WO 99/01558 | 1/1999 |
| WO | WO 99/07830 | 2/1999 |
| WO | WO 99/29879 | 6/1999 |
| WO | WO 00/09729 | 2/2000 |
| WO | WO0009729 | * 2/2000 | ......... C12N 15/8246 |
| WO | WO 01/17333 | 3/2001 |
| WO | WO 02/10377 | 2/2002 |
| WO | WO 02/10413 | 2/2002 |
| WO | WO 2004/050708 | 6/2004 |
| WO | WO 2006/026754 | 3/2006 |

OTHER PUBLICATIONS

Benevenuti, et al. (2007) *Nature Protocols* 2(7): 1633-1651.
Cudney (1999) "Protein Crystallization and Dumb Luck," *The Rigakcu Journal* 16(1): 1-7.
Drenth (1999) "Principles of Protein X-Ray Crystallography," $2^{nd}$ Edition Chapter 1: 1-21.
DrugBank: Thyrotropin Alfa (BTD00020) [Jun. 27, 2005] downloaded from Internet on Aug. 18, 2006 (10 pages).
Barny, et al. (1996) Molecular Microbiology 19: 443-453.
Essl, et al. (1999) FEBS Letters 453: 169-173.
Geremia, et al. (1994) PNAS USA 91(7): 2669-2673.
Gomez and Chrispeels (1994) PNAS USA 91: 1829-1833.
Haigler, et al. (2000) Annual Meeting of the American Society of Plant Physiologists.
Joersbo, et al. (2001) Molecular Breeding 7(3): 211-219.
Kamst and Spaink (1999) Trends in Glycoscience and Glycotechnology 11: 187-199.
Kamst, et al. (1997) Journal of Bacteriology 179: 2103-2108.
Liu, et al. (2003) Carbohydrate Polymers 44: 233-238.
Munro, et al. (1991) EMBO Journal 10: 3577-3588.
Oda, et al. (2005) Plant Physiology 137(3): 1027-1036.
Pagny, et al. (2003) The Plant Journal 33: 189-203.
Park, et al. (2004) FEBS Letters 564(1-2): 183-187.
Saint-Jore, et al. (2002) The Plant Journal 29: 661-678.
Strasser, et al. (2004) Glycoconjugate Journal 21(5): 275-282.
Wojtaszek, et al. (1995) Plant Physiology 108(3): 1001-1012.
International Search Report for International Application No. PCT/EP2006/005853, mailed Feb. 16, 2007.
Written Opinion for International Application No. PCT/EP2006/005853, mailed Feb. 16, 2007.
Fan & Hendrickson (2005) Nature 433: 269-277.

(Continued)

*Primary Examiner* — Brent Page
(74) *Attorney, Agent, or Firm* — Arent Fox LLP

(57) ABSTRACT

Methods and means are provided for the modification of the reactivity of plant cell walls, particularly as they can be found in natural fibers of fiber producing plants by inclusion of positively charged oligosaccharides or polysaccharides into the cell wall. This can be conveniently achieved by expressing a chimeric gene encoding an N-acetylglucosamine transferase, particularly an N-acetylglucosamine transferase, capable of being targeted to the membranes of the Golgi apparatus in cells of a plant.

10 Claims, 11 Drawing Sheets

(56) References Cited

OTHER PUBLICATIONS

Guo, et al. (2005) Journal of Immunological Methods 303: 142-147.
Jeffreys, et al. (2002) Thyroid 12(12): 1051-1061.
Kaczur, et al. (2003) Molecular Genetics and Metabolism 78: 275-290.
Kajava, et al. (1995) Structure 3(9): 869-877.
Kundrot (2004) Cellular Molecular Life Science 61: 525-536.
International Search Report and Written Opinion for International Patent Application No. PCT/GB2007/003286, mailed Jan. 1, 2008.
McPherson (1990) *European Journal of Biochemistry* 189: 1-23.
Miguel, et al. (2004) *Thyroid* 14(12): 991-1011.
Sanders, et al. (2004) *Thyroid* 14(8): 560-570.

* cited by examiner

```
ROT_NODC_RHILP    MTMLDTTSTV AVSLYALLST AYKSMQAVYS LPTDVSLASH GLGGFDELPS
ROT_NODC_BRAJA    MDLLATTSAA AVSSYALLST IYKSVQALYA QPAINSSLDN LGQAEVVVPA
ROT_NODC_RHIS3    MDLLTTTSTV AVACYALLST VYKGMQAVYS LPPTVAPASE DLVGSDLWPS
ROT_NODC_RHISN    MDLLGTTGAV AISLYAALST AYKGMQAIYA LPTNTTAAST PVTGSGAPPS
ROT_NODC_RHILV    MTLLATTSIA AISLYAMLST VYKSAQVFHA RRTTISTTPA KDIETNPVPS
ROT_NODC_AZOCA    MSVVDVIGLL ATAAYVTLAS AYKVVQFIN. VSSVIDVAGL ESDALPLTPR
                  M--------- A-----Y--L- --YK---Q-- ---------- ---------P-

ROT_NODC_RHILP    VDVIVPSFNE DPRTLSECLA SIAGQEYGGR LQVYLVDDGS ENREALRLVH
ROT_NODC_BRAJA    VDVIVPCFNE NPNTLAECLE SIASQDYAGK MQVYVVDDGS ANRDVVAPVH
ROT_NODC_RHIS3    VDVIIPCYNE GPLTLSACLD SIANQEYAGK LRVYVVDDGS GNRDAVIPIH
ROT_NODC_RHISN    VDVIVPCYNE DPRALSACLA SIAKQDYAGE LRVYVVDDGS GNRNAIIPVH
ROT_NODC_RHILV    VDVIVPCFNE DPIVLSECLA SLAEQDYAGK LRIYVVDDGS KNRDAVVAQR
ROT_NODC_AZOCA    VDVIVPTFNE NSSTLLECVA SICAQDYRGP ITIVVVDDGS TNKTSFHAVC
                  VDVI-P--NE -----L-C-- S---Q-Y-G- -----VDDGS -N--------

ROT_NODC_RHILP    EAFARDPRFN ILLLPQNVGK RKAQDRCDQR SAGDMVLNVD SDTILASDVI
ROT_NODC_BRAJA    RIYASDPRFS FILLANNVGK RKAQIAAIRS SSGDLVLNVD SDTILAADVV
ROT_NODC_RHIS3    DNYAGDPRFD FILLPENVGK RKAQIAAIRR SSGDLVLNVD SDTTLASDVI
ROT_NODC_RHISN    DHYACDPRFR FILMPKNVGK RKAQIVAIRE SSGDLVLNVD SDTTIAPDVV
ROT_NODC_RHILV    AAYADDERFN FTILPKNVGK RKA.IAAITQ SSGDLILNVD SDTTIAPDVV
ROT_NODC_AZOCA    DKYASDERFI FVELDQNKGT A.AQMEAIRR TDGDLILNVD SDTVIDKDVV
                  ---A-D-R-- F------N-G ---A------ --GD--LNVD SDT----DV-

ROT_NODC_RHILP    RKLVPKNARV AVGR.MGQLT GPQPKRQLAD PFDDMEYWLA CNEERSQQAR
ROT_NODC_BRAJA    TKLVLKMHDP GIGAAMGQLI ASNRNQTWLT RLIDMEYWLA CNEERAAQAR
ROT_NODC_RHIS3    RKLARKMQDP AIGAAMGQLT ASNRSDTWLT RLIDMEYWLA CNEERAAQAR
ROT_NODC_RHISN    TKLALKMYSP AVGAAMGOLT ASNRSDTWLT RLIDMEYWLA CNEERAAQAR
ROT_NODC_RHILV    SKLAHKMRDP AVGAAMGQMK ASNQADTWLT RLIDMEYWLA CNEERAAQAR
ROT_NODC_AZOCA    TKLASSMRAP NVGGVMGQLV AKNRERSWLT RLIDMEYWLA CNEERIAQSR
                  -KL------- --G--MGQ-- ---------- ---DMEYWLA CNEER--Q-R

ROT_NODC_RHILP    FGCVMFCSGS CVMYRLVSA. SLLDQYDAQY FRKQR..FGE .IDIHLSHAE
ROT_NODC_BRAJA    FGAVMCCCGP CAMYRRSALA LLLDQYEAQF FRGKPSDFGE DRHLTILMLK
ROT_NODC_RHIS3    FGAVMCCCGP CAMYRRSSLL SLLDQYETQM FRGKPSDFGE DRHLTILMLE
ROT_NODC_RHISN    FGAVMCCCGP CAMYRRSALL LLLDKYETQL FRGRPSDFGE DRHLTILMLN
ROT_NODC_RHILV    FGAVMCCCGP CAMYRRSAML SLLDQYETQL YRGKPSDFGE DRHLTILMLS
ROT_NODC_AZOCA    FGSVMCCCGP CAMYRRSAIT PLLAEYEHQT FLGRPSNFGE DRHLTILMLK
                  FG-VM-C-G- C-MYR----- -LL-Y---Q- F------FGE ----------
```

FIGURE 1

```
ROT_NODC_RHILP    GSFRTEYRPS AHAATVVPNK LGPYLGQQLR WARSTFRTTL LGAP.LPNLN
ROT_NODC_BRAJA    AGFRTEYVPD AIAATVVPHS LRPYLRQQLR WARSTFRDTF LAWRLLPELD
ROT_NODC_RHIS3    AGFRTEYVPD AIAVTVVPDR LGPYLRQQLR WARSTFRDTL LALRLLPGLD
ROT_NODC_RHISN    AGFRTEYVPE AIAATVVPNS MGAYLRQQLR WARSTFRDTL LALRLLPGLD
ROT_NODC_RHILV    AGFRTEYVPS AIAATVVPDT MGVYLRQQLR WARSTFRDTL LALPVLPGLD
ROT_NODC_AZOCA    AGFRTGYVPS AVARTLVPDG .SPYLRQQLR WARSTYRDTA LALRIKKNLS
                  --FRT-Y-P- -A-A-T-VP- ---YL-QQLR WARST-R-T- L--------

ROT_NODC_RHILP    RFLMLDVVGQ NLGPLLLDHS VLTGLAQLAL TGTAPWLAAL MIVAMTIDRC
ROT_NODC_BRAJA    GYLTLDVIGQ NLGPLLLAIS SLAALAQLLI DGSIPWWTGL TIAAMTTVRC
ROT_NODC_RHIS3    RYLTLDVVGQ NLGPLLLALS VIAGIAQFAL TATLPWPTIL VIAAMTIIRC
ROT_NODC_RHISN    RYLTLDVIGQ NLGPLLLALS VLTGLAQLAL TATVPWSTIL MIASMTMVRC
ROT_NODC_RHILV    RYLTLDAIGQ NVGLLLIALS VLTGIGQFAL TATLPWTIL VIGSMTLVRC
ROT_NODC_AZOCA    KYITFFEICAQ NLGTALLLVM TMISLSLTTS GSQTPVIILG VVVGMSIIRC
                  ---------- N-G--LL--- ---------P ----M---RC

ROT_NODC_RHILP    SVVALRARQL RPLGFSLHTF INIFLLLPLK AYALCTLSNI AWLSSLLCWQ
ROT_NODC_BRAJA    CVAALRAREL RFIGFSLHTP INICLLLPLK AYALCTLSNS DWLSRKVTDM
ROT_NODC_RHIS3    TVTACRARQA RFIGFSLHTF INFLLLLPLK AYALCTLSNS DWLSRKTATL
ROT_NODC_RHISN    GVAAFRAREL RFLGFSLHTL LNVALLLPLK AYALCTLSNS DWLSRGSPAA
ROT_NODC_RHILV    SVAAYRAREL RFLGFALHTL VNIFLLIPLK AYALCTLSNS DWLSRGSVAI
ROT_NODC_AZOCA    CSVALIAKDF RFLYFIVHSA LNVLILTPLK LYALLTIRDS RWLSRESS..
                  ---------- RF-F---H-- -N---L-PLK -YAL-T---- -WLS------

ROT_NODC_RHILP    LESTSTADAR TT........ .ECSDMR TASKLSPPPS CQANDV....
ROT_NODC_BRAJA    PTEEGKQPVI LHPNAGRSPA GVGGRLLLFV RRRYRSLHRA WRRRRVFPVA
ROT_NODC_RHIS3    PNADKKQIIV ANPIAGVGTG SSGSAEAIRR TDLPRDSSKL VNADSVCSAE
ROT_NODC_RHISN    APNGVKDSPE PHC....... .......... .......... ..........
ROT_NODC_RHILV    APTVGQQGAT KMP....... .......... ........GR ATSEIAYSGE
ROT_NODC_AZOCA    .......... .......... .......... .......... ..........

ROT_NODC_RHILP    .......... .......... .......... ..........
ROT_NODC_BRAJA    IVRLSTNKWS ADDSGRKPSV IRARVGCRRP VAPRH
ROT_NODC_RHIS3    .......... .......... .......... .....
ROT_NODC_RHISN    .......... .......... .......... .....
ROT_NODC_RHILV    .......... .......... .......... .....
ROT_NODC_AZOCA    .......... .......... .......... .....
```

FIGURE 1 CONTINUED

```
ROT_NODC_BRAJA    MDLLATTSAA AVSSYALLST IYKSVQALYA QPAINSSLDN LGQAEVVVPA
ROT_NODC_RHIS3    MDLLTTTSTV AVACYALLST VYKGMQAVYS LPPTVAPASE DLVGSDLWPS
ROT_NODC_RHISN    MDLLGTTGAV AISLYAALST AYKGMQAIYA LPTNTTAAST PVTGSGAPPS
ROT_NODC_RHILV    MTLLATTSIA AISLYAMLST VYKSAQVFHA RRTTISTTPA KDIETNPVPS
ROT_NODC_AZOCA    MSVVDVIGLL ATAAYVTLAS AYKVVQFIN. VSSVTDVAGL ESDALPLTPR
                  M--------- A----Y--L-- --YK---Q-- ---------- -------P--

ROT_NODC_BRAJA    VDVIVPCFNE NPNTLAECLE SIASQDYAGK MQVYVVDDGS ANRDVVAPVH
ROT_NODC_RHIS3    VDVIIPCYNE GPLTLSACLD SIANQEYAGK LRVYVVDDGS GNRDAVIPIH
ROT_NODC_RHISN    VDVIVPCYNE DPRALSACLA SIAKQDYAGE LRVYVVDDGS GNRNAIIPVH
ROT_NODC_RHILV    VDVIVPCFNE DPIVLSECLA SLAEQDYAGK LRIYVVDDGS KNRDAVVAQR
ROT_NODC_AZOCA    VDVIVPTFNE NSSTLLECVA SICAQDYRGP ITIVVVDDGS TNKTSFHAVC
                  VDVI-P--NE -----L--C- S---Q-Y-G- ----VVDDGS -N--------

ROT_NODC_BRAJA    RIYASDPRFS FILLANNVGK RKAQIAAIRS SSGDLVLNVD SDTILAADVV
ROT_NODC_RHIS3    DNYAGDPRFD FILLPENVGK RKAQIAAIRR SSGDLVLNVD SDTTLASDVI
ROT_NODC_RHISN    DHYACDPRFR FILMPKNVGK RKAQIVAIRE SSGDLILNVD SDTTIAPDVV
ROT_NODC_RHILV    AAYADDERFN FTILPKNVGK RKA.IAAITQ SSGDLILNVD SDTTIAPDVV
ROT_NODC_AZOCA    DKYASDERFI FVELDQNKGT A.AQMEAIRR TDGDLILNVD SDTVIDKDVV
                  ---A-D-R-- F------N-G- ---A------ --GDL-LNVD SDT----DV-

ROT_NODC_BRAJA    TKLVLKMHDP GIGAAMGQLI ASNRNQTWLT RLIDMEYWLA CNEERAAQAR
ROT_NODC_RHIS3    RKLARKMQDP AIGAAMGQLT ASNRSDTWLT RLIDMEYWLA CNEERAAQAR
ROT_NODC_RHISN    TKLALKMYSP AVGAAMGQLT ASNRSDTWLT RLIDMEYWLA CNEERAAQAR
ROT_NODC_RHILV    SKLAHKMRDP AVGAAMGQMK ASNQADTWLT RLIDMEYWLA CNEERAAQAR
ROT_NODC_AZOCA    TKLASSMRAP NVGGVMGQLV AKNRERSWLT RLIDMEYWLA CNEERIAQSR
                  -KL----M--P --G--MGQ-- -A--N----WLT RLIDMEYWLA CNEER--Q-R

ROT_NODC_BRAJA    FGAVMCCCGP CAMYRRSALA LLLDQYEAQF FRGKPSDFGE DRHLTILMLK
ROT_NODC_RHIS3    FGAVMCCCGP CAMYRRSSLL SLLDQYETQM FRGKPSDFGE DRHLTILMLE
ROT_NODC_RHISN    FGAVMCCCGP CAMYRRSALL LLLDKYETQL FRGRPSDFGE DRHLTILMLN
ROT_NODC_RHILV    FGAVMCCCGP CAMYRRSAML SLLDQYETQL YRGKPSDFGE DRHLTILMLS
ROT_NODC_AZOCA    FGSVMCCCGP CAMYRRSAIT PLLAEYEHQT FLGRPSNFGE DRHLTILMLK
                  FG-VMCCCGP CAMYRRS--- -LL---YE-Q- F-G-PS-FGE DRHLTILML-
```

FIGURE 2

```
ROT_NODC_BRAJA      AGFRTEYVPD AIAATVVPHS LRPYLRQQLR WARSTFRDTF LAWRLLPELD
ROT_NODC_RHIS3      AGFRTEYVPD AIAVTVVPDR LGPYLRQQLR WARSTFRDTL LALRLLPGLD
ROT_NODC_RHISN      AGFRTEYVPE AIAATVVPNS MGAYLRQQLR WARSTFRDTL LALRLLPGLD
ROT_NODC_RHILV      AGFRTEYVPS AIAATVVPDT MGVYLRQQLR WARSTFRDTL LALPVLPGLD
ROT_NODC_AZOCA      AGFRTGYVPS AVARTLVPDG .SPYLRQQLR WARSTYRDTA LALRIKKNLS
                    AGFRT-YVP- A-A-T-VP-- ---YLRQQLR WARST-RDT- LA--------

ROT_NODC_BRAJA      GYLTLDVIGQ NLGPLLLAIS SLAALAQLLI DGSIPWWTGL TIAAMTTVRC
ROT_NODC_RHIS3      RYLTLDVVGQ NLGPLLLALS VIAGIAQFAL TATLPWPTIL VIAAMTIIRC
ROT_NODC_RHISN      RYLTLDVIGQ NLGPLLLALS VLTGLAQLAL TATVPWSTIL MIASMTMVRC
ROT_NODC_RHILV      RYLTLDAIGQ NVGLLLLALS VLTGIGQFAL TATLPWWTIL VIGSMTLVRC
ROT_NODC_AZOCA      KYITFEICAQ NLGTALLLVM TMISLSLTTS GSQTPVIILG VVVGMSIIRC
                    -Y-T-----Q N-G--LL--- ---------- ----P----- ----M---RC

ROT_NODC_BRAJA      CVAALRAREL RFIGFSLHTP INICLLLPLK AYALCTLSNS DWLSRKVTDM
ROT_NODC_RHIS3      TVTACRARQA RFIGFSLHTF INIFLLLPLK AYALCTLSNS DWLSRKTATL
ROT_NODC_RHISN      GVAAFRAREL RFLGFSLHTL LNVALLLPLK AYALCTLSNS DWLSRGSPAA
ROT_NODC_RHILV      SVAAYRAREL RFLGFALHTL VNIFLLIPLK AYALCTLSNS DWLSRGSVAI
ROT_NODC_AZOCA      CSVALIAKDF RFLYFIVHSA LNVLILTPLK LYALLTIRDS RWLSRESS..
                    ---------- RF-FF--H-- -N---L-PLK -YAL-T---S -WLSR-----

ROT_NODC_BRAJA      PTEEGKQPVI LHPNAGRSPA GVGGRLLLFV RRRYRSLHRA WRRRRVFPVA
ROT_NODC_RHIS3      PNADKKQIIV ANPIAGVGTG SSGSAEAIRR TDLPRDSSKL VNADSVCSAE
ROT_NODC_RHISN      APNGVKDSPE PHC....... .......... .......... ..........
ROT_NODC_RHILV      APTVGQQGAT KMP....... .......... ........GR ATSEIAYSGE
ROT_NODC_AZOCA      .......... .......... .......... .......... ..........
                    --------------------------------------------------

ROT_NODC_BRAJA      IVRLSTNKWS ADDSGRKPSV IRARVGCRRP VAPRH
ROT_NODC_RHIS3      .......... .......... .......... .....
ROT_NODC_RHISN      .......... .......... .......... .....
ROT_NODC_RHILV      .......... .......... .......... .....
ROT_NODC_AZOCA      .......... .......... .......... .....
                    ---------- ---------- ---------- -----
```

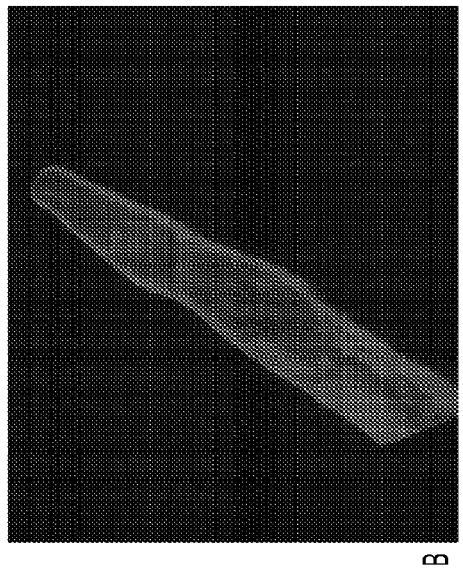
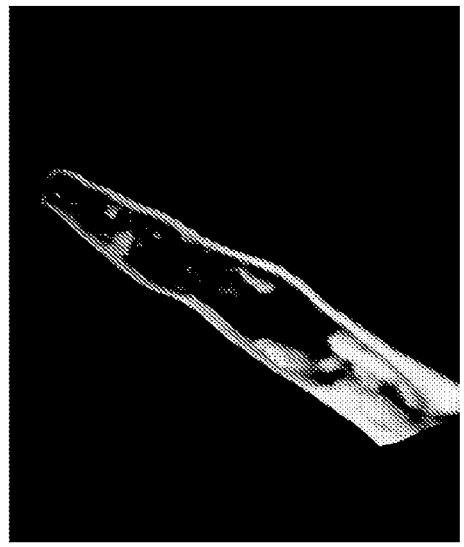
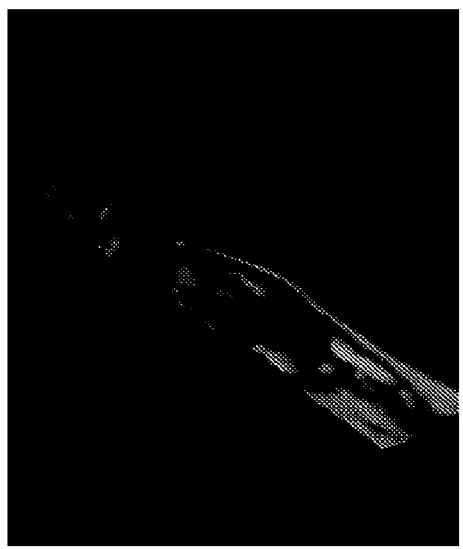
FIG. 4

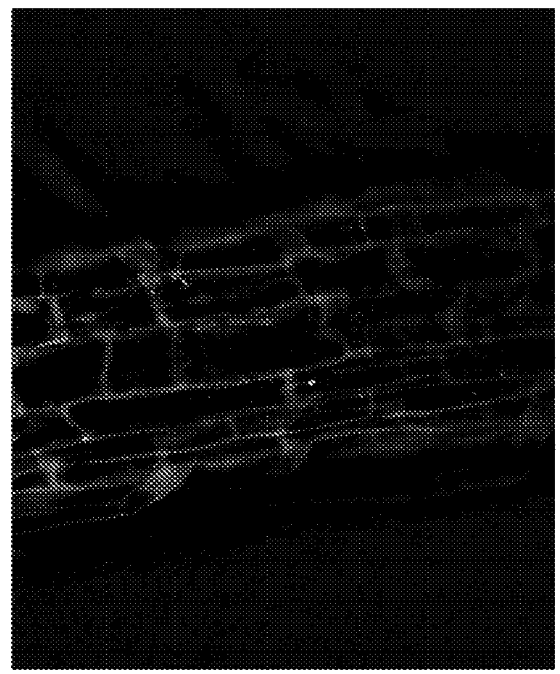
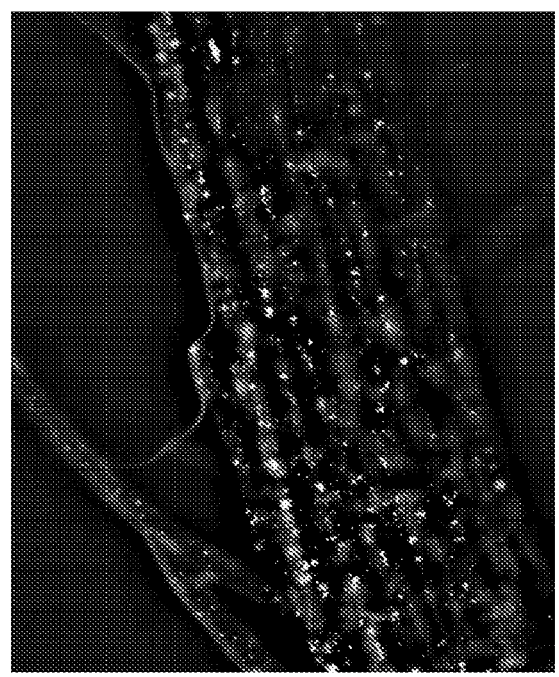
FIG. 5

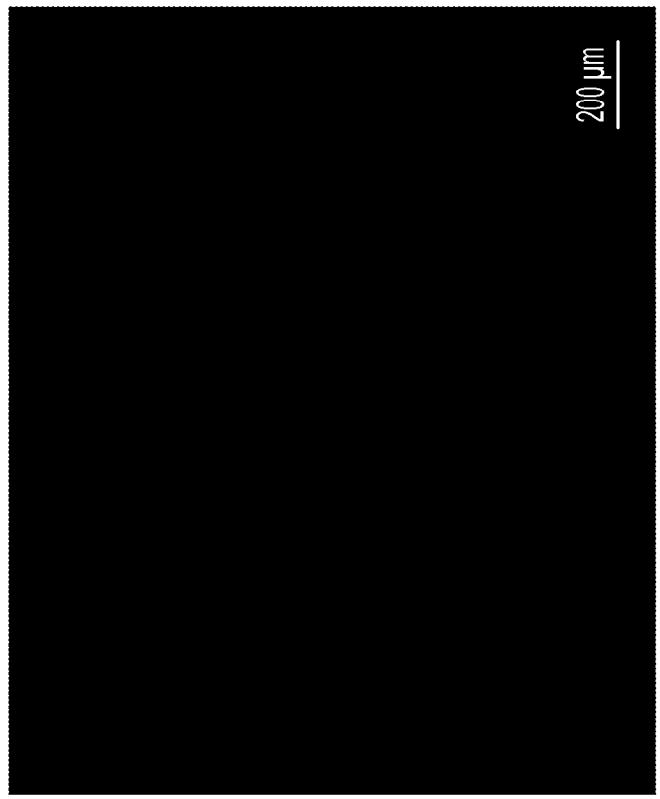
FIG. 8

COTTON FIBERS HAVING POSITIVELY CHARGED OLIGOSACCHARIDES

CROSS-REFERENCE TO RELATED APPLICATIONS

This application is a divisional patent application of U.S. patent application Ser. No. 13/187,378, filed Jul. 20, 2011, now U.S. Pat. No. 8,507,755, which is divisional patent application of U.S. patent application Ser. No. 11/993,816, filed Dec. 21, 2007, now U.S. Pat. No. 8,008,544, which is the U.S. National Stage filing of International patent application No. PCT/EP 2006/005853, filed Jun. 19, 2006, which claims priority to EP 05076488.5, filed Jun. 24, 2005; U.S. Provisional Patent Application No. 60/698,182, filed Jul. 11, 2005; and EP 06008463.9, filed Apr. 25, 2006, the disclosures of each of which are hereby incorporated by reference.

The present invention relates to the modification of the reactivity of plant cell walls, including secondary plant cell walls, particularly as they can be found in natural fibers of fiber producing plants. In particular, the present invention is related to cotton fibers with altered reactivity. The modified reactivity could be applied in methods for dyeing cell wall containing plant derived material such as natural fibers, using fiber-reactive dyes, to improve e.g. colorfastness, or to decrease the volumes of waste-water used during the dyeing process. The modified reactivity could also be applied to improve the reactivity of the natural fibers with reactants such as flame retardants, water, oil and soil repellents, anticrease agents, softeners, antistatic agents, fluorescent whitening agents etc.

BACKGROUND ART

Natural fibers, including cellulose containing natural fibers from plants, such as cotton and linen, have been used by mankind for more than 5000 years. Natural cellulose containing fibers, however, do not possess the chemical versatility of synthetic fibers, due to the relative inert nature of the cellulose consisting of β-1-4 linked glucose monomers.

This relative inert nature is e.g. apparent during the dyeing process of cotton fibers and fabrics. Generally two types of dyes are used to color cotton: direct dyes and fiber-reactive dyes, which are both anionic molecules. Cotton itself develops an anionic charge in water, so that without special treatment, the uptake of dye by the fiber or fabric is quite elaborate.

Direct dyes create a relatively weak hydrogen bond with the cellulose polymer forming a semi-permanent attachment. Direct dyes are easier to use and less expensive than fiber-reactive dyes, but do not withstand well washing. Fiber-reactive dyes are molecules that combine chromophores with a reactive group that forms strong covalent bonds with the fiber via reaction with hydroxyl groups. The covalent bonds provide a good resistance of the dyed fiber against laundring. Colorfastness can be improved using cationic fixatives.

During the dyeing process, large amounts of electrolytes are needed to shield the anionic dyes from the anionic fiber charges. Unreacted dyes (up to 40%) need to be removed by a washing step known as scouring, generating large volumes of wastewater, also containing the above mentioned electrolytes.

Providing the cellulose fiber with a positive electric charge, e.g. by incorporation of positively charged chemical compounds, could therefore improve the dyeability of natural cellulose fibers, as well as improve any chemical reaction of the modified cellulose fiber with negatively charged chemical compounds. It would also make the use of acidic dyes possible.

Several publications have described the incorporation into or coating of chitosan oligomers into cellulose fibers to make chitosan/cellulose blends, yarns or fabrics. Chitosan is a positively charged polymer of glucosamine, which can be obtained by deacetylation of chitin, e.g. by alkalic treatments. Chitin itself is a polymer of β-1-4 linked N-acetylglucosamine (GlcNAc).

US patent application US2003/0134120 describes the coating of natural fibers with chitosan.

Liu et al. (*Carbohydrate Polymers* 44 (2003) 233-238) describe a method for coating cotton fibers with chitosan, by oxidation of the cotton thread with potassium periodate at 60° C. in water and subsequent treatment with a solution of chitosan in aqueous acetic acid. With the chitosan coating, the cotton fiber surface became physiologically and biologically active. Since the chemical reactivity of the amino group is greater than the hydroxyl group of cellulose monomers, the fiber has more potential for further chemical modification. Moreover, the smooth surface of the cotton fiber became coarse, suggesting a greater potential for drug absorption and controlled release thereof.

Based on the physiological function of chitosan in inhibiting e.g. dermatophytes, many functional clothes, fabrics and fibers employ cellulose-chitosan blend fibers, cellulose fiber-chitosan conjugates and fabrics coated with chitosan-containing resins.

WO 00/09729 describe the expression of chitin synthase and chitin deacetylase genes in plants to alter the cell wall for industrial uses and improved disease resistance. Specifically cited uses are: to provide a single plant source of cellulose, chitin and chitosan, to increase tensile strength and to increase brittle snap. Specifically suggested chitin synthase genes are derived from fungal organisms. No experimental data are provided on the production of chitin or chitosan in plants, nor on the incorporation thereof in plant cell walls.

The prior art thus remains deficient in providing methods for obtaining plants from which plant cell walls, particularly secondary cell walls, such as natural fibers, can be isolated containing positively charged chemical groups and/or chemical groups which are more reactive than hydroxyl groups of cellulose. The prior art remains also deficient in providing fibers which can be directly harvested from plants and which contain positively charged chemical groups and/or group which are more reactive than hydroxyl groups of cellulose, which can be used directly without the need for further chemical treatment to introduce such chemical groups. These and other problems are solved as described hereinafter in the different embodiments, examples and claims.

SUMMARY OF THE INVENTION

Briefly, in one embodiment, the invention provides a method for increasing the amount of positively charged oligosaccharides or polysaccharides in the cell wall, particularly the secondary cell wall of a plant cell, comprising introducing a chimeric gene into the plant cell, whereby the chimeric gene comprises a plant-expressible promoter operably linked to a DNA region coding for an N-acetylglucosamine transferase, preferably wherein the N-acetylglucosamine transferase is targeted to the membranes of the Golgi-apparatus; and a transcription termination and polyadenylation region. In a particular embodiment, the plant is cotton, and the positively charged oligosaccharides or polysaccharides are incorporated in the secondary cell walls which make up the cotton fiber.

In another embodiment of the invention, a method is provided for increasing the amount of positively charged oligosaccharides or polysaccharides in the cell wall, particularly the secondary cell wall of a plant cell comprising introducing a chimeric gene into the plant cell, the chimeric gene comprising a plant-expressible promoter operably linked to a DNA region coding for an N-acetylglucosamine transferase of the NODC type; and a transcription termination and polyadenylation region. Again, in a specific embodiment, the plant is cotton, and the positively charged oligosaccharides or polysaccharides are incorporated in the secondary cell walls which make up the cotton fiber.

In yet another embodiment of the invention, a method is provided for increasing the amount of positively charged oligosaccharides or polysaccharides in the cell wall, particularly the secondary cell wall of a plant cell, the method comprising i. introducing a chimeric gene into the plant cell, said chimeric gene comprising the following operably linked DNA fragments:
1. a plant-expressible promoter;
2. a DNA region coding for chitin synthase; and
3. a transcription termination and polyadenylation region.

ii. applying to the transgenic plant cell an effective amount of N-acetylglucosamine, glucosamine-6-phosphate, N-acetylglucosamine-6-phosphate, N-acetylglucosamine-1-phosphate or UDP-N-acetylglucosamine.

The invention also provides plant cell walls, comprising an increased amount of polysaccharides or oligosaccharides, particularly positively charged oligosaccharides, such as oligo-N acetylglucosamines or oligo-glucosamines, preferably oligomers of N-acetylglucosamine or glucosamine with a polymerization degree between 3 and 10, particularly between 3 and 5. Such plant cell walls are obtainable by the methods of the invention. These plant cell walls may be subjected to further chemical modification.

In a specific embodiment, the invention provides cotton fibers comprising an increased amount of the positively charged oligosaccharides mentioned herein, and yarns, textiles which comprise such cotton fibers. The cotton fibers may be used as such or may have been subjected to further chemical modification, including dying. These cotton fibers can be recognized e.g. through their increased binding of anionic dyes, including congo red, through their increased binding of wheat germ agglutinin or through their increased reactivity with amine-reactive dyes when compared to cotton fibers obtained from cotton plants of a an isogenic line which does not contain a chimeric N-acetylglucosamine transferase gene as described herein. The presence and/or the amount of oligosaccharides in the cotton fibers can also be determined directly through e.g. high performance thin layer chromatography (HPTLC).

In another embodiment, the invention is directed towards the use of a DNA region coding for an N-acetylglucosamine transferase capable of being targeted to the Golgi apparatus of a plant cell to increase the amount of positively charged oligasccharides in the cell wall of a plant cell or to increase the reactivity of plant cell walls for chemical modifications of such plant cell walls.

The invention also provides chimeric genes comprising the following operably linked DNA regions: a plant-expressible promoter; a DNA region coding for an N-acetylglucosamine transferase, said N-acetylglucosamine transferase when expressed in a plant cell, being targeted to the Golgi apparatus of said plant cell; and a transcription termination and polyadenylation region. The N-acetylglucosamine transferase may be an N-acetylglucosamine transferase of the NODC type or could also be a chitin synthase, particularly a chitin synthase which has been operably linked to a Golgi retention signal.

BRIEF DESCRIPTION OF THE FIGURES

FIG. 1: Alignment of the amino acid sequence of different NODC proteins. Amino acid residues conserved in all proteins are indicated in bold. ROT_NODC_RHILP: NODC protein from *Rhizobium leguminosarum* (biovar *phaseoli*); ROT_NODC_BRAJA: NODC protein from *Bradyrhizobium japonicum* (SEQ ID No.); ROT_NODC_RHIS3 NODC protein from *Rhizobium* sp. (strain N33); ROT_NODC_RHISN: NODC protein from *Rhizobium* sp; ROTNODCRHILV: NODC protein from *Rhizobium leguminosarum* (biovar *viciae*) and ROTNODC_AZOCA: NODC protein from *Azorhizobium caulinodans*.

FIG. 2: Alignment of the amino acid sequence of different NODC proteins. Amino acid residues conserved in all proteins are indicated in bold. ROT_NODC_BRAJA: NODC protein from *Bradyrhizobium japonicum* (SEQ ID No.); ROT_NODC_RHIS3 NODC protein from *Rhizobium* sp. (strain N33); ROT_NODC_RHISN: NODC protein from *Rhizobium* sp; ROT_NODC_RHILV: NODC protein from *Rhizobium leguminosarum* (biovar *viciae*) and ROT_NODC_AZOCA: NODC protein from *Azorhizobium caulinodans*

Panel A. Optical section of a root hair cell stained with Calcofluor; B: optical section of a root hair cell immunohistochemically stained for the presence of N-acetylglucosamine; C: superposition of the optical sections of panel A and panel B.

FIG. 4: Photographs of fluorescent microscopy performed on root hair cells from hairy roots containing the 35S::NODC-EGFP chimeric gene.

Panel A. superposition of the optical sections of panels B, C and D. B: Optical section of a root hair cell stained with Calcofluor; C: optical section of a root hair cell stained to visualize the Golgi apparatus; D: optical section of a root hair cell visualizing the fluorescence by EGFP.

FIG. 5: Photographs of fluorescent microscopy performed on root hair cells from hairy roots containing the 35S::chitin synthase chimeric gene.

Panel A: Optical section of a hairy root cultured in the presence of 50 mM N-acetylglucosamine, stained for the presence of N-acetylglucosamine; Panel B: Optical section of a hairy root cultured in the presence of no extra N-acetylglucosamine, stained for the presence of N-acetylglucosamine in the cell wall.

Figure 6:
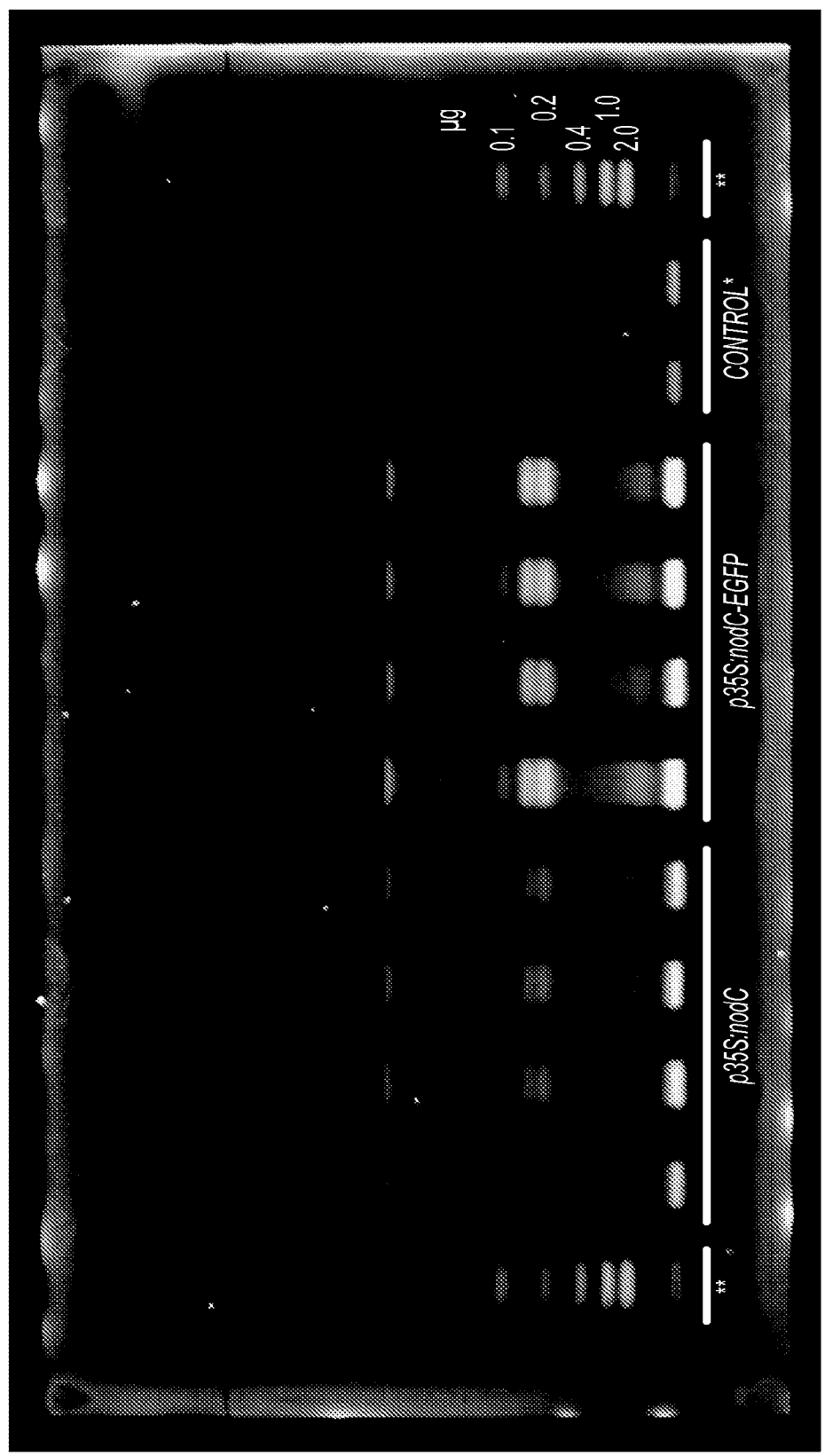

FIG. 6: High performance thin layer chromatogram of chito-oligomers from cell wall material isolated from *Arabidopsis* hairy roots.

The samples of the two outer lanes (1, 12) are standard solutions of N-acetylglucosamine, chitobiose, chitotriose, chitotetraose and chitopentaose. Lanes 2 to 5: cell wall material extracted from hairy root cultures initiated by *Agrobacterium rhizogenes* with a chimeric gene comprising a CaMV35S promoter linked to a nodC encoding region; lanes 6 to 9: cell wall material extracted from hairy root cultures initiated by *Agrobacterium rhizogenes* with a chimeric gene comprising a CaMV35S promoter linked to a nodC encoding region fused to eGFP; lanes 10 and 11, cell wall material extracted from hairy root cultures initiated by *Agrobacterium rhizogenes* with a chimeric gene comprising a CaMV35S promoter linked to a phosphinotricin acetyltransferase encoding region. TLC was performed in acetonitrile (76): water (24): 0.5% boric acid (10)

Figure 7:
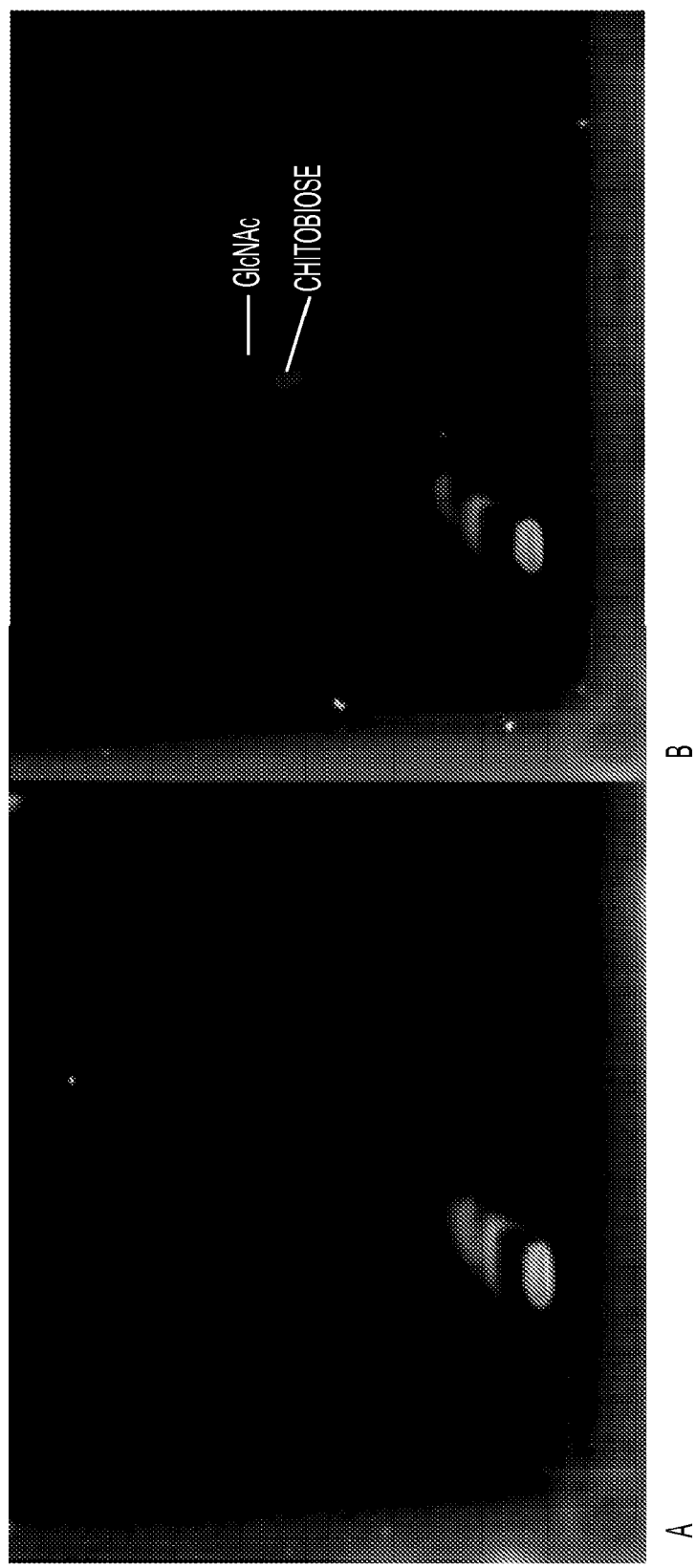

FIG. 7: Two dimensional HPTLC on cell wall material isolated from *Arabidopsis* hairy roots which has been subjected to chitinase digestion.

Control cell wall material (left panel) was extracted from hairy root cultures initiated by *Agrobacterium rhizogenes* with a chimeric gene comprising a CaMV35S promoter linked to a phosphinotricin acetyltransferase encoding region; experimental cell wall material (right panel) was extracted from hairy root cultures initiated by *Agrobacterium rhizogenes* with a chimeric gene comprising a CaMV35S promoter linked to a nodC encoding region fused to eGFP. Monomer saccharides (N-acetylglucosamine) and dimer chito-saccharides (chitobiose) can be detected in the experimental material, but not in the control material. TLC was performed in acetonitrile (76): water (24): 0.5% boric acid (10)

FIG. 8: HPTLC of cell wall material isolated from transgenic *Arabidopsis* plants.

Lane 1: standard solution chito-oligosaccharides; Lane 2: 0.1 glucosamine; lanes 3 and 4: 4 µl and 8 µl respectively of cell wall material isolated from control *Arabidopsis* shoots; lanes 5 and 6: 4 µl and 8 µl respectively of cell wall material isolated from transgenic *Arabidopsis* shoots comprising a CaMV35S::nodC chimeric gene; lanes 7 and 8: 4 µl and 8 µl respectively of cell wall material isolated from transgenic *Arabidopsis* shoots comprising a CaMV35S::nodC-eGFP chimeric gene. The dotted line indicates the increased amount of chito-triose particularly in lander 5 and 6.

Figure 9:
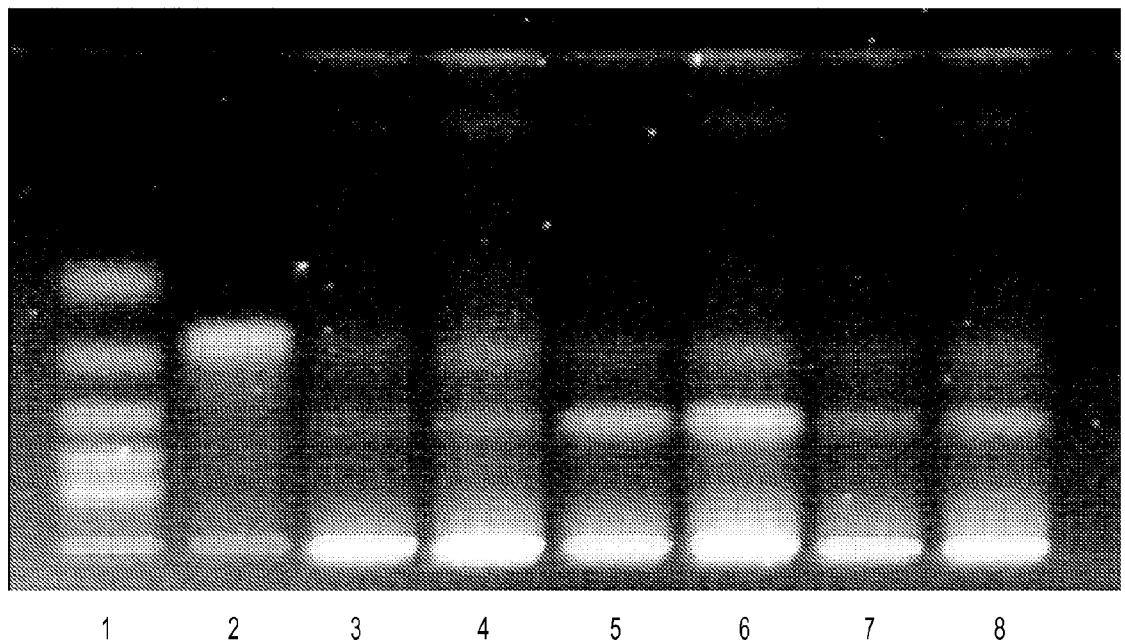

FIG. 9: Fluorescence microscopy of cotton fibers reacted with wheat-germ agglutinin (WGA) conjugated to Alexa fluor 555.

Left panel: cotton fibers from transgenic cotton plants containing, a CaMV35S::NodC gene. Right panel: cotton fibers from control cotton plants. Under UV-light, a bright fluorescence can be observed in the fibers from the transgenic cotton plants, indicating the presence of chito-oligomers in these fibers.

DETAILED DESCRIPTION OF DIFFERENT EMBODIMENTS OF THE INVENTIONS

The current invention is based on the finding that expression of N-acetylglucosamine transferase of the NODC type in plant cells leads to incorporation of N-acetylglucosamine oligomers into plant cell walls. The GlcNAc oligomers were unexpectedly associated very closely with the cell wall and were not dissolved from that cell wall by various treatments. Surprisingly, the synthesis of the GlcNAc oligomers did not require the external addition of GlcNAc to the growth medium, as was observed with other chitin synthases. Furthermore and equally surprising, the NODC protein was also closely associated with the membranes of the Golgi apparatus in addition to the association with the cell membrane as expected. When the N-acetylglucosamine transferase of the NODC type was expressed in cotton plants, the GlcNAc oligomers were incorporated into the cotton fibers, leading to more reactive cotton fibers.

Thus, in a first embodiment of the invention, a method is provided for increasing the amount of positively charged oligosaccharides in the cell wall, particularly the secondary cell wall of a plant cell, wherein the method comprises the step of introducing a chimeric gene into the plant cell, and the chimeric gene comprising the following operably linked DNA fragments:
   a plant-expressible promoter
   a DNA region coding for an N-acetylglucosamine transferase, wherein the N-acetylglucosamine transferase is of the NODC type; and
   a transcription termination and polyadenylation region.

Nodulation C protein ("NODC protein") and its encoding gene are involved in the synthesis of the lipochitooligosaccharide signals or acetylated chitooligomers (Nod factors) which lead to the nodule formation typical of the symbiosis between Rhizobiaceae and leguminous plants.

The most crucial nod gene products required for the synthesis of these lipo-chitooligosaccharides are NODA, NODB and NODC. In the absence of other nod gene products they can form a core signal consisting of oligomers of four or five N-acetylglucosamine residues carrying an N-linked acyl group. The function of each of the three proteins in the synthesis of nodulation factors is well known: NODC is an N-acetylglucosaminyl transferase which produces the chito-oligosacharide chain; the N-acetyl group from the non-reducing N-acetylglucosamine residue of the chito-oligosaccharide chain is removed by NODB, which acts as a chitin oligosaccharide deacetylase; NODA is involved in the attachment of the acyl chain to the free amino group generated by the action of NODB. Other Nod factors, encoded by other nod genes, provide for any of the decorating chemical groups discriminating the different nodulation factors. For the purposes of the present invention, only the NODC proteins and encoding genes are of relevance.

NODC protein is a well characterized protein (for a review see Kamst and Spaink, 1999, *Trends in Glycoscience and Glycotechnology*, 11, pp 187-199). It belongs to a family of (β-polysaccharide synthase proteins that are involved in the synthesis of linear polysaccharides containing β-linked monosaccharide residues. The enzymes that are structurally most closely related to NODC are transferases involved in the synthesis of chitin (β-1-4 linked N-acetylglucosamines); cellulose (the polymer of (β-1-4 linked glucose residues); hyaluronic acid (a co-polymer of N-acetylglucosamine and glucuronic acid) and chitin oligosaccharides produced during early development of zebrafish embryos. Six short regions conserved between these proteins can be recognized. For NODC proteins, these short sequences corresponds to:
   1) a K residue at position 23 of SEQ ID No 1 (NODC from *Azorhizobium caulinodans*)
   2) the sequence DDG at position 86-88 of SEQ ID No 1
   3) the sequence VDSDT at position 137-141 of SEQ ID No 1
   4) the sequence GPCAMYR at position 207-213 of SEQ ID No 1
   5) the sequence GEDRHL at position 237-242 of SEQ ID No 1; and
   6) the sequence QQLRW at position 274-278 of SEQ ID No 1

However, it is important to realize that some NODC proteins or variants thereof may exist wherein one or more of the above mentioned consensus sequences are not absolutely conserved.

NODC proteins are also frequently characterized by hydrophobic stretches of amino acid residues representing transmembrane domains (Barney et al. 1996, *Molecular Microbiology* 19, pp 443-453). The N-terminal hydrophobic domain spans the bacterial membrane in a $N_{out}$-$C_{in}$ orientation, with the adjacent large hydrophilic domain being exposed to the bacterial cytoplasm. This orientation appears to be dependent upon the presence of the hydrophobic region(s) near the C-terminus, potentially containing three membrane spans, such that the C-terminus of NODC is normally located in the bacterial periplasm.

The large hydrophilic loop of NODC also has other structural similarity to similar regions in the other β-glucosyl transferases. This region has been proposed to be made up of an A domain (which extends from about residue 45 to 140 in the sequence of SEQ ID No 4) consisting of alternating β-sheets and α-helices, and a B-domain (corresponding to residues 215-280 of SEQ ID No 4) thought to be responsible for the processivity of NODC. In the A-domain, two aspartate residues are conserved (residues 88 and 139 of SEQ ID No. 4); in the B-domain one aspartate residue and the motif QXXRW (residue 240 and 276-280 of SEQ ID No 4) are also conserved and thought to be crucial for catalytic activity.

When different NODC proteins are compared among themselves, amino acid sequences which are more conserved are revealed. FIG. 1 represents an alignment of different NODC proteins from SEQ ID No 1, 2, 8, 4, 7, 5 and indicates a number of conserved residues between the different NODC proteins including (in order):

```
the sequence PXVDVIXPXXNE the sequence VDDGSXN the sequence GDXXLDVDSDTXXXXDV the sequence GXXMGQ the sequence DMEYWLACNEERXXQXRFGXVMXCXGXCXMYR the sequence FRTXYXPXAXAXTXVP the sequence YLXQQLRWARSTXRXTXL the sequence QNXGXXLL the sequence RFXFXXXHXXXNXXXLXPLKXYALXT
```

FIG. 2 represents an alignment of a subset of different NODC proteins, showing even more conserved residues such as:

```
the sequence
WLTRLIDMEYWLACNEERXXQXRFGXVMCCCGPCAMYRRS the sequence
LLXXYEXQXFXGXPSXFGEDRHLTILMLXAGFRTXYVPXAXAXTXVP the sequence
YLRQQLRWARSTXRDTXLA
```

The length of the oligosaccharide backbone in lipo-chitin oligosaccharides produced by different Rhizobiaceae varies between two and six residues. It has been shown that the nodulation protein NODC is an important determinant of the chitin oligosaccharide chain length in the synthesis of the chito-oligosaccharide chain (Kamst et al., 1997, *Journal of Bacteriology* 179, p 2103-2108).

Coding regions coding for an N-acetylglucosamine transferase of the NODC type may be obtained directly from bacteria belonging to the genera *Rhizobium, Azorhizobium, Bradyrhizobium, Mesorhizobium, Ralstonia, Cupriavidus, Streptomyces, Burkholderia* or *Sinorhizobium*. However, it will be immediately clear that such coding regions may also be made synthetically, even with a codon usage adapted to the plant, particularly the fiber producing plant into which the chimeric gene overexpresing the NODC type protein is introduced.

Different sequences for NODC proteins are available from databases such as the protein sequences identified by the following accession numbers: CAA67139, CAA608779, CAA51774, CAA51773, CAA25811, CAA25810, CAA25814, CAA68619, CAA2350, CAD31533, CAC05896, CAH04369, CAB56055, NP_629203, P26024, P17862, BAB524500, AAX30050, AAX30049, E38180, JQ0396, ZZZRC4, ZZZRCL, A95321, C23766, C26813, NP_659761, NP_443883, NP_106714, NP_768667, NP 435719, BAC47292, AAU11365, AAU11364, AAU11363, AAU11362, AAU11361, AAU11360, AAU11359, AAU11358, AAU11357, AAU11356, AAU11355, AAU11354, AAU11353, AAU11352, AAU11351, AAU11350, AAU114349, AAU11348, AAU11347, AAU11346, AAU11345, AAU11344, AAU11343, AAU11342, AAU11341, AAU11340, AAU11339, AAU11338, AAK65131, AAS91748, P04679_2, P04679_1, P04679, P72334, Q53513, P50357, P04678, P50536, P53417, Q07755, P04341, P04340, P24151, P04677, CAD90588, CAD90587, CAD90586, CAD90585, CAD90584, CAD90583, CAD90257, CAD43933, AAM54775, AAN62903, S34305, S09522, S07304, AAL88670, CAD29957, CAD29956, CAD29955, CAD29954, CAD29953, CAD 29952, CAD29951, CAD29950, CAD29949, CAC42489, AAK53549, AAK53548, AAK50872, AAK39967, AAK39966, AAK39965, AAK39964, AAK39963, AAK39962, AAK39961, AAK39960, AAK39959, AAK39958, AAK39957, AAK39956, AAG44125, AAK00157, AAG60998, AAB71694, AAB16897, AAV80567, AAB95329, BAA24092, BAA06089, BAA06086, BAA06085, BAA06083, BAA06090, BAA06082, BAA06087, BAA06088, BAA06084, AAB91695, AAB51164, AAB47353, AAB34509, AAB24745, 1615305E, 1615305D, 165305C, CAA26311, CAA26310, CAA3731, AAA63602 or 26226 (incorporated herein by reference).

Other entries in the UNIPROT databases referring to full length NODC proteins are summarized in Table 1. All mentioned amino acid sequences referenced by the accession number are herein incorporated by reference.

TABLE 1

| full length NODC proteins | | | |
|---|---|---|---|
| UniProt/UniParc ID | UniProt Accessions | Species Name | Length |
| NODC_BRAJA | P26024 | *Bradyrhizobium japonicum* | 485 |
| NODC_AZOCA | Q07755 | *Azorhizobium caulinodans* | 395 |
| Q6PTX8_9RHIZ | Q6PTX8 | *Rhizobium* sp. SIN-1 | 408 |
| Q70YC2_9BURK | Q70YC2 | *Cupriavidus taiwanensis* | 450 |
| Q6EX51_SINSB | Q6EX51 | *Sinorhizobium* sp. | 452 |
| NODC_RHIS3 | P72334 | *Rhizobium* sp. | 450 |
| NODC_RHILP | P24151 | *Rhizobium leguminosarum* | 428 |
| Q8GNH5_RHIME | Q8GNH5 | *Rhizobium meliloti* | 421 |
| Q53254_RHITR | Q53254 | *Rhizobium tropici* | 452 |
| Q9AQ23_BRASW | Q9AQ23 | *Bradyrhizobium* sp. | 452 |
| NODC_RHISN | P50357 | *Rhizobium* sp. | 413 |
| Q8KLG3_RHIET | Q8KLG3 | *Rhizobium etli* | 443 |
| Q9RAN5_MESS7 | Q9RAN5 | *Mesorhizobium* sp. | 416 |
| Q9Z3I6_BRASS | Q9Z3I6 | *Bradyrhizobium* sp. | 481 |
| NODC_RHILO | P17862 | *Rhizobium loti* | 424 |
| Q8KJI5_RHILO | Q8KJI5 | *Rhizobium loti* | 424 |
| NODC_RHIGA | P50356 | *Rhizobium galegae* | 433 |
| NODC_RHIME | P04341 | *Rhizobium meliloti* | 426 |
| Q9R614_RHIME | Q9R614 | *Rhizobium meliloti* | 424 |
| O52478_RHIME | O52478 | *Rhizobium meliloti* | 402 |
| Q52971_RHIME | Q52971 | *Rhizobium meliloti* | 402 |
| NODC_RHILV | P04340 | *Rhizobium leguminosarum* | 424 |

However, it will be clear that variants of NODC proteins, wherein one or more amino acid residues have been deleted, substituted or inserted, which can be deduced from the above mentioned amino acid sequences, can also be used to the same effect in the methods according to the invention, provided that the enzymatic activity has not changed. These variant NODC proteins may have about 95% sequence identity to any one of the herein mentioned NODC proteins. A method for determining enzymatic activity of NODC proteins in vitro has been described e.g. by Kamst et al., 1997 Journal of Bacteriology, 179, p2103-2108.

Thus, as used herein, an "N-acetylglucosamine transferase that is of the NODC type" is an N-acetylglucosamine transferase that catalyzes the transfer of the GlcNAc moiety from UDP-GlcNAc to a nascent chitin oligosaccharide. Preferably the protein contains the conserved regions which can be found by comparing the different NODC proteins.

Particularly suitable for the methods of the invention are the proteins listed in SEQ ID No 1 to SEQ ID No 9, particularly the protein listed in SEQ ID No 1, and the DNA fragments encoding such a protein.

It has been observed (see experimental section) that NODC proteins when expressed in plant cells are co-localized with the membranes of the Golgi apparatus, in addition to the co-localization with the plasmalemma. To arrive at the incorporation of chito-oligosaccharides into the plant cell wall, no feeding with GlcNAc is required. However, when chitin synthases of fungal origin are used, these proteins are not co-localized with the membranes of the Golgi apparatus, and feeding with GlcNAc is required to arrive at significant incorporation of chito-oligosaccharides into the cell walls. Without intending to limit the invention to a particular mode of action, it is thought that the transmembrane spanning domains of NODC proteins may be more apt to insertion into the membranes of the Golgi apparatus than those of the plasmalemma and that the location of these proteins circumvents the need for external feeding with GlcNAc. Modification of chitin synthase proteins, such as a chitin synthase of fungal origin, e.g a *Neurospora crassa* chitinsynthase, so as to relocate the chitin synthases to the membranes of the Golgi apparatus is sufficient to abolish the need of external GlcNAc feeding. Such relocation has been achieved by linking the chitin synthase protein to a signal anchor peptide targeting the linked protein to membranes of the Golgi apparatus.

Thus, in another embodiment of the invention, a method is provided for increasing the amount of positively charged oligosaccharides in the cell wall, particularly the secondary cell wall of a plant cell, comprising the step of introducing a chimeric gene into the plant cell, said chimeric gene comprising
 a plant-expressible promoter
 a DNA region coding for an N-acetylglucosamine transferase, wherein the N-acetylglucosamine transferase is targeted to the membranes of the Golgi-apparatus; and
 a transcription termination and polyadenylation region.

As used herein, the N-acetylglucosamine transferase is not limited to NODC type proteins, but also includes chitin synthases (Chitin UDP-acetyl-glucosaminyl transferases), such as the chitin synthases of fungal origin. Examples of amino acid sequences of such chitin synthases can be found in the different databases including amino acid sequences with the following identifiers (accession numbers): CHS1_AJECA (P30576) Chitin synthase 1 (EC 2.4.1.16) (Chitin-UDP acetyl-glucosaminyl transferase 1) (Class-I chitin synthase 1) from *Ajellomyces capsulata* (*Histoplasma capsulatum*); CHS1_AJEDE (P30579) Chitin synthase 1 (EC 2.4.1.16) (Chitin-UDP acetyl-glucosaminyl transferase 1) (Class-I chitin synthase 1) from *Ajellomyces dermatitidis* (*Blastomyces dermatitidis*); CHS1_ASPNG (P30581) Chitin synthase 1 (EC 2.4.1.16) (Chitin-UDP acetyl-glucosaminyl transferase 1) (Class-I chitin synthase 1) from *Aspergillus niger*; CHS1_BOTCI (P49603) Chitin synthase 1 (EC 2.4.1.16) (Chitin-UDP acetyl-glucosaminyl transferase 1) (Class-I chitin synthase 1) from *Botrytis cinerea* (Noble rot fungus) (*Botryotinia fuckeliana*); CHS1_CANAL (P23316) Chitin synthase 1 (EC 2.4.1.16) (Chitin-UDP acetyl-glucosaminyl transferase 1). from *Candida albicans* (Yeast); CHS1_CRYNV (O13356) Chitin synthase 1 (EC 2.4.1.16) (Chitin-UDP acetyl-glucosaminyl transferase 1) (Class-IV chitin synthase 1). {GENE: Name=CHS1}-*Cryptococcus neoformans* var. *grubii* (*Filobasidiella neoformans* var. *grubii*); CHS1_EMENI (P30583) Chitin synthase 1 (EC 2.4.1.16) (Chitin-UDP acetyl-glucosaminyl transferase 1) (Class-I chitin synthase 1) (Fragment). {GENE: Name=chs1}-*Emericella nidulans* (*Aspergillus nidulans*); CHS1_EXODE (P30600) Chitin synthase 1 (EC 2.4.1.16) (Chitin-UDP acetyl-glucosaminyl transferase 1) (Class-II chitin synthase 1). {GENE: Name=CHS 1}-*Exophiala dermatitidis* (*Wangiella dermatitidis*); CHS1_EXOJE (P30585) Chitin synthase 1 (EC 2.4.1.16) (Chitin-UDP acetyl-glucosaminyl transferase 1) (Class-I chitin synthase 1) (Fragment). {GENE: Name=CHS1}-*Exophiala jeanselmei*; CHS1_NEUCR (P29070) Chitin synthase 1 (EC 2.4.1.16) (Chitin-UDP acetyl-glucosaminyl transferase 1) (Class-III chitin synthase 3). {GENE: Name=chs-1; ORFNames=B11H24.170, NCU03611.1}-*Neurospora crassa*; CHS1_PHAEX (P30590); Chitin synthase 1 (EC 2.4.1.16) (Chitin-UDP acetyl-glucosaminyl transferase 1) (Fragment). {GENE: Name=CHS1}-*Phaeococcomyces exophialae*; CHS1_PHYBL (P87073) Chitin synthase 1 (EC 2.4.1.16) (Chitin-UDP acetyl-glucosaminyl transferase 1) (Class-II chitin synthase 1). {GENE: Name=chs1}-*Phycomyces blakesleeanus*; CHS1_RHIAT (P30592) Chitin synthase 1 (EC 2.4.1.16) (Chitin-UDP acetyl-glucosaminyl transferase 1) (Class-I chitin synthase 1) (Fragment). {GENE: Name=CHS1}-*Rhinocladiella atrovirens*; CHS1_RHIOL (P30594) Chitin synthase 1 (EC 2.4.1.16) (Chitin-UDP acetyl-glucosaminyl transferase 1). {GENE: Name=CHS1}-*Rhizopus oligosporus*; CHS1_RHIRA (Q12632) Chitin synthase 1 (EC 2.4.1.16) (Chitin-UDP acetyl-glucosaminyl transferase 1) (Class-II chitin synthase 1). {GENE: Name=CHS1}-*Rhizomucor racemosus* (*Mucor circinelloides* f. *lusitanicus*); CHS1_SCHCO (P30596); Chitin synthase 1 (EC 2.4.1.16) (Chitin-UDP acetyl-glucosaminyl transferase 1) (Fragment). {GENE: Name=CHS 1}-*Schizophyllum commune* (Bracket fungus); CHS1_SCHPO (P30597) Chitin synthase 1 (EC 2.4.1.16) (Chitin-UDP acetyl-glucosaminyl transferase 1). {GENE: Name=chs1; ORFNames=SPAC13G6.12c, SPAC24B11.01c}-*Schizosaccharomyces pombe* (Fission yeast); CHS1_TUBUN (P55003) Chitin synthase 1 (EC 2.4.1.16) (Chitin-UDP acetyl-glucosaminyl transferase 1) (Fragment). {GENE: Name=CHS1}-*Tuber uncinatum* (Burgundy truffle); CHS1 USTMA (P30598) Chitin synthase 1 (EC 2.4.1.16) (Chitin-UDP acetyl-glucosaminyl transferase 1) (Fragment). {GENE: Name=CHS 1}-*Ustilago maydis* (Smut fungus); CHS1_XYLBA (P30603) Chitin synthase 1 (EC 2.4.1.16) (Chitin-UDP acetyl-glucosaminyl transferase 1) (Fragment). {GENE: Name=CHS1}-*Xylohypha bantiana*; CHS1 YEAST (P08004) Chitin synthase 1 (EC 2.4.1.16) (Chitin-UDP acetyl-glucosaminyl transferase 1). {GENE: Name=CHS1; *Saccharomyces cerevisiae* (Baker's yeast); CHS2 AJECA (P30577) Chitin synthase 2 (EC 2.4.1.16) (Chitin-UDP acetyl-glucosaminyl transferase 2) (Class-III chitin synthase 2) *Ajellomyces capsulata* (*Histoplasma capsulatum*); CHS2 AJEDE (P30580) Chitin synthase 2 (EC 2.4.1.16) (Chitin-UDP acetyl-glucosaminyl transferase 2) (Class-II chitin synthase 2) {GENE: Name=CHS2}-*Ajellomyces dermatitidis* (*Blastomyces dermatitidis*) CHS2_ASPNG (P30582); Chitin synthase 2 (EC 2.4.1.16) (Chitin-UDP acetyl-glucosaminyl transferase 2) (Class-II chitin synthase 2) (Fragment). {GENE: Name=chs2}-*Aspergillus niger*; CHS2_CANAL (P30572) Chitin synthase 2 (EC 2.4.1.16) (Chitin-UDP acetyl-glucosaminyl transferase 2). {GENE: Name=CHS2}-*Candida albicans* (Yeast); CHS2_EXODE (P30601) Chitin synthase 2 (EC 2.4.1.16) (Chitin-UDP acetyl-glucosaminyl transferase 2) (Class-I chitin synthase 2). {GENE: Name=CHS2}-*Exophiala dermatitidis* (*Wangiella dermatitidis*); CHS2_EXOJE (P30586) Chitin synthase 2 (EC 2.4.1.16) (Chitin-UDP acetyl-glucosaminyl transferase 2) (Fragment). {GENE: Name=CHS2}-*Exophiala jeanselmei*; CHS2_NEUCR (P30589); Chitin synthase 2 (EC 2.4.1.16) (Chitin-UDP acetyl-glucosaminyl transferase 2). {GENE: Name=chs-2; ORFNames=NCU05239.1}-*Neurospora crassa*; CHS2_PARBR (Q92444) Chitin synthase 2 (EC 2.4.1.16) (Chitin-UDP acetyl-glucosaminyl transferase 2) (Class-II chitin synthase 2). {GENE: Name=CHS2}-*Paracoccidioides brasiliensis*; CHS2_PHAEX (P30591); Chitin synthase 2 (EC 2.4.1.16) (Chitin-UDP acetyl-glucosaminyl transferase 2) (Class-II chitin synthase 2) (Fragment). {GENE: Name=CHS2}-*Phaeococcomyces exophialae*; CHS2_RHIAT (P30593) Chitin synthase 2 (EC 2.4.1.16) (Chitin-UDP acetyl-glucosaminyl transferase 2) (Class-III chitin synthase 2) (Fragment). {GENE: Name=CHS2}-*Rhinocladiella atrovirens*; CHS2_RHIOL (P30595) Chitin synthase 2 (EC 2.4.1.16) (Chitin-UDP acetyl-glucosaminyl transferase 2). {GENE: Name=CHS2}-*Rhizopus oligosporus*; CHS2_SCHPO (O74756) Chitin synthase-like protein 2. {GENE: Name=chs2; ORFNames=SPBC1709.01, SPBC1734.17}-*Schizosaccharomyces pombe* (Fission yeast); CHS2_USTMA (P30599) Chitin synthase 2 (EC 2.4.1.16) (Chitin-UDP acetyl-glucosaminyl transferase 2) (Fragment). {GENE: Name=CHS2}-*Ustilago maydis* (Smut fungus); CHS2_XYLBA (P30604) Chitin synthase 2 (EC 2.4.1.16) (Chitin-UDP acetyl-glucosaminyl transferase 2) (Class-II chitin synthase 2) (Fragment). {GENE: Name=CHS2}-*Xylohypha bantiana*; CHS2_YEAST (P14180); Chitin synthase 2 (EC 2.4.1.16) (Chitin-UDP acetyl-glucosaminyl transferase 2). {GENE: Name=CHS2; OrderedLocusNames=YBR038W; ORFNames=YBR0407}-*Saccharomyces cerevisiae* (Baker's yeast); CHS3_AJECA (P30578) Chitin synthase 3 (EC 2.4.1.16) (Chitin-UDP acetyl-glucosaminyl transferase 3) (Class-II chitin synthase 3) (Fragment). {GENE: Name=CHS3}-*Ajellomyces capsulata* (*Histoplasma capsulatum*); CHS3_CANAL (P30573) Chitin synthase 3 (EC 2.4.1.16) (Chitin-UDP acetyl-glucosaminyl transferase 3) (Class-IV chitin synthase 3). {GENE: Name=CHS3}-*Candida albicans* (Yeast); CHS3_EXODE (P30602) Chitin synthase 3 (EC 2.4.1.16) (Chitin-UDP acetyl-glucosaminyl transferase 3) (Class-III chitin synthase 3). {GENE: Name=CHS3}-*Exophiala dermatitidis* (*Wangiella dermatitidis*); CHS3_EXOJE (P30587); Chitin synthase 3 (EC 2.4.1.16) (Chitin-UDP acetyl-glucosaminyl transferase 3) (Class-III chitin synthase 3) (Fragment). {GENE: Name=CHS3}-*Exophiala jeanselmei*; CHS3_NEUCR (P30588) Chitin synthase 3 (EC 2.4.1.16) (Chitin-UDP acetyl-glucosaminyl transferase 3). {GENE: Name=chs-3; ORFNames=G65A3.040}-*Neurospora crassa*; CHS3_YEAST (P29465) Chitin synthase 3 (EC 2.4.1.16) (Chitin-UDP acetyl-glucosaminyl transferase 3) (Class-IV chitin synthase 3). {GENE: Name=CHS3; Synonyms=CAL1, CSD2, DIT101, KIT2; Ordered Locus Names=YBR023C; ORFNames=YBR0305}-*Saccharomyces cerevisiae* (Baker's yeast); CHS4_MAGGR (O13353); Chitin synthase 4 (EC 2.4.1.16) (Chitin-UDP acetyl-glucosaminyl transferase 4) (Class-IV chitin synthase 4). {GENE: Name=CHS4}-*Magnaporthe grisea* (Rice blast fungus) (*Pyricularia grisea*); CHS4_NEUCR (Q01285) Chitin synthase 4 (EC 2.4.1.16) (Chitin-UDP acetyl-glucosaminyl transferase 4) (Class-IV chitin synthase 4). {GENE: Name=chs-4; ORFNames=NCU09324.1}-*Neurospora crassa*; CHS5_USTMA (O13394) Chitin synthase 5 (EC 2.4.1.16) (Chitin-UDP acetyl-glucosaminyl transferase 5) (Class-IV chitin synthase 5). {GENE: Name=CHS5}-*Ustilago maydis* (Smut fungus); CHS6_USTMA (O13395) Chitin synthase 6 (EC 2.4.1.16) (Chitin-UDP acetyl-glucosaminyl transferase 6) (Class-V chitin synthase 6). {GENE: Name=CHS6}-*Ustilago maydis* (Smut fungus); CHSA_AMPQU (Q12564); Chitin synthase A (EC 2.4.1.16) (Chitin-UDP acetyl-glucosaminyl transferase A) (Class-I chitin synthase A). {GENE: Name=CHSA}-*Ampelomyces quisqualis*; CHSA_EMENI (P30584) Chitin synthase A (EC 2.4.1.16) (Chitin-UDP acetyl-glucosaminyl transferase A) (Class-II chitin synthase A). {GENE: Name=chsA; Synonyms=chs2}-*Emericella nidulans* (*Aspergillus nidulans*); CHSB_EMENI (Q00757) Chitin synthase B (EC 2.4.1.16) (Chitin-UDP acetyl-glucosaminyl transferase B) (Class-III chitin synthase B). {GENE: Name=chsB}-*Emericella nidulans* (*Aspergillus nidulans*); CHSC_ASPFU (Q92197) Chitin synthase C (EC 2.4.1.16) (Chitin-UDP acetyl-glucosaminyl transferase C) (Class-III chitin synthase C). {GENE: Name=chsC}-*Aspergillus fumigatus* (*Sartorya fumigata*); CHSD_ASPFU (P78746) Chitin synthase D (EC 2.4.1.16) (Chitin-UDP acetyl-glucosaminyl transferase D) (Class-VI chitin synthase D). {GENE: Name=chsD}-*Aspergillus fumigatus* (*Sartorya fumigata*); CHSD_EMENI (P78611) Chitin synthase D (EC 2.4.1.16) (Chitin-UDP acetyl-glucosaminyl transferase D) (Class-V chitin synthase D). {GENE: Name=chsD; Synonyms=chsE}-*Emericella nidulans* (*Aspergillus nidulans*); CHSG_ASPFU (P54267); Chitin synthase G (EC 2.4.1.16) (Chitin-UDP acetyl-glucosaminyl transferase G) (Class-III chitin synthase G). {GENE: Name=chsG}-*Aspergillus fumigatus* (*Sartorya fumigata*); CHSX_USTMA (Q99126) Chitin synthase 1 (EC 2.4.1.16) (Chitin-UDP acetyl-glucosaminyl transferase 1). {GENE: Name=CHS1}-*Ustilago maydis* (Smut fungus); CHSY_USTMA (Q99127) Chitin synthase 2 (EC 2.4.1.16) (Chitin-UDP acetyl-glucosaminyl transferase 2). {GENE: Name=CHS2}-*Ustilago maydis* (Smut fungus) or CHS_SAPMO (P48017) Chitin synthase (EC 2.4.1.16) (Chitin-UDP acetyl-glucosaminyl transferase). {GENE: Name=CHS}-*Saprolegnia monoica*. All sequences are incorporated herein by reference.

Chitin synthases should preferably be equipped with (heterologous) signal anchor sequences targeting the chitin synthase to the membranes of the Golgi apparatus. Such sequences are known in the art, including the sequences within and adjacent to the transmembrane segment of α-2,6-sialyltransferase (particularly the first 44 or 52 amino acids thereof; Munro et al. 1991, EMBO Journal, 10: 3577-3588); the signal anchor sequence from human galactosyl transferase (particularly the first 60 amino acids thereof) or the signal anchor sequence from the *Arabidopsis* homologue of the yeast HDEL receptor (AtERD2) (Saint-Jore et al., 2002, The Plant Journal, 29: 661-678), the signal anchor sequence from β1,2-xylosyltransferase protein (particularly the first 36 amino acids thereof; Pagny et al., 2003, The Plant Journal 33: 189-203) or the signal anchor sequences of N-acetyl-glucosaminyl transferase I (particularly the first 77 amino acids thereof; Essl et al. 1999, FEBS Lett. 453:169-173) (all publication incorporated herein by reference). Other Golgi targeting signals to be employed by fusion at the C-terminus of the N-acetylglucosamine transferase include the amino acid sequence "YYHDL" as can be found in *Arabidopsis* DAGAT1 protein or "LKLEI" as can be found in *Arabidopsis* DAGAT2. Fusion of such signal anchor sequences to chitin synthases by linking DNA fragments encoding the respective polypeptides can be achieved using standard recombinant DNA techniques. N-acetylglucosamine transferases of the NODC type may also be operably linked to signal anchor sequences targeting the Golgi apparatus.

In another embodiment of the invention, a method is provided for increasing the amount of positively charged oligosaccharides in the cell wall, particularly the secondary cell wall of a plant cell, comprising the step of introducing a chimeric gene into the plant cell, wherein the chimeric gene comprises the following operably linked DNA fragments
 a plant-expressible promoter;
 a DNA region coding for chitin synthase (chitin UDP-acetylglucosamine transferase), preferably of fungal origin; and
 a transcription termination and polyadenylation region
and further comprising the step of applying an effective amount of N-acetylglucosamine or N-acetylglucosamine-1-phosphate or N-acetylglucosamine-6-phosphate or glucosamine-6-phosphate to the plant cell or to the plant.

The chimeric genes according to the invention comprise a plant-expressible promoter. As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, or T-DNA gene promoters and the like.

A plant-expressible promoter that controls initiation and maintenance of transcription preferentially in fiber cells is a promoter that drives transcription of the operably linked DNA region to a higher level in fiber cells and the underlying epidermis cells than in other cells or tissues of the plant. Such promoters include the promoter from cotton from a fiber-specific β-tubulin gene (as described in WO0210377), the promoter from cotton from a fiber-specific actin gene (as described in WO0210413), the promoter from a fiber specific lipid transfer protein gene from cotton (as described in U.S. Pat. No. 5,792,933), a promoter from an expansin gene from cotton (WO9830698) or a promoter from a chitinase gene in cotton (US2003106097) or the promoters of the fiber specific genes described in U.S. Pat. No. 6,259,003 or U.S. Pat. No. 6,166,294.

The invention further provides plant cell walls, comprising fibers including such cell walls obtained from plant cells using the methods according to the invention. Such plant cell walls comprise positively charged oligo- or polysaccharides, such as N-acetylglucosamine oligomers or chitin, embedded into the cellulose. These plant cell walls may be further modified, e.g. partly or completely deacetylated such that oligomers comprising glucosamine residues are obtained. The amino-group of the resulting glucosamines is chemically more reactive than the aminoacetyl group of N-acetylglucosamine or the hydroxyl group of cellulose.

The plant cell wall obtained according to the invention, particularly those which have been subjected to a deacetylation step, can be further chemically modified. Products containing such plant cell walls, such as fibers, yarns or fabrics have qualities resembling those of the cellulose-chitosan blends described in the art, including improved dyeability, improved inhibition of e.g. dermatophytes, controlled drug release etc.

In a specific embodiment, the invention provides cotton fibers obtained from or which can be obtained from cotton plants according to the methods of the invention. In other words, cotton fibers are provided from cotton plants comprising in the genome, such as the nuclear genome, of their cells a chimeric gene comprising a plant-expressible promoter operably linked to a DNA region coding for an N-acetylglucosamine transferase, wherein the N-acetylglucosamine transferase is targeted to the membranes of the Golgi-apparatus or cotton fibers are provided from cotton plants comprising in the genome, such as the nuclear genome, of their cells a chimeric gene comprising a plant-expressible promoter operably linked to a DNA region coding for an N-acetylglucosamine transferase of the NODC type, or cotton fibers are provided from cotton plants comprising in the genome, such as the nuclear genome, of their cells a chimeric gene comprising a plant-expressible promoter operably linked to a DNA region coding for a chitin synthase. Particularly in the latter case, it may be advantageous to apply to the plant cells or plants an effective amount of N-acetylglucosamine or N-acetylglucosamine-1-phosphate or N-acetylglucosamine-6-phosphate or glucosamine-6-phosphate. Particular embodiments of DNA coding regions or promoters comprised in the chimeric genes transferred into cotton plants are as described elsewhere in this document.

The cotton fibers according to the invention can be distinguished from naturally occurring cotton fibers, i.e. cotton fibers obtained from an isogenic line which does not comprise a chimeric gene according to the invention, by the capacity of such fibers for increased staining with anionic dyes (including e.g. Congo Red), by the capacity of such fibers for increased staining with amine-reactive dyes (including e.g. tetrafluorophenyl ester). The cotton fibers according to the invention also have the capacity of binding of Wheat germ agglutinin which binds chito-oligomers. The cotton fibers according to the invention can also be distinguished from naturally occurring cotton fibers by direct detection of the N-acetylglucosamine and GlcNAc oligmers, such as chitobiose, preferably after treatment of the fiber cell wall material with chitinase. The cotton fibers according to the invention may also be distinguished by their increased nitrogen content.

Cotton fibers according to the invention can also be distinguished from the chitosan coated fibers or from chitosan/cellulose blended yarns, in that the positively charged oligomers are more or less evenly distributed in the secondary plant cell walls making up the fibers. Accordingly, in microscopical sections of cotton fibers, stained e.g. with WGA or with congo red or with tetrafluorophenyl as described hereinafter, the dyes will be distributed more or less evenly throughout the cell walls making up the cotton fibers, whereas in chitosan-coated fibers, the staining will be concentrated at the coat of chitosan located as a sheet at the surface of the treated fibers.

Cotton fibers according to the invention can also be distinguished from other cotton fibers by detection of the N-acetylglucosamine transferase comprising chimeric genes in nucleic acids which remain in the plant material associated with cotton fibers.

The increased staining of the plant cell wall material according to the invention, by anionic dyes such as congo-red can be quantified e.g. by dying a uniform amount of material under standard conditions, spreading out the material over a standardized area (such as a well in a multiwell plate) digitalizing a picture of the area for the gray scale of the colored layer of material. The less gray, the more stained the plant cell wall material is. In this way, cotton fibers and cell wall material according to the invention showed an increase of at least about 5% in staining by congo-red compared to control cell wall material or fibers from isogenic plant lines without an N-acetylglucosamine transferase encoding gene.

The capacity of the novel cotton fibers to specifically bind wheat germ agglutin (detectable by the coupled flurophoric group) is a clear distinguishing feature of the provided novel cotton fibers over the naturally occurring cotton fibers. Except for a very low background fluorescence, naturally occurring cotton fibers do not stain/fluoresce when treated with WGA-alexa fluor 488 or 555. The fluorescence of cotton fibers increases a least 5 times when chito-oligomers are present. Accordingly, the invention provides cotton fibers which are capable of specifically binding wheat germ agglutinin, or WGA coupled to a flurophore, such as WGA Alexa 488 or WGA Alexa 555 or which, when treated with WGA Alexa 488 or WGA Alexa 555 provide a bright fluorescence under UV light. This fluorescence is not restricted to the surface of the cotton fiber but is distributed throughout the cell wall of the fiber cells.

Plant cell wall material according to the invention, including cotton fibers typically possess chito-oligosaccharides in a concentration of at least 0.1 µg/mg cell wall material, preferably at least 1 µg/mg cell wall material, preferably at least 5 µg/mg cell wall material.

The invention also provides the chimeric genes as herein described, and plant cells or plants containing such chimeric genes.

Wherever the methods of the invention are directed to introduction of a chimeric gene in a plant cell, it will be clear that such methods can also be applied in cases whereby the plant cell is incorporated into a mature plant. E.g. transgenic cells may be regenerated into transgenic plants according to established methods.

Methods to transform plants cells and plants are well known in the art. Methods to transform cotton plants are also well known in the art. *Agrobacterium*-mediated transformation of cotton has been described e.g. in U.S. Pat. No. 5,004,863 or in U.S. Pat. No. 6,483,013 and cotton transformation by particle bombardment is reported e.g. in WO 92/15675.

The chimeric genes may be introduced by transformation in cotton plants from which embryogenic callus can be derived, such as Coker 312, Coker310, Coker 5Acala SJ-5, GSC25110, FiberMax 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B 1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 and ORO BLANCO PIMA, Fibermax® FM5013, FM5015, FM5017, FM989, FM832, FM966 and FM958, FM989, FM958, FM832, FM991, FM819, FM800, FM960, FM966, FM981, FM5035, FM5044, FM5045, FM5013, FM5015, FM5017 or FM5024 and plants with genotypes derived thereof.

"Cotton" as used herein includes *Gossypium hirsutum, Gossypium barbadense, Gossypium arboreum* and *Gossypium herbaceum* or progeny from crosses between such species.

The methods and means of the current invention may also be employed for other plant species such as hemp, jute, flax and woody plants, including but not limited to *Pinus* spp., *Populus* spp., *Picea* spp., *Eucalyptus* spp. etc.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The following non-limiting Examples describe the methods for altering plant cell walls. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and Examples, reference is made to the following sequences represented in the sequence listing:

SEQ ID No 1: Nodulation protein C of *Azorhizobium caulinodans*

SEQ ID No 2: Nodulation protein C of *Bradyrhizobium japonicum*

SEQ ID No 3: Nodulation protein C of *Rhizobium galegae*

SEQ ID No 4: Nodulation protein C of *Rhizobium leguminosarum* (biovar *viciae*)

SEQ ID No 5: Nodulation protein C of *Rhizobium meliloti*

SEQ ID No 6: Nodulation protein C of *Rhizobium tropici*

SEQ ID No 7: Nodulation protein C of *Rhizobium leguminosarum* (biovar *phaseoli*)

SEQ ID No 8: Nodulation protein of *Rhizobium* sp. Strain N33

SEQ ID No 9: Nodulation protein of *Rhizobium loti*

SEQ ID No 10: T-DNA of pTGK42

SEQ ID No 11: T-DNA of pTGK44

SEQ ID No 12: T-DNA of pTDBI5

SEQ ID No 13: T-DNA of pTDBI37

SEQ ID No 14: T-DNA of pTDBI50

SEQ ID No 15: Synthetic Chitin synthase linked to Golgi-targeting signal.

EXAMPLES

Example 1

Construction of Chimeric Plant-Expressible Genes Encoding a N-Acetylglucosamine Transferase Protein Using standard recombinant DNA techniques, a plant expressible NODC chimeric gene was constructed containing the following operably linked DNA fragments:
- a 35S promoter region from CaMV
- a DNA fragment coding for an untranslated leader sequence (5'Cab22L)
- a DNA fragment coding for NODC of *Azorhizobium caulinodans*
- a DNA fragment coding for EGFP (enhanced green fluorescent protein) cloned in frame with the NODC encoding ORF, such that a fusion protein is made comprising NODC and EGFP
- a transcription termination and polyadenylation signal from the 35S transcript of CaMV (3' 35S)

The chimeric gene was introduced between T-DNA borders of a T-DNA vector together with a chimeric bar gene providing resistance to phosphinotricin. The resulting T-DNA vector was named pTGK44. The sequence of the T-DNA of this vector is provided in SEQ ID No 11. This T-DNA vector allowed histochemical analysis of the localization of the NODC-EGFP fusion protein.

Another chimeric gene was constructed containing the following operably linked DNA fragments:
- a 35S promoter region from CaMV
- a DNA fragment coding for an untranslated leader sequence (5'Cab22L)
- a DNA fragment coding for NODC of *Azorhizobium caulinodans*
- a transcription termination and polyadenylation signal from the 35S transcript of CaMV (3' 35S)

The chimeric gene was introduced between T-DNA borders of a T-DNA vector together with a chimeric bar gene providing resistance to phosphinotricin. The resulting T-DNA vector was named pTGK42. The sequence of the T-DNA of this vector is provided in SEQ ID No 10. This T-DNA vector allowed to express NODC in plant cells, to analyse whether chito-oligosaccharides were produced associated with the cell wall of such plant cells.

A control chimeric gene encoding an N-acetylglucosamine transferase which is different from the NODC type protein was also constructed containing the following operably linked DNA fragments:
- a 35S promoter region from CaMV
- a DNA fragment coding for an untranslated leader sequence (5'Cab22L)
- a DNA fragment coding for chitin synthase of *Neurospora crassa*
- a transcription termination and polyadenylation signal from the 35S transcript of CaMV (3' 35S)

The chimeric gene was introduced between T-DNA borders of a T-DNA vector together with a chimeric bar gene providing resistance to phosphinotricin. The resulting T-DNA vector was named pTGK43. The sequence of the T-DNA of this vector is provided in SEQ ID No 12. This T-DNA vector allowed to express chitin synthase in plant cells, to analyse whether chito-oligosaccharides were produced associated with the cell wall of such plant cells.

The T-DNA vectors were introduced into *Agrobacterium tumefaciens* C58C1Rif(pEHA101). For control experiments, a T-DNA vector containing only a chimeric bar gene was introduced into the same *Agrobacterium* strain.

The *A. tumefaciens* strains were subsequently used to generate hairy root cultures from *Arabidopsis thaliana* by co-transformation of leaf disks with *Agrobacterium rhizogenes* ATCC15834 and the *A. tumefaciens* strains carrying the different T-DNA vectors according to the following protocol.

The following media were used:
Germination medium: MS salts/2, B5 vitamines, 1.5% sucrose, pH 5.8, 0.7% agar (Difco)
Standard medium: MS medium, 0.5 g/L MES, 2% glucose, pH 5.8, 0.7% agar (Difco)
Callus inducing medium: MS medium, 0.5 g/L MES, 2% glucose, pH 5.8, 0.7% agar (Difco), 0.2 mg/L 2,4D and 0.2 mg/L kinetine
Hairy root elongation medium: MS medium, 2% sucrose, pH 6.2, 0.7% agar (Difco)
Root culture medium: B5 medium, 3% sucrose, pH 5.5.

In vitro *Arabidopsis* shoots were cultured from sterilized seeds in the following way.

Seeds were treated for 2 minutes with 70% EtOH, followed by a 10 minutes bleach with 6% active chlorine+0.05% Tween 20, and 5 washes with sterile tap water. Seeds were pregerminated in the light (30-50 µEinstein m-2 sec-1) for 24 hours at 24° C. in sterile tap water (about 10-12 mL tap water in 9 cm Falcon Optilux Petridish, nr. 1005).

Pregerminated seeds were put on germination medium and allowed to grow with the following light regime: 12 hours light/12 hours dark or 16 hours light/8 hours dark (30-50 µEinstein m-2 sec-1) at 23-24° C. for about 2-3 weeks. *A. rhizogenes* strains were grown on agar plates with YEB medium, while *A. tumefaciens* strains were grown on agar plates with minA medium supplement with antibiotics appropriate to select for the maintenance of the T-DNA vector.

For transformation, leaves were cut in two halves and placed on Callus inducing medium. *A. rhizogenes* and *A. tumefaciens* bacteria were resuspended in Standard medium to obtain an OD600 of about 0.2-0.3, mixed in a 1:1 ratio and used for incubation of the leaf pieces for about 5 minutes. Afterwards, the bacterial suspension was removed and infected leaf pieces were placed on Standard medium and incubated for about 3 days (23-24° C.; 30 µEinstein m-2 sec-1; 12 hours light/12 hours dark or 16 hours light/8 hours dark).

Thereafter, leaf explants were washed 3 times with 'Standard medium' containing 500 mg/L tricarcillin (Duchefa) and transferred to (20-30 mg/L gluphosinate) 'Standard medium' containing (20-30 mg/L gluphosinate and 500 mg/L tricarcillin and further cultured at 23-24° C.; 30 µEinstein m-2 sec-1; 12 hours light/12 hours dark or 16 hours light/8 hours dark. Leaf explants were transferred each week to fresh medium. After 3-4 weeks emerging roots were severed and transferred to 'Hairy root elongation medium'. When the roots were a few centimeters, a hairy root culture in 250 mL erlenmeyers containing 50 mL 'Root culture medium'+250 mg/L tricarcillin was started. The cultures were shaken (110 rpm) in the dark at 23-24° C. and subcultured every week. The tricarcillin concentration was reduced gradually.

When the roots were growing well, the roots were broken into pieces of about 1.5 cm and the explants were distributed over several erlenmeyers.

Hairy root cultures could also be cultured on solid medium, whereby the cultures were transferred every two weeks to fresh 'Hairy root elongation medium'

A similar protocol can be used to generate hairy root cultures from cotton.

Example 2

Histochemical Analysis of the Hairy Root Cultures

Root hairs of the different hairy root cultures obtained by co-infection between *A. rhizogenes* and *A. tumefaciens* carrying the different T-DNA vectors described in Example 1 were histochemically stained to visualize different compounds of the cells, and analyzed microscopically.

The localization of NODC-EGFP fusion protein can be visualized using the green fluorescence of the GFP part. N-acetylglucosamine can be either detected after immunological reaction with IgM monoclonal antibodies to N-acetylglucosamine (BIODESIGN) or using Wheat Germ Agglutinin-Alexa Fluor 488. The endoplasmatic reticulum was stained using ER-Tracker Blue White DPX dye. The Golgi apparatus was visualized using BODIPY-TR. Cell walls were stained using Calcofluor White (Fluorescent brightener 28). Nuclei were stained using Hoechst 33342.

The histochemically stained root hair cells were examined by means of fluorescence microscopy, using an Axioplan 2 microscope (Zeiss, Jena, Germany) equipped with Apotome (Zeiss) to allow optical sections. Axio Vision 4.2 (Zeiss) was used for image processing.

The following protocols were used for the different histochemical methods:

A. Calcofluor Staining of Cell Walls.

Calcofluor White (or Fluorescent Brightener 28) is a colourless organic compound that fluoresces in a clear bluish color under ultraviolet radiation ($\lambda$max=350 nm).

The specimen to be stained is immersed for 15 to 30 minutes in culture medium or PBS (buffer solution) comprising Fluorescent Brightener 28 at 50 µg/mL final concentration. The specimen is then washed with medium or buffer, and samples are examined using a microscope equipped for fluorescence microscopy using Zeiss filter set 18. Cell walls fluoresce in a clear bluish color.

B. Histochemical Staining the Golgi Complex and Endoplasmatic Reticulum in Living Cells For staining the Golgi complex, roots cultured for about 5 days in liquid root culture medium were used. These roots were rinsed with fresh root culture medium and incubated for about 30 minutes at 4° C. with 1 µM BODIPY TR C5-ceramide (Molecular probes, Cat No B-34400). The roots were rinsed a few times with root culture medium and incubated in fresh root culture medium at room temperature for 30 minutes with gentle shaking. The roots were then rinsed with fresh root culture medium and examined with a fluorescence microscope Axioplan 2 (Zeiss, Jena, Germany) using Filterset 00 (excitation: BP530/585; emission: LP615).

For staining the ER, roots cultured for about 5 days in liquid root culture medium were used. These roots were rinsed with fresh root culture medium and incubated with ER-Tracker Blue-White DPX (100 nM) dissolved in root culture medium for about 2 hours with gentle shaking. The roots were rinsed a few times with root culture medium and examined with a fluorescence microscope Axioplan 2 (Zeiss, Jena, Germany) using Filterset 02 (excitation: G365; emission: LP420).

C. Whole Mount Immunohistochemical Detection of Incorporated N-Acetylglucosamine in the Cell Wall of Roots (Root Hairs)

Roots of the different hairy root cultures were grown in liquid culture for 6 days, either supplemented with 50 mM GlcNAc or without any supplement. The roots were fixed and dehydrated, rehydrated and cell wall permeabilized in the following way.

When the sample has been incubated with N-acetylglucosamine the excess N-acetylglucosamine is washed away by incubating 4 times 10 min. with PBS solution.

Samples were fixed by incubation and vacuum infiltration of AA solution (incubation: four times 1 hr, each time followed by 5 min vacuum infiltration). AA solution contains 50% EtOH and 5% acetic acid.

In a next step the samples are dehydrated by rinsing with 50% EtOH and washing 2×30 min. with 50% EtOH, followed by 60 min. incubation in 70% EtOH. Samples can be stored at this stage at −20° C.

Subsequently, the samples were subjected to cell wall permeabilisation, by washing 5 min. with 50% EtOH, washing 2×5 min. with PBT (PBS with 0.1% Tween20), washing 2×5 min. with PBT+0.3% Triton X100 and finally washing 2×5 min. with PBS (150 mM NaCl; 10 mM Na-phosphate buffer; pH 7.4).

Permeabilized roots are transferred to a Petridish containing MQ-water, and mounted on a "Vectaboin-treated" microscope slide. The slides are baked on a TLC plate heater for 45 min at 55° C. A blocking step is performed by incubating the slides for one hour with blocking solution (1% BSA in PBT). Afterwards, the 1% blocking solution is replaced with about 400 µL IgM monoclonal antibody to N-acetylglucosamine (1 µg/mL in blocking solution; BIODESIGN, Cat No H67108M) and incubated for one hour. The slides are subsequently washed 3 times 5 to 10 minutes with blocking solution. The blocking solution is then replaced with about 400 µL Goat Anti-Mouse IgM antibody labelled with Alexa Fluor 488 (3 µg/mL in blocking solution; Molecular Probes, Cat No A-21042) and incubated for one hour. Thereafter, slides are washed 5 to 10 minutes with blocking solution, 2 times 5 to 10 minutes with PBT and a few times with PBS to remove Tween20. Results are evaluated by means of fluorescence microscopy with an Axioplan 2 microscope (Zeiss, Jena, Germany) using Filterset 38 (excitation: BP470/40; emission: BP525/50).

D. Wheat Aglutinin Mediated Detection of N-Acetylglusoamine

Roots of the different hairy root cultures were grown in liquid culture for 6 days, either supplemented with 50 mM GlcNAc or without any supplement. The roots were fixed and dehydrated, rehydrated and cell wall permeabilized as described in section C above.

Wheat germ agglutinin selectively binds to N-acetylglucosamine and N-acetylneuraminic acid residues. N-acetylneuraminic acid does not occur in plants. Therefore, in plants, wheat germ agglutinin can be used to specifically detect N-acetylglucosamine residues.

Permeabilized roots were placed in 9 cm Petri Dishes containing PBT. The roots were thereafter transferred to the wells of 6-well culture plates containing about 1.7 µg/mL Wheat Germ Agglutinin labelled with Alexa Fluor 488 (Molecular Probes, Cat No W-11261) in PBT and incubated for one hour. The samples were subsequently washed for 3×10 minutes with PBT and twice for 5 minutes with PBS (to remove Tween20). The samples were placed on a 'Vectabond-treated' or 'Tissue Tack' microscope slide in a drop of PBS. After removal of most of the PBS the coverslide was mounted.

Results were evaluated by means of fluorescence microscopy using a fluorescence microscope Axioplan 2 (Zeiss, Jena, Germany) using Filterset 38 (excitation: BP470/40; emission: BP525/50).

E. GFP Analysis.

EGFP fluorescence was evaluated by means of fluorescence microscopy with an Axioplan 2 microscope (Zeiss, Jena, Germany) using Filterset 38 (excitation: BP470/40; emission: BP525/50).

Results

1. Localization of N-acetylglucosamine in the cell wall

Figure 3:
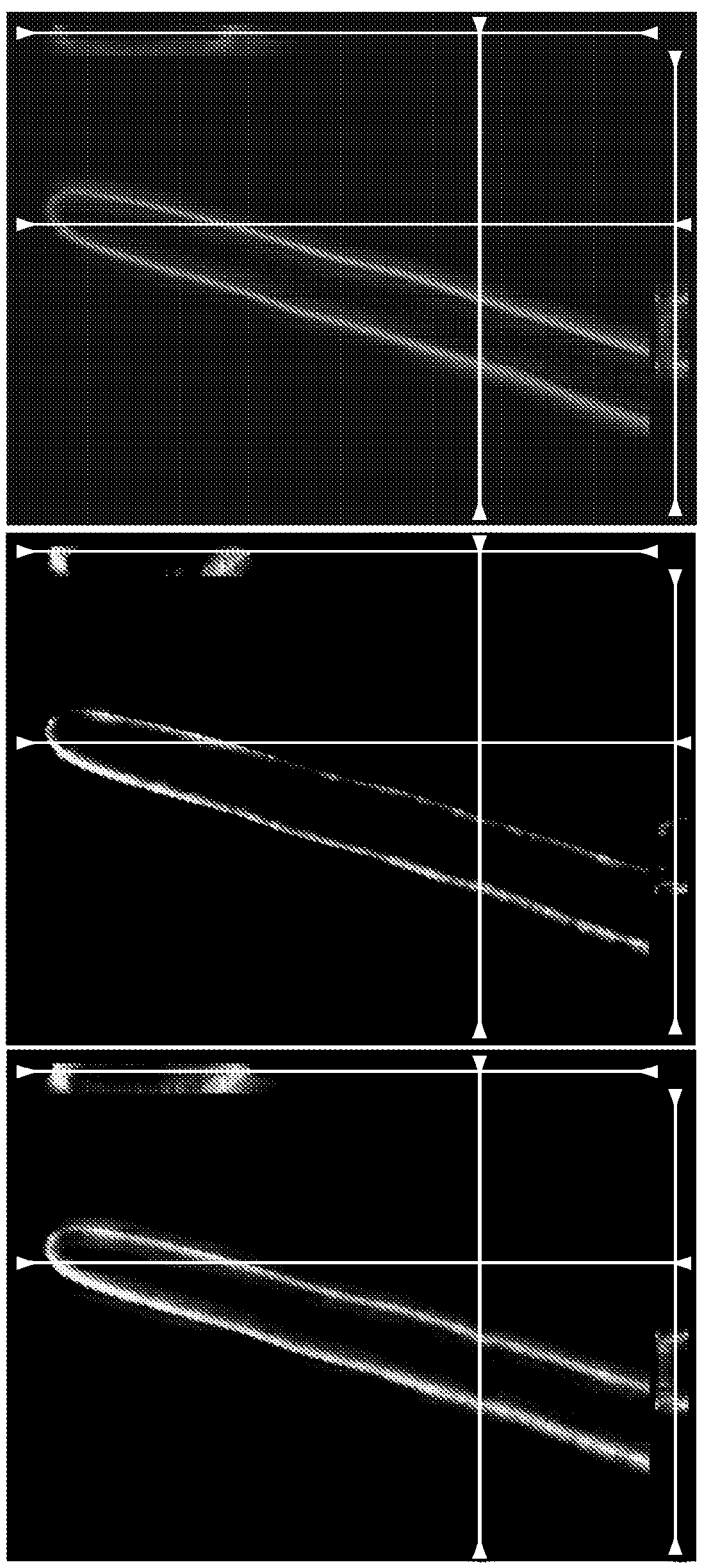
FIG. 3: Photographs of fluorescent microscopy performed on root hair cells from hairy roots containing the 35S::NodC chimeric gene.

Root hair cells comprising the chimeric NODC gene were immunohistochemically stained for the presence of N-acetylglucosamine and subsequently stained with Calcofluor to visualize the cell walls. FIG. 3 shows a representative set of photographs of optical sections using a fluorescence microscope, whereby panel A shows the (blue) fluorescence visualizing the cell wall, and panel B shows the (green) fluorescence visualizing N-acetylglucosamine. As can be seen from the superposition of both optical sections in panel C, the presence of N-acetylglucosamine is exclusively detected in the cell walls of the root hair cells.

2. Co-Localization of NODC Proteins and the Golgi Apparatus

Root hair cells comprising the chimeric gene expressing the NODC-EGFP fusion protein were stained to visualize the Golgi apparatus and subsequently stained with Calcofluor to visualize the cell walls. FIG. 4 shows a representative set of photographs of optical sections using a fluorescence microscope, whereby panel B shows the (blue) fluorescence visualizing the cell wall, panel C shows the (red) fluorescence associated with the Golgi apparatus and panel D shows the (green) fluorescence visualizing the NODC-EGFP fusion protein. As can be seen from the superposition of the optical sections in panel A, the localization of the NODC-EGFP fusion protein coincides with the localization of the Golgi apparatus in the root hair cells.

3. Chitin Synthase Expression in Plant Cells Requires External Feeding with GlcNAc to Detect N-Acetylglucosamine in the Cell Walls.

Roots expressing a chimeric chitin synthase from *Neurospora crassa* were cultured as described above in the presence or absence of externally added N-acetylglucosamine. After careful washing, the roots were histochemically stained to detect N-acetylglucosamine. In FIG. 5, panel A (hairy roots with external GlcNAc feeding) numerous green fluorescent spots can be detected, whereas in panel B (hairy roots without external GlcNAc feeding) very few green fluorescent spots could be detected.

Example 3

Biochemical Demonstration of Chitin-Like Oligomers in the Cell Wall of *Arabidopsis* p35S::NODC Hairy Roots

*Arabidopsis thaliana* (Col-0) hairy roots transgenic for p35S:NODC-p35S:bar, obtained using T-DNA vector pTGK42 and control *Arabidopsis thaliana* (Col-0) hairy roots transgenic for p35S:bar obtained using pTCO192 (control) were analyzed for the presence of N-acetylglucosamine using the Morgan-Elson assay.

To this end, about 100 mg of hairy roots were harvested in about 20 μl, buffer (25 mM K-phosphate buffer pH 6.0) and ground with seasand, precipitated and the protein content of the extract determined (for standardization purposes). The supernatans was removed and the roots were resuspended in 100 μL buffer. 1 Unit cellulase (Cellulase "Onozuka R-10" from *Trichoderma viride* (Serva, Cat No 16419): 10 U/mL in buffer) or 1 Unit chitinase (Chitinase from *Serratia marcescens* (Sigma, Cat No C1650): 10 U/mL in buffer) or both were added to different samples and incubated for overnight at 25° C.

A Morgan-Elson assay to measure N-acetylglucosamine was performed on the samples the next morning. In the employed colorimetric method, which is based on the Morgan-Elson reaction, the N-acetyl-glucosamine reducing end is successively transformed into the chromogens I and II under the alkaline conditions at 100° C. Subsequent treatment with a mixture of concentrated HCl and concentrated sulfuric acid results in elimination of water yielding the chromogen III of the Morgan-Elson reaction. In the final step of the reaction, chromogen III is allowed to react with DMAB, p-dimethylaminobenzaldehyde (Ehrlich's reagent) to form a red-colored product the concentration of which can be determined by measuring the absorption at 585 nm.

UDP N-acetylglucosamine, and N-acetylglucosamine-1-phosphate fail to give the test unless they are previously hydrolyzed with acid. The nucleotides can be hydrolyzed by heating at 100° in 0.01 N acid for 15 min. but the sugar phosphate requires more rigorous conditions, e.g. 5 minutes at 100° in 0.1 N HCl.

The results are summarized in Table 2.

TABLE 2

| | OD585 values after Morgan-Elson assay | | | |
|---|---|---|---|---|
| Hairy root culture | Buffer | Cellulase | Chitinase | Cellulase Chitinase |
| Control | 0.070 | 0.100 | 0.117 | 0.157 |
| p35S:NODC | 0.056 | 0.096 | 0.100 | 0.252 |

From these results it can be concluded that chitin-like polymers are embedded in the cell wall.

Example 4

Analysis of Chito-Oligo and Monosaccharides in Plant Cell Wall Material Using HPTLC Cell walls of the *Arabidopsis* hairy roots of Example 1 (35S::NODC; 35S::NODC_EGFP) and 35S::bar control hairy roots were prepared according to the following protocol Preparation of Cell Walls Harvest hairy roots; remove most of the medium with a tissue Wash tissue with PBS buffer Put about 1 g of tissue in a tube Freeze with liquid nitrogen Grind tissue in a mortar Transfer grinded tissue in a funnel with cheese cloth Wash with a few liters of demineralized water Seal the cheese cloth and transfer to 500 mL bottle containing 500 mL ethanol Wash 15 minutes with 500 mL of ethanol, refresh ethanol and wash for another 15 minutes Replace ethanol by 250 mL ether and wash 15 minutes.

The remaining material is the 'cell wall material'. Dry and weigh the cell wall material and transfer it to a tube Extraction of Chito-Oligos from Cell Wall Material Add 300 μL MQ-water to 10 mg of cell wall material (use a 25 or 50 ml tube), boil 3 minutes and incubate for 2 hours at 80° C. (shake). The cell wall material can be digested with chitinase and β-N-Acetylglucosaminidase
Enzyme mixture: 0.5 U chitinase in 50 µL 125 mM
Na-phosphate—2 mM CaCl2—pH 6 (Chitinase Sigma
C7809 or C6137→digest (chito-oligo) saccharides very
quickly to N-acetylglucosamine. Chitinase BioLabs
P5206S→digest penta-N-acetylchitose (slowly) to di-
and tri- chito-oligos)
Add 100 µL enzyme mixture to about 5 mg cell wall material
Incubate overnight at 25° C.
The buffer can be separated from the cell wall material by centrifugation
After extraction, the buffer containing the chito-oligos is spotted on HPTLC plates (HPTLC plates NH2 (without fluorescent indicator) 10×20 cm (Merck, Art. 12572)) along with a mixture of chito-oligosaccharide standard solution in H2O. The standard solution comprises N-acetylglucosamine, chitobiose, chitotriose, chitotetraose and chitopentaose.
The following developing solvents can be used:
n-butanol (70): acetic acid (20): $H_2O$ (10) (Buffer D)
acetonitrile (76): $H_2O$ (24): 0.5% aqueous solution of boric acid (10) (Buffer A)
acetonitrile (10): isopropanol (67): 50 mM KCl (23) (Buffer B)
n-butanol (50): ethanol (30): $H_2O$ (20) (Buffer C)
Chromatography
Clean plates by developing with methanol
Spot 1(–2)µL of standard solutions (15 mm from bottom) and 1 to 5 µL of samples in bands of about 6 mm length
Develop plates in 'CAMAG Twin Through Chamber': 7 to 7.5 cm migration distance
Twin Through Chamber for: 10×10 cm plates→10 mL developing solution
20×10 cm plates→20 mL developing solution
Dry plates with ventilator
Heat plates at about 150° C. for 20 minutes (TLC plate heater)
Visualize sugars with UV (366 nm)
2D-Chromatography
Clean plates by developing with methanol
Spot 1 to 5 µL of samples in band of 3 mm: right angle of plate (15 mm from bottom and 15 mm from site)
Develop plates in the first direction in 'CAMAG Twin Through Chamber': 7 to 7.5 cm migration distance
Twin Through Chamber for: 10×10 cm plates→10 mL developing solution
Dry plates with ventilator
Develop plates in other direction
Dry plates with ventilator
Heat plates at about 150° C. for 20 minutes (TLC plate heater)
Visualize sugars with UV (366 nm)
FIG. 6 shows the results of one dimensional HPTLC, whereby the cell wall material was extracted but not further digested with chitinase. FIG. 7 shows the results of a two dimensional HPTLC after digestion with chitinase. No chito-oligomers can be detected in the control plants, but significant amounts of chito-oligomers is present in plants comprising an N-acetylglucosamine transferase gene.

Transgenic *Arabidopsis* plants were also generated using the chimeric genes described in Example 1. This material is more uniform than the hairy root cultures described above. Cell wall material was prepared, chito-oligosaccharides extracted as described and HPTLC performed in Buffer A as herein described. The results are shown in FIG. 8.

Cell wall material from transgenic 35S::NodC *Arabidopsis* shoots showed a high amount of chito-triose, estimated by comparison to the standard solutions to be about 5 µg/mg cell wall material or 0.01% of the fresh leaf material.

Example 5

Staining of Plant Cell Wall Material from *Arabidopsis* Hairy Root Cultures

*Arabidopsis* hairy root cultures were generated as in Example 1, cell wall material thereof was prepared as described in Example 5 and stored at –20° C. The cell wall material was stained with an anionic dye (Congo Red) or an amino reactive dye (Alexa Fluor 488 tetrafluorophenyl ester.
A. Congo Red Staining
Cell wall material stored at –20° C. from NODC hairy roots or control plants was rehydrated in acetate buffer pH 5 (50 mg cell wall material/tube)
The material was stained with 0.03% Congo red dissolved in acetate buffer pH5
The cell wall material was washed with acetate buffer pH5 and with PBS buffer for a few times
All the cell wall material was transferred to the wells of an 48 multiwell plate
Under standard illumination conditions, digital images were taken from individual wells and the mean gray value of the digital image was determined
Results: Sample 1:

|  | Mean | Min | Max | IntDen | Median |
|---|---|---|---|---|---|
| NodC | 89.390 | 76 | 126 | 3460186 | 89 |
| control | 97.761 | 83 | 136 | 3784246.000 | 97 |

Sample 2

|  | Mean | Min | Max | IntDen | Median |
|---|---|---|---|---|---|
| NodC | 101.548 | 86 | 130 | 3479355 | 101 |
| control | 108.109 | 90 | 139 | 3704154 | 108 |

Sample 3

|  | Mean | Min | Max | IntDen | Median |
|---|---|---|---|---|---|
| NodeC | 97.866 | 81 | 120 | 3650012 | 98 |
| control | 104.634 | 85 | 134 | 3902418 | 104 |

Cell wall material from hairy roots containing a chimeric NodC gene reproducibly stained more intense than cell wall material from control plants. The gray values of the cell wall material was about 5-10% lower than that of control plants.
B. Alexa Fluor 488 tetrafluorophenyl Ester Staining
Cell wall material stored at –20° C. from NODC hairy roots or control plants was rehydrated in PBS buffer pH 5 (50 mg cell wall material/tube), and treated with proteinase K (100 µg/ml) overnight at 56° C.
The material was intensively washed with PBS buffer and labelled with Alexa Fluor 488 tetrafluorophenyl ester. Alexa fluor 488 TFP ester is available as a kit (Alexa fluor 488 Monoclonal Antibody Labeling Kit (Molecular Probes, A-20181)
The stained material can be examined using fluorescence microscopy e.g. with Zeiss filter 38.

Cell wall material from hairy roots containing a chimeric NodC gene reproducibly stained more intense than cell wall material from control plants.

Example 6

Transgenic Cotton Plants

Transgenic cotton plants comprising a chimeric NODC gene as described in Example 1, or a chimeric NODC gene under control of the F285 fiber-selective promoter (as described in US2003/106097) are generated using the method as described in U.S. Pat. No. 6,483,013.

Fibers from these transgenic cotton plants are isolated, and used to produce yarns and fabrics with improved reactivity, such as improved dyeability.

Example 7

Cotton Fibers with Increased Reactivity

Transgenic cotton plants comprising a chimeric NodC coding region operably linked to a CaMV35S promoter were generated as described in Example 6. Mature cotton fibers were harvested from these plants and stained with Congo Red or reacted with WGA-Alexa fluor 555.

A. Congo Red Staining

Mature cotton fibers were harvested from transgenic cotton plants comprising a chimeric NodC gene, as well as from control plants not comprising a chimeric NodC gene. Lipids were removed from the fibers by washing with ethanol and ether. The cotton fibers were dryed.

Twenty-five mg of fibers were rehydrated in acetate buffer pH5 and stained with 0.03% Congo red dissolved in acetate buffer pH5. The cell wall material was washed with acetate buffer pH5 and with PBS buffer for a few times.

The stained fibers were analyzed by bright field microscopy and by fluorescence microscopy (Zeiss filter 18). Digital images of stained fibers in a 48 multiwell plate were also analyzed as described in Example 5A.

Under bright field microscopy, the cotton fibers harvested from the NodC transgenic cotton plants appeared more intense red than the cotton fibers from the non-transgenic plants. This difference was even more pronounced when analyzing the fibers under fluorescence microscopy.

The mean gray values obtained for the congo red stained cotton fibers from the transgenic NodC plants were also significantly lower than for the cotton fibers from non-transgenic plants, confirming the more intense staining by anionic dyes of the fibers of the transgenic cotton plants.

|  | Area | Mean | Min | Max | IntDen | Median |
|---|---|---|---|---|---|---|
| NodC | 38958 | 81.388 | 72 | 179 | 3170716 | 80 |
| control | 38958 | 86.558 | 79 | 160 | 3372108 | 85 |

The difference in staining was maintained and even intensified when fibers were treated for at least one hour with hot NaOH (60% at 80° C.). This treatment removes proteins, pectic substances and waxes, and is capable of deacetylating the chito-oligomers.

The intensified congo-red stain was moreover distributed evenly in the cell wall as can be observed when virtual microscopic sections of individual fiber cells were made.

B. WGA-Alexa 555 Staining

Detection of N-acetylglucosamine oligomers in cotton fibers from transgenic NodC plants was done essentially as described in Example 2. Cotton fibers do not need to be dehydrated or permeabilized. Instead, lipids and waxes were removed by treating the fibers for 3 times 10 minutes in a chloroform: methanol mixture (1:1), follow by twice a treatment of 10 minutes in acetone and twice 5 minutes in ether. The fibers were allowed to air dry.

Fibers were stained with either WGA-Alexa555, WGA-Alexa488 or WGA-tetramethylrhodamine.

The fibers were placed in blocking solution (150 mM NaCL, 10 mM sodiumphosphate buffer pH 7.4; 0.1% Tween 20 and 1% bovine serum albumin) and incubated for one hour. Thereafter, the buffer was replaced by the same buffer containing WGA-fluorochrome and incubated for 4 hrs. The WGA-fluorochrome solution was replaced by blocking solution, washed 10 minutes, followed by 3 times 10 min washing with blocking solution without BSA, and 2 times 5 min washing with blocking solution without BSA and without Tween. The stained fibers were mounted on a microscope slide and evaluated by means of fluorescence microscopy (Axioplan 2 (Zeiss, Jena, Germany) using Filterset 38 (exitation: BP470/40; emission: BP525/50) for Alexa fluor 488 conjugate or Filterset (exitation: BP546/12; emission: BP575-640) for Alexa fluor 555 or tetramethylrhodamine conjugate.

Whereas no specific fluorescence could be detected in cotton fibers from non-transgenic plants, a bright fluorescence was detectable in cotton fibers from chimeric NodC gene comprising cotton plants (see FIG. 9). Virtual microscopic sections of the cotton fibers indicated that the WGA-fluor555 is evenly distributed throughout the secondary cell wall of the cotton fiber cells.

Example 9

Reactivity of Cell Walls of *Arabidopsis* Hairy Roots Comprising a Chitin Synthase from *Neurospora crassa* with Golgi-Targeting Signal Using standard recombinant DNA techniques, a plant expressible N-acetylglucosamine transferase comprising a heterologous Golgi-targeting signal sequence, was constructed containing the following operably linked DNA fragments:
a 35S promoter region from CaMV
a DNA fragment coding for an untranslated leader sequence (5'Cab22L)
a DNA fragment coding for the 35 N-terminal amino acids of β-1,2-xylosyltransferase from *Arabidopsis thaliana*
a DNA fragment coding for CHS2 (chitin synthase) of *Neurospora crassa* cloned in frame with the previous DNA fragment
a transcription termination and polyadenylation signal from the 35S transcript of CaMV (3' 35S)

The chimeric gene was introduced between T-DNA borders of a T-DNA vector together with a chimeric bar gene providing resistance to phosphinotricin. The resulting T-DNA vector was named pTDBI37. The sequence of the T-DNA of this vector is provided in SEQ ID No 13.

The T-DNA vectors were introduced in *A. tumefaciens* and used to generate hairy root cultures as described in Example 1.

N-acetylglucosamine oligomers could be detected in the cell wall of the hairy root cultures after incubation with chitine binding domain conjugated to fluorescein, by fluorescence microscopy.

N-acetylglucosamine oligomers could also be detected in the cell wall of the hairy root cultures using WGA-Alexa555 as described in Example 2. In addition, fluorescence could also be observed associated with globules in the cytoplasm, corresponding to the Golgi-apparatus.

Example 9

Determination of the Nitrogen Content of Cotton Fibers

Mature cotton balls were harvested from the transgenic cotton plants of Example 7. From each ball, 20 mg of cleaned fibers were assayed. To this end, lipids and waxes were removed from the fibers by washing 3 times 20 minutes in a chloroform:methanol (1:1) mixture; 2 times 20 minutes in acetone; 2 times 5 minutes in ether and allowed to air dry.

The total nitrogen at the surface of fibers was measured using 'Total Nitrogen' analysis kit and C214 Multiparameter Bench Photometer of HANNA Instruments (Rhode Island, USA).

The following results were obtained:

|  | Wild type | Transgenic |
| --- | --- | --- |
| Mean | 56 mg/L N | 85 mg/L N |
| Number of cotton balls | 9 | 10 |
| Standard error | 2.6 mg/L N | 5.1 mg/L N |
| t-test ($\alpha = 0.05$) | | |
| P two tailed | $2.2 \times 10^{-4}$ | |

The fibers from the cotton balls from the transgenic lines contained statistically significant more nitrogen at the surface than the fibers from wild type cotton balls.

Example 10

Fiber Specific Expression of a Chitin Synthase in Cotton

Using standard recombinant DNA techniques, a plant expressible N-acetylglucosamine transferase comprising a heterologous Golgi-targeting signal sequence, was constructed containing the following operably linked DNA fragments:

a fiber specific promoter region from cotton a DNA fragment coding for an untranslated leader sequence (5'Cab22L)

a DNA fragment coding for the 35 N-terminal amino acids of β-1,2-xylosyltransferase from *Arabidopsis thaliana* a DNA fragment coding for CHS2 (chitin synthase) of *Neurospora crassa* cloned in frame with the previous DNA fragment a transcription termination and polyadenylation signal from the 35S transcript of CaMV (3' 35S)

The chimeric gene was introduced between T-DNA borders of a T-DNA vector together with a chimeric bar gene providing resistance to phosphinotricin. The resulting T-DNA vector was named pTDBI50. The sequence of the T-DNA of this vector is provided in SEQ ID No 14.

The T-DNA vectors are introduced in *A. tumefaciens* and used to generate transgenic cotton. Fibers isolated from cotton balls of transgenic plants have an increased amount of N-acetylglucosamine oligomers, more or less evenly distributed throughout the cell wall.

The invention claimed is:

1. A cotton fiber comprising a plant cell wall comprising positively charged oligosaccharides embedded in the cellulose of said cell wall, wherein said oligosaccharide comprises chito-oligosaccharides in a concentration of at least 0.1 µg/mg cell wall material.

2. A yarn or a fabric comprising the cotton fiber of claim 1.

3. The cotton fiber of claim 1, wherein said positively charged oligosaccharides are oligo-N acetylglucosamines or oligo-glucosamines.

4. The cotton fiber of claim 3, wherein said oligo-N acetylglucosamines or oligo-glucosamines have a polymerization degree between 3 and 10.

5. The cotton fiber of claim 4, wherein said polymerization degree is between 3 and 5.

6. The cotton fiber of claim 3, wherein the content of said N-acetylglucosamine oligomers or chitin or glucosamine is increased by at least 5% in staining by congo-red as compared to control cell wall material from a non transgenic cotton fiber cell.

7. The cotton fiber of claim 1, wherein said oligosaccharide comprises chito-oligosaccharides in a concentration of at least 1 µg/mg cell wall material.

8. The cotton fiber of claim 1, wherein said oligosaccharide comprises chito-oligosaccharides in a concentration of at least 5 µg/mg cell wall material.

9. A yarn or a fabric comprising the cotton fiber of claim 7.

10. A yarn or a fabric comprising the cotton fiber of claim 8.

* * * * *

SEQUENCE LISTING

```
<160> NUMBER OF SEQ ID NOS: 30

<210> SEQ ID NO 1
<211> LENGTH: 395
<212> TYPE: PRT
<213> ORGANISM: Azorhizobium caulinodans

<400> SEQUENCE: 1

Met Ser Val Val Asp Val Ile Gly Leu Leu Ala Thr Ala Ala Tyr Val
1               5                   10                  15

Thr Leu Ala Ser Ala Tyr Lys Val Val Gln Phe Ile Asn Val Ser Ser
            20                  25                  30

Val Thr Asp Val Ala Gly Leu Glu Ser Asp Ala Leu Pro Leu Thr Pro
        35                  40                  45

Arg Val Asp Val Ile Val Pro Thr Phe Asn Glu Asn Ser Ser Thr Leu
    50                  55                  60

Leu Glu Cys Val Ala Ser Ile Cys Ala Gln Asp Tyr Arg Gly Pro Ile
65                  70                  75                  80

Thr Ile Val Val Val Asp Asp Gly Ser Thr Asn Lys Thr Ser Phe His
                85                  90                  95

Ala Val Cys Asp Lys Tyr Ala Ser Asp Glu Arg Phe Ile Phe Val Glu
            100                 105                 110
```

```
Leu Asp Gln Asn Lys Gly Thr Ala Ala Gln Met Glu Ala Ile Arg Arg
            115                 120                 125

Thr Asp Gly Asp Leu Ile Leu Asn Val Asp Ser Asp Thr Val Ile Asp
        130                 135                 140

Lys Asp Val Val Thr Lys Leu Ala Ser Ser Met Arg Ala Pro Asn Val
145                 150                 155                 160

Gly Gly Val Met Gly Gln Leu Val Ala Lys Asn Arg Glu Arg Ser Trp
                165                 170                 175

Leu Thr Arg Leu Ile Asp Met Glu Tyr Trp Leu Ala Cys Asn Glu Glu
            180                 185                 190

Arg Ile Ala Gln Ser Arg Phe Gly Ser Val Met Cys Cys Cys Gly Pro
        195                 200                 205

Cys Ala Met Tyr Arg Arg Ser Ala Ile Thr Pro Leu Leu Ala Glu Tyr
    210                 215                 220

Glu His Gln Thr Phe Leu Gly Arg Pro Ser Asn Phe Gly Glu Asp Arg
225                 230                 235                 240

His Leu Thr Ile Leu Met Leu Lys Ala Gly Phe Arg Thr Gly Tyr Val
                245                 250                 255

Pro Ser Ala Val Ala Arg Thr Leu Val Pro Asp Gly Ser Pro Tyr Leu
            260                 265                 270

Arg Gln Gln Leu Arg Trp Ala Arg Ser Thr Tyr Arg Asp Thr Ala Leu
        275                 280                 285

Ala Leu Arg Ile Lys Lys Asn Leu Ser Lys Tyr Ile Thr Phe Glu Ile
    290                 295                 300

Cys Ala Gln Asn Leu Gly Thr Ala Leu Leu Val Met Thr Met Ile
305                 310                 315                 320

Ser Leu Ser Leu Thr Thr Ser Gly Ser Gln Thr Pro Val Ile Ile Leu
                325                 330                 335

Gly Val Val Gly Met Ser Ile Ile Arg Cys Cys Ser Val Ala Leu
            340                 345                 350

Ile Ala Lys Asp Phe Arg Phe Leu Tyr Phe Ile Val His Ser Ala Leu
        355                 360                 365

Asn Val Leu Ile Leu Thr Pro Leu Lys Leu Tyr Ala Leu Leu Thr Ile
    370                 375                 380

Arg Asp Ser Arg Trp Leu Ser Arg Glu Ser Ser
385                 390                 395

<210> SEQ ID NO 2
<211> LENGTH: 485
<212> TYPE: PRT
<213> ORGANISM: Bradyrhizobium japonicum

<400> SEQUENCE: 2

Met Asp Leu Leu Ala Thr Thr Ser Ala Ala Ala Val Ser Ser Tyr Ala
1               5                   10                  15

Leu Leu Ser Thr Ile Tyr Lys Ser Val Gln Ala Leu Tyr Ala Gln Pro
                20                  25                  30

Ala Ile Asn Ser Ser Leu Asp Asn Leu Gly Gln Ala Glu Val Val Val
            35                  40                  45

Pro Ala Val Asp Val Ile Val Pro Cys Phe Asn Glu Asn Pro Asn Thr
        50                  55                  60

Leu Ala Glu Cys Leu Glu Ser Ile Ala Ser Gln Asp Tyr Ala Gly Lys
65                  70                  75                  80

Met Gln Val Tyr Val Val Asp Asp Gly Ser Ala Asn Arg Asp Val Val
                85                  90                  95
```

```
Ala Pro Val His Arg Ile Tyr Ala Ser Asp Pro Arg Phe Ser Phe Ile
            100                 105                 110

Leu Leu Ala Asn Asn Val Gly Lys Arg Lys Ala Gln Ile Ala Ala Ile
            115                 120                 125

Arg Ser Ser Gly Asp Leu Val Leu Asn Val Asp Ser Asp Thr Ile
            130                 135                 140

Leu Ala Ala Asp Val Val Thr Lys Leu Val Lys Met His Asp Pro
145                 150                 155                 160

Gly Ile Gly Ala Ala Met Gly Gln Leu Ile Ala Ser Asn Arg Asn Gln
                    165                 170                 175

Thr Trp Leu Thr Arg Leu Ile Asp Met Glu Tyr Trp Leu Ala Cys Asn
            180                 185                 190

Glu Glu Arg Ala Ala Gln Ala Arg Phe Gly Ala Val Met Cys Cys Cys
            195                 200                 205

Gly Pro Cys Ala Met Tyr Arg Arg Ser Ala Leu Ala Leu Leu Leu Asp
            210                 215                 220

Gln Tyr Glu Ala Gln Phe Phe Arg Gly Lys Pro Ser Asp Phe Gly Glu
225                 230                 235                 240

Asp Arg His Leu Thr Ile Leu Met Leu Lys Ala Gly Phe Arg Thr Glu
            245                 250                 255

Tyr Val Pro Asp Ala Ile Ala Ala Thr Val Val Pro His Ser Leu Arg
            260                 265                 270

Pro Tyr Leu Arg Gln Gln Leu Arg Trp Ala Arg Ser Thr Phe Arg Asp
            275                 280                 285

Thr Phe Leu Ala Trp Arg Leu Leu Pro Glu Leu Asp Gly Tyr Leu Thr
            290                 295                 300

Leu Asp Val Ile Gly Gln Asn Leu Gly Pro Leu Leu Ala Ile Ser
305                 310                 315                 320

Ser Leu Ala Ala Leu Ala Gln Leu Leu Ile Asp Gly Ser Ile Pro Trp
            325                 330                 335

Trp Thr Gly Leu Thr Ile Ala Ala Met Thr Thr Val Arg Cys Cys Val
            340                 345                 350

Ala Ala Leu Arg Ala Arg Glu Leu Arg Phe Ile Gly Phe Ser Leu His
            355                 360                 365

Thr Pro Ile Asn Ile Cys Leu Leu Leu Pro Leu Lys Ala Tyr Ala Leu
            370                 375                 380

Cys Thr Leu Ser Asn Ser Asp Trp Leu Ser Arg Lys Val Thr Asp Met
385                 390                 395                 400

Pro Thr Glu Glu Gly Lys Gln Pro Val Ile Leu His Pro Asn Ala Gly
                    405                 410                 415

Arg Ser Pro Ala Gly Val Gly Gly Arg Leu Leu Leu Phe Val Arg Arg
            420                 425                 430

Arg Tyr Arg Ser Leu His Arg Ala Trp Arg Arg Arg Val Phe Pro
            435                 440                 445

Val Ala Ile Val Arg Leu Ser Thr Asn Lys Trp Ser Ala Asp Asp Ser
            450                 455                 460

Gly Arg Lys Pro Ser Val Ile Arg Ala Arg Val Gly Cys Arg Arg Pro
465                 470                 475                 480

Val Ala Pro Arg His
            485

<210> SEQ ID NO 3
<211> LENGTH: 433
```

<212> TYPE: PRT
<213> ORGANISM: Rhizobium galegae

<400> SEQUENCE: 3

```
Met Thr Leu Leu Glu Thr Ile Gly Ile Ala Ala Val Thr Leu His Ala
1               5                   10                  15

Leu Leu Ser Ala Ile Tyr Lys Ser Met Gln Ala Phe Tyr Ala Arg Lys
            20                  25                  30

Ala Ser Gly Ser Gln Pro Arg Ser Lys Asp Ile Asp Pro Ala Ala Leu
        35                  40                  45

Pro Ser Val Asp Ile Ile Val Pro Cys Phe Asn Glu Asp Pro Ala Ile
    50                  55                  60

Leu Ser Ala Cys Leu Ser Ser Leu Ala Gly Gln Asp Tyr Gly Gly Lys
65                  70                  75                  80

Leu Arg Ile Tyr Met Val Asp Asp Gly Ser Cys Asn Arg Glu Ala Ile
                85                  90                  95

Leu Pro Val His Asp Phe Tyr Thr Ser Asp Pro Arg Phe Glu Phe Leu
            100                 105                 110

Leu Leu Ser Lys Asn Val Gly Lys Arg Lys Ala Gln Ile Ala Ala Ile
        115                 120                 125

Glu Arg Ser Cys Gly Asp Leu Ile Leu Asn Val Asp Ser Asp Thr Ser
    130                 135                 140

Ile Ala Ser Asp Val Val Thr Leu Leu Val Glu Lys Met Arg Asp Ser
145                 150                 155                 160

Asp Val Gly Ala Ala Met Gly Gln Leu Lys Ala Ser Asn Arg Asp Lys
                165                 170                 175

Asn Leu Leu Thr Arg Leu Ile Asp Met Glu Tyr Trp Leu Ala Cys Asn
            180                 185                 190

Asp Glu Arg Ala Ala Gln Ala Arg Phe Gly Ala Val Met Cys Cys Cys
        195                 200                 205

Gly Pro Cys Ala Met Tyr Arg Arg Ser Ala Leu Leu Leu Leu Leu Asp
    210                 215                 220

Gln Tyr Gln Thr Gln Leu Tyr Arg Gly Lys Pro Ser Asp Phe Gly Glu
225                 230                 235                 240

Asp Arg His Leu Thr Ile Leu Met Leu Ser Ala Gly Phe Arg Thr Glu
                245                 250                 255

Tyr Val Pro Glu Ala Ile Ala Lys Thr Val Val Pro Arg Met Gly
            260                 265                 270

Ser Tyr Leu Arg Gln Gln Leu Arg Trp Ala Arg Ser Thr Phe Arg Asp
        275                 280                 285

Thr Leu Leu Ala Leu Pro Leu Pro Ser His Asn Arg Phe Leu Thr
290                 295                 300

Leu Asp Ala Ile His Gln Asn Ile Gly Pro Leu Leu Ala Val Ser
305                 310                 315                 320

Ser Ala Thr Gly Ile Thr Gln Phe Ile Leu Thr Ala Thr Val Pro Gly
                325                 330                 335

Trp Thr Ile Ile Ile Ile Ala Ser Met Thr Met Val Arg Cys Ser Val
            340                 345                 350

Ala Ala Tyr Arg Ser Arg Gln Ile Arg Phe Leu Ala Phe Ser Leu His
        355                 360                 365

Thr Leu Ile Asn Leu Phe Met Leu Ile Pro Leu Lys Gly Phe Ala Leu
370                 375                 380

Leu Thr Leu Ser Asn Ser Asp Trp Leu Ser Arg Gly Ser Thr Thr Asp
385                 390                 395                 400
```

```
Gly Pro Ala Ile Ala Glu Ser Asn Ala Ala Ser Asn Glu Ala Glu Ile
                405                 410                 415

Val Ala Ser Ala Ser Pro Phe Gly Gly Thr Ser Trp Arg Phe Arg
            420                 425                 430

Arg

<210> SEQ ID NO 4
<211> LENGTH: 424
<212> TYPE: PRT
<213> ORGANISM: Rhizobium leguminosarum

<400> SEQUENCE: 4

Met Thr Leu Leu Ala Thr Thr Ser Ile Ala Ile Ser Leu Tyr Ala
1               5                   10                  15

Met Leu Ser Thr Val Tyr Lys Ser Ala Gln Val Phe His Ala Arg Arg
            20                  25                  30

Thr Thr Ile Ser Thr Thr Pro Ala Lys Asp Ile Glu Thr Asn Pro Val
            35                  40                  45

Pro Ser Val Asp Val Ile Val Pro Cys Phe Asn Glu Asp Pro Ile Val
50                  55                  60

Leu Ser Glu Cys Leu Ala Ser Leu Ala Glu Gln Asp Tyr Ala Gly Lys
65                  70                  75                  80

Leu Arg Ile Tyr Val Val Asp Asp Gly Ser Lys Asn Arg Asp Ala Val
                85                  90                  95

Val Ala Gln Arg Ala Ala Tyr Ala Asp Asp Glu Arg Phe Asn Phe Thr
            100                 105                 110

Ile Leu Pro Lys Asn Val Gly Lys Arg Lys Ala Ile Ala Ala Ile Thr
            115                 120                 125

Gln Ser Ser Gly Asp Leu Ile Leu Asn Val Asp Ser Asp Thr Thr Ile
130                 135                 140

Ala Pro Asp Val Val Ser Lys Leu Ala His Lys Met Arg Asp Pro Ala
145                 150                 155                 160

Val Gly Ala Ala Met Gly Gln Met Lys Ala Ser Asn Gln Ala Asp Thr
                165                 170                 175

Trp Leu Thr Arg Leu Ile Asp Met Glu Tyr Trp Leu Ala Cys Asn Glu
            180                 185                 190

Glu Arg Ala Ala Gln Ala Arg Phe Gly Ala Val Met Cys Cys Cys Gly
            195                 200                 205

Pro Cys Ala Met Tyr Arg Arg Ser Ala Met Leu Ser Leu Leu Asp Gln
210                 215                 220

Tyr Glu Thr Gln Leu Tyr Arg Gly Lys Pro Ser Asp Phe Gly Glu Asp
225                 230                 235                 240

Arg His Leu Thr Ile Leu Met Leu Ser Ala Gly Phe Arg Thr Glu Tyr
                245                 250                 255

Val Pro Ser Ala Ile Ala Ala Thr Val Val Pro Asp Thr Met Gly Val
            260                 265                 270

Tyr Leu Arg Gln Gln Leu Arg Trp Ala Arg Ser Thr Phe Arg Asp Thr
            275                 280                 285

Leu Leu Ala Leu Pro Val Leu Pro Gly Leu Asp Arg Tyr Leu Thr Leu
290                 295                 300

Asp Ala Ile Gly Gln Asn Val Gly Leu Leu Leu Ala Leu Ser Val
305                 310                 315                 320

Leu Thr Gly Ile Gly Gln Phe Ala Leu Thr Ala Thr Leu Pro Trp Trp
                325                 330                 335
```

```
Thr Ile Leu Val Ile Gly Ser Met Thr Leu Val Arg Cys Ser Val Ala
                340                 345                 350

Ala Tyr Arg Ala Arg Glu Leu Arg Phe Leu Gly Phe Ala Leu His Thr
            355                 360                 365

Leu Val Asn Ile Phe Leu Leu Ile Pro Leu Lys Ala Tyr Ala Leu Cys
        370                 375                 380

Thr Leu Ser Asn Ser Asp Trp Leu Ser Arg Gly Ser Val Ala Ile Ala
385                 390                 395                 400

Pro Thr Val Gly Gln Gln Gly Ala Thr Lys Met Pro Gly Arg Ala Thr
                405                 410                 415

Ser Glu Ile Ala Tyr Ser Gly Glu
            420

<210> SEQ ID NO 5
<211> LENGTH: 426
<212> TYPE: PRT
<213> ORGANISM: Rhizobium meliloti

<400> SEQUENCE: 5

Met Tyr Leu Leu Asp Thr Thr Ser Thr Ala Ala Ile Ser Ile Tyr Ala
1               5                   10                  15

Leu Leu Leu Thr Ala Tyr Arg Ser Met Gln Val Leu Tyr Ala Arg Pro
            20                  25                  30

Ile Asp Gly Pro Ala Val Ala Ala Glu Pro Val Glu Thr Arg Pro Leu
        35                  40                  45

Pro Ala Val Asp Val Ile Val Pro Ser Phe Asn Glu Asp Pro Gly Ile
50                  55                  60

Leu Ser Ala Cys Leu Ala Ser Ile Ala Asp Gln Asp Tyr Pro Gly Glu
65                  70                  75                  80

Leu Arg Val Tyr Val Val Asp Asp Gly Ser Arg Asn Arg Glu Ala Ile
                85                  90                  95

Val Arg Val Arg Ala Phe Tyr Ser Arg Asp Pro Arg Phe Ser Phe Ile
            100                 105                 110

Leu Leu Pro Glu Asn Val Gly Lys Arg Lys Ala Gln Ile Ala Ala Ile
        115                 120                 125

Gly Gln Ser Ser Gly Asp Leu Val Leu Asn Val Asp Ser Asp Ser Thr
130                 135                 140

Ile Ala Phe Asp Val Val Ser Lys Leu Ala Ser Lys Met Arg Asp Pro
145                 150                 155                 160

Glu Val Gly Ala Val Met Gly Gln Leu Thr Ala Ser Asn Ser Gly Asp
                165                 170                 175

Thr Trp Leu Thr Lys Leu Ile Asp Met Glu Tyr Trp Leu Ala Cys Asn
            180                 185                 190

Glu Glu Arg Ala Ala Gln Ser Arg Phe Gly Ala Val Met Cys Cys Cys
        195                 200                 205

Gly Pro Cys Ala Met Tyr Arg Arg Ser Ala Leu Ala Ser Leu Leu Asp
210                 215                 220

Gln Tyr Glu Thr Gln Leu Phe Arg Gly Lys Pro Ser Asp Phe Gly Glu
225                 230                 235                 240

Asp Arg His Leu Thr Ile Leu Met Leu Lys Ala Gly Phe Arg Thr Glu
                245                 250                 255

Tyr Val Pro Asp Ala Ile Val Ala Thr Val Val Pro Asp Thr Leu Lys
            260                 265                 270

Pro Tyr Leu Arg Gln Gln Leu Arg Trp Ala Arg Ser Thr Phe Arg Asp
```

```
                275                 280                 285
Thr Phe Leu Ala Leu Pro Leu Leu Arg Gly Leu Ser Pro Phe Leu Ala
290                 295                 300

Phe Asp Ala Val Gly Gln Asn Ile Gly Gln Leu Leu Leu Ala Leu Ser
305                 310                 315                 320

Val Val Thr Gly Leu Ala His Leu Ile Met Thr Ala Thr Val Pro Trp
                325                 330                 335

Trp Thr Ile Leu Ile Ile Ala Cys Met Thr Ile Ile Arg Cys Ser Val
                340                 345                 350

Val Ala Leu His Ala Arg Gln Leu Arg Phe Leu Gly Phe Val Leu His
                355                 360                 365

Thr Pro Ile Asn Leu Phe Leu Ile Leu Pro Leu Lys Ala Tyr Ala Leu
370                 375                 380

Cys Thr Leu Ser Asn Ser Asp Trp Leu Ser Arg Tyr Ser Ala Pro Glu
385                 390                 395                 400

Val Pro Val Ser Gly Gly Lys Gln Thr Pro Ile Gln Thr Ser Gly Arg
                405                 410                 415

Val Thr Pro Asp Cys Thr Cys Ser Gly Glu
                420                 425

<210> SEQ ID NO 6
<211> LENGTH: 452
<212> TYPE: PRT
<213> ORGANISM: Rhizobium tropici

<400> SEQUENCE: 6

Met Asn Leu Leu Asp Ala Thr Ser Thr Ala Ala Ile Ser Leu Tyr Ala
1               5                   10                  15

Met Leu Ser Thr Ala Tyr Lys Ser Met Gln Val Val Tyr Ala Arg Pro
                20                  25                  30

Ile Glu Glu Pro Ser Thr Ser Ala Glu Pro Ile Ala Ser Ala Gln Trp
                35                  40                  45

Pro Ser Val Asp Val Ile Ile Pro Ser Phe Asn Glu Asp Pro Gly Thr
50                  55                  60

Leu Trp Asp Cys Leu Glu Ser Ile Ala His Glu Glu Tyr Ala Gly Asp
65                  70                  75                  80

Leu Asn Val Tyr Val Val Asp Asp Gly Ser Ser Asn Arg Asp Ala Ile
                85                  90                  95

Thr Pro Val His Thr Ala Phe Ala Arg Asp Pro Arg Phe Thr Phe Ile
                100                 105                 110

Leu Leu Arg Lys Asn Val Gly Lys Arg Lys Ala Gln Ile Ala Ala Ile
                115                 120                 125

Arg Arg Ser Ser Gly Asp Leu Val Leu Asn Val Asp Ser Asp Thr Ile
130                 135                 140

Leu Ala Pro Asp Val Val Lys Leu Ala Leu Lys Met Gln Asp Pro
145                 150                 155                 160

Ala Ile Gly Ala Ala Met Gly Gln Leu Ala Ser Asn Arg His Glu
                165                 170                 175

Thr Trp Leu Thr Arg Leu Ile Asp Met Glu Tyr Trp Leu Ala Cys Asn
                180                 185                 190

Glu Glu Arg Ala Ala Gln Ala Arg Phe Gly Ala Val Met Cys Cys Cys
                195                 200                 205

Gly Pro Cys Ala Met Tyr Arg Arg Thr Ala Leu Thr Met Leu Leu Asp
210                 215                 220
```

```
Gln Tyr Glu Thr Gln Met Phe Arg Gly Lys Arg Ser Asp Phe Gly Glu
225                 230                 235                 240

Asp Arg His Leu Thr Ile Leu Met Leu Lys Ala Gly Phe Arg Thr Glu
            245                 250                 255

Tyr Val Pro Thr Ala Ile Ala Ala Thr Val Val Pro Asn Lys Leu Arg
        260                 265                 270

Pro Tyr Leu Arg Gln Gln Leu Arg Trp Ala Arg Ser Thr Phe Arg Asp
    275                 280                 285

Thr Leu Leu Ala Met Asn Leu Leu Pro Gly Leu Asp Arg Phe Leu Thr
290                 295                 300

Leu Asp Val Ile Gly Gln Asn Leu Gly Pro Leu Leu Ala Leu Ser
305                 310                 315                 320

Val Leu Thr Gly Leu Ala Gln Phe Ala Leu Thr Gly Thr Val Pro Trp
            325                 330                 335

Trp Thr Cys Leu Met Ile Ala Ser Met Thr Met Ile Arg Cys Ser Val
        340                 345                 350

Ala Ala Val Arg Ala Arg Gln Phe Arg Phe Ile Gly Phe Ser Leu His
    355                 360                 365

Thr Phe Ile Asn Ile Phe Phe Leu Leu Pro Leu Lys Ala Tyr Ala Leu
370                 375                 380

Cys Thr Leu Ser Asn Ser Asp Trp Leu Ser Arg Gly Ser Ala Ala Lys
385                 390                 395                 400

Ala Thr Gly Lys Gly Lys Leu Asp Ala Ile Gln Asp Pro Val Ala
            405                 410                 415

Ala Ser Ser Pro Arg Glu Ser Gln Glu Asn Glu Ala Pro Leu Arg Arg
        420                 425                 430

His Asn Leu Ala Arg Asp Ala Thr Arg Ser Met Ala Tyr Asp Gly Ile
    435                 440                 445

Cys Thr Asp Gln
450

<210> SEQ ID NO 7
<211> LENGTH: 428
<212> TYPE: PRT
<213> ORGANISM: Rhizobium leguminosarum

<400> SEQUENCE: 7

Met Thr Met Leu Asp Thr Thr Ser Thr Val Ala Val Ser Leu Tyr Ala
1               5                   10                  15

Leu Leu Ser Thr Ala Tyr Lys Ser Met Gln Ala Val Tyr Ser Leu Pro
            20                  25                  30

Thr Asp Val Ser Leu Ala Ser His Gly Leu Gly Gly Phe Asp Glu Leu
        35                  40                  45

Pro Ser Val Asp Val Ile Val Pro Ser Phe Asn Glu Asp Pro Arg Thr
    50                  55                  60

Leu Ser Glu Cys Leu Ala Ser Ile Ala Gly Gln Glu Tyr Gly Gly Arg
65                  70                  75                  80

Leu Gln Val Tyr Leu Val Asp Asp Gly Ser Glu Asn Arg Glu Ala Leu
            85                  90                  95

Arg Leu Val His Glu Ala Phe Ala Arg Asp Pro Arg Phe Asn Ile Leu
        100                 105                 110

Leu Leu Pro Gln Asn Val Gly Lys Arg Lys Ala Gln Asp Arg Cys Asp
    115                 120                 125

Gln Arg Ser Ala Gly Asp Met Val Leu Asn Val Asp Ser Asp Thr Ile
130                 135                 140
```

```
Leu Ala Ser Asp Val Ile Arg Lys Leu Val Pro Lys Asn Ala Arg Val
145                 150                 155                 160

Ala Val Gly Arg Met Gly Gln Leu Thr Gly Pro Gln Pro Lys Arg Gln
                165                 170                 175

Leu Ala Asp Pro Phe Asp Met Glu Tyr Trp Leu Ala Cys Asn Glu
            180                 185                 190

Glu Arg Ser Gln Gln Ala Arg Phe Gly Cys Val Met Phe Cys Ser Gly
                195                 200                 205

Ser Cys Val Met Tyr Arg Leu Val Ser Ala Ser Leu Leu Asp Gln Tyr
        210                 215                 220

Asp Ala Gln Tyr Phe Arg Lys Gln Arg Phe Gly Glu Ile Asp Ile His
225                 230                 235                 240

Leu Ser His Ala Glu Gly Ser Phe Arg Thr Glu Tyr Arg Pro Ser Ala
                245                 250                 255

His Ala Ala Thr Val Val Pro Asn Lys Leu Gly Pro Tyr Leu Gly Gln
            260                 265                 270

Gln Leu Arg Trp Ala Arg Ser Thr Phe Arg Thr Leu Leu Gly Ala
                275                 280                 285

Pro Leu Pro Asn Leu Asn Arg Phe Leu Met Leu Asp Val Val Gly Gln
            290                 295                 300

Asn Leu Gly Pro Leu Leu Asp His Ser Val Leu Thr Gly Leu Ala
305                 310                 315                 320

Gln Leu Ala Leu Thr Gly Thr Ala Pro Trp Leu Ala Ala Leu Met Ile
                325                 330                 335

Val Ala Met Thr Ile Asp Arg Cys Ser Val Val Ala Leu Arg Ala Arg
                340                 345                 350

Gln Leu Arg Phe Leu Gly Phe Ser Leu His Thr Phe Ile Asn Ile Phe
                355                 360                 365

Leu Leu Leu Pro Leu Lys Ala Tyr Ala Leu Cys Thr Leu Ser Asn Ile
        370                 375                 380

Ala Trp Leu Ser Ser Leu Leu Cys Trp Gln Leu Glu Ser Thr Ser Thr
385                 390                 395                 400

Ala Asp Ala Arg Thr Thr Glu Cys Ser Asp Met Arg Thr Ala Ser Lys
                405                 410                 415

Leu Ser Pro Pro Ser Cys Gln Ala Asn Asp Val
            420                 425

<210> SEQ ID NO 8
<211> LENGTH: 450
<212> TYPE: PRT
<213> ORGANISM: Rhizobium sp.

<400> SEQUENCE: 8

Met Asp Leu Leu Thr Thr Thr Ser Thr Val Ala Val Ala Cys Tyr Ala
1               5                   10                  15

Leu Leu Ser Thr Val Tyr Lys Gly Met Gln Ala Val Tyr Ser Leu Pro
                20                  25                  30

Pro Thr Val Ala Pro Ala Ser Glu Asp Leu Val Gly Ser Asp Leu Trp
            35                  40                  45

Pro Ser Val Asp Val Ile Ile Pro Cys Tyr Asn Glu Gly Pro Leu Thr
        50                  55                  60

Leu Ser Ala Cys Leu Asp Ser Ile Ala Asn Gln Glu Tyr Ala Gly Lys
65                  70                  75                  80

Leu Arg Val Tyr Val Val Asp Asp Gly Ser Gly Asn Arg Asp Ala Val
```

85                  90                  95
        Ile Pro Ile His Asp Asn Tyr Ala Gly Asp Pro Arg Phe Asp Phe Ile
                    100                 105                 110

Leu Leu Pro Glu Asn Val Gly Lys Arg Lys Ala Gln Ile Ala Ala Ile
                    115                 120                 125

Arg Arg Ser Ser Gly Asp Leu Val Leu Asn Val Asp Ser Asp Thr Thr
                    130                 135                 140

Leu Ala Ser Asp Val Ile Arg Lys Leu Ala Arg Lys Met Gln Asp Pro
        145                 150                 155                 160

Ala Ile Gly Ala Ala Met Gly Gln Leu Thr Ala Ser Asn Arg Ser Asp
                    165                 170                 175

Thr Trp Leu Thr Arg Leu Ile Asp Met Glu Tyr Trp Leu Ala Cys Asn
                    180                 185                 190

Glu Glu Arg Ala Ala Gln Ala Arg Phe Gly Ala Val Met Cys Cys Cys
                    195                 200                 205

Gly Pro Cys Ala Met Tyr Arg Arg Ser Ser Leu Leu Ser Leu Leu Asp
                    210                 215                 220

Gln Tyr Glu Thr Gln Met Phe Arg Gly Lys Pro Ser Asp Phe Gly Glu
        225                 230                 235                 240

Asp Arg His Leu Thr Ile Leu Met Leu Glu Ala Gly Phe Arg Thr Glu
                    245                 250                 255

Tyr Val Pro Asp Ala Ile Ala Val Thr Val Val Pro Arg Leu Gly
                    260                 265                 270

Pro Tyr Leu Arg Gln Gln Leu Arg Trp Ala Arg Ser Thr Phe Arg Asp
                    275                 280                 285

Thr Leu Leu Ala Leu Arg Leu Leu Pro Gly Leu Asp Arg Tyr Leu Thr
                    290                 295                 300

Leu Asp Val Val Gly Gln Asn Leu Gly Pro Leu Leu Ala Leu Ser
        305                 310                 315                 320

Val Ile Ala Gly Ile Ala Gln Phe Ala Leu Thr Ala Thr Leu Pro Trp
                    325                 330                 335

Pro Thr Ile Leu Val Ile Ala Ala Met Thr Ile Ile Arg Cys Thr Val
                    340                 345                 350

Thr Ala Cys Arg Ala Arg Gln Ala Arg Phe Ile Gly Phe Ser Leu His
                    355                 360                 365

Thr Phe Ile Asn Ile Phe Leu Leu Leu Pro Leu Lys Ala Tyr Ala Leu
                    370                 375                 380

Cys Thr Leu Ser Asn Ser Asp Trp Leu Ser Arg Lys Thr Ala Thr Leu
        385                 390                 395                 400

Pro Asn Ala Asp Lys Lys Gln Ile Ile Val Ala Asn Pro Ile Ala Gly
                    405                 410                 415

Val Gly Thr Gly Ser Ser Gly Ser Ala Glu Ala Ile Arg Arg Thr Asp
                    420                 425                 430

Leu Pro Arg Asp Ser Ser Lys Leu Val Asn Ala Asp Ser Val Cys Ser
                    435                 440                 445

Ala Glu
        450

<210> SEQ ID NO 9
<211> LENGTH: 424
<212> TYPE: PRT
<213> ORGANISM: Rhizobium loti

<400> SEQUENCE: 9

```
Met Asn Leu Phe Ala Ser Ala Ser Thr Val Ala Ile Cys Ser Tyr Ala
1               5                   10                  15

Leu Leu Ser Thr Val Tyr Lys Thr Ala Gln Val Phe Tyr Thr Leu Pro
            20                  25                  30

Thr Asn Val Pro Pro Thr Ser Gly Asp Pro Pro Ser Gly Glu Pro Trp
        35                  40                  45

Pro Ser Val Asp Val Ile Ile Pro Cys Tyr Asn Glu Ala Pro Arg Thr
    50                  55                  60

Leu Ser Asp Cys Leu Ala Ser Ile Ala Ser Gln Asp Tyr Ala Gly Lys
65                  70                  75                  80

Leu Gln Val Tyr Val Val Asp Asp Gly Ser Ala Asn Arg Asp Ala Leu
                85                  90                  95

Val Gly Val His Glu Glu Tyr Ala Gly Asp Pro Arg Phe Asn Phe Val
            100                 105                 110

Ala Leu Pro Lys Asn Val Gly Lys Arg Lys Ala Gln Ile Ala Ala Ile
        115                 120                 125

Arg Arg Ser Cys Gly Asp Leu Val Leu Asn Val Asp Ser Asp Thr Ile
    130                 135                 140

Leu Ala Pro Asp Val Ile Thr Arg Leu Ala Leu Lys Met Gln Asp Gln
145                 150                 155                 160

Ala Val Gly Ala Ala Met Gly Gln Leu Ala Ala Ser Asn Arg Ser Glu
                165                 170                 175

Thr Trp Leu Thr Arg Leu Ile Asp Met Glu Tyr Trp Leu Ala Cys Asn
            180                 185                 190

Glu Glu Arg Ala Ala Gln Ala Arg Phe Gly Ala Val Met Cys Cys Cys
        195                 200                 205

Gly Pro Cys Ala Met Tyr Arg Arg Ser Ala Leu Val Ser Leu Leu Asp
    210                 215                 220

Gln Tyr Glu Thr Gln Arg Phe Arg Gly Lys Pro Ser Asp Phe Gly Glu
225                 230                 235                 240

Asp Arg His Leu Thr Ile Leu Met Leu Lys Ala Gly Phe Arg Thr Glu
                245                 250                 255

Tyr Val Pro Glu Ala Val Ala Ala Thr Val Val Pro Asn Ser Met Gly
            260                 265                 270

Pro Tyr Leu Arg Gln Gln Leu Arg Trp Ala Arg Ser Thr Phe Arg Asp
        275                 280                 285

Thr Leu Leu Ala Phe Gln Leu Leu Arg Gly Leu Asn Ile Tyr Leu Thr
    290                 295                 300

Leu Asp Val Ile Gly Gln Asn Ile Gly Pro Leu Leu Leu Ser Leu Ser
305                 310                 315                 320

Ile Leu Ala Gly Leu Ala Gln Phe Val Thr Thr Gly Thr Val Pro Trp
                325                 330                 335

Thr Ala Cys Leu Met Ile Ala Ala Met Thr Ile Val Arg Cys Ser Val
            340                 345                 350

Ala Ala Phe Arg Ala Arg Gln Leu Arg Phe Leu Gly Phe Ser Leu His
        355                 360                 365

Thr Leu Ile Asn Ile Phe Leu Leu Pro Leu Lys Ala Tyr Ala Leu
    370                 375                 380

Cys Thr Leu Ser Asn Ser Asp Trp Leu Ser Arg Ser Ala Ala Asn
385                 390                 395                 400

Val Gln Asp Thr Gly Asp Ala Leu Pro Lys Pro Asn Leu Val Gly Ser
                405                 410                 415

Asp Ala Ala Tyr Ser Glu Gln Gln
```

<210> SEQ ID NO 10
<211> LENGTH: 3900
<212> TYPE: DNA
<213> ORGANISM: Artificial Sequence
<220> FEATURE:
<223> OTHER INFORMATION: T-DNA of pTGK42
<220> FEATURE:
<221> NAME/KEY: misc_feature
<222> LOCATION: (1)..(25)
<223> OTHER INFORMATION: Left T-DNA border (complement)
<220> FEATURE:
<221> NAME/KEY: misc_feature
<222> LOCATION: (56)..(316)
<223> OTHER INFORMATION: 3' UTR from nopaline synthase gene of T-DNA
    pTIT37 (complement)
<220> FEATURE:
<221> NAME/KEY: misc_feature
<222> LOCATION: (336)..(887)
<223> OTHER INFORMATION: CDS of phosphinotricin acetyl transferase of
    Streptomyces hygroscopicus (complement)
<220> FEATURE:
<221> NAME/KEY: misc_feature
<222> LOCATION: (888)..(1720)
<223> OTHER INFORMATION: promoter region from CamV 35S gene (complement)
<220> FEATURE:
<221> NAME/KEY: misc_feature
<222> LOCATION: (1172)..(2297)
<223> OTHER INFORMATION: P35S2 promoter region from CaMV 35S gene
<220> FEATURE:
<221> NAME/KEY: misc_feature
<222> LOCATION: (2303)..(2359)
<223> OTHER INFORMATION: 5' Cab22L leadersequence
<220> FEATURE:
<221> NAME/KEY: misc_feature
<222> LOCATION: (2369)..(3562)
<223> OTHER INFORMATION: NodC coding region from A. caulinodans
<220> FEATURE:
<221> NAME/KEY: misc_feature
<222> LOCATION: (3575)..(3795)
<223> OTHER INFORMATION: 3' 35S terminator
<220> FEATURE:
<221> NAME/KEY: misc_feature
<222> LOCATION: (3879)..(3855)
<223> OTHER INFORMATION: Right T-DNA border (synthetic) (complement)

<400> SEQUENCE: 10
cggcaggata tattcaattg taaatggctc catggcgatc gctctagagg atctgcgatc      60
tagtaacata gatgacaccg cgcgcgataa tttatcctag tttgcgcgct atattttgtt    120
ttctatcgcg tattaaatgt ataattgcgg gactctaatc ataaaaaccc atctcataaa    180
taacgtcatg cattacatgt taattattac atgcttaacg taattcaaca gaaattatat    240
gataatcatc gcaagaccgg caacaggatt caatcttaag aaactttatt gccaaatgtt    300
tgaacgatct gcttcggatc ctagaacgcg tgatctcaga tctcggtgac gggcaggacc    360
ggacggggcg gtaccggcag gctgaagtcc agctgccaga aacccacgtc atgccagttc    420
ccgtgcttga agccggccgc ccgcagcatg ccgcggggg catatccgag cgcctcgtgc    480
atgcgcacgc tcgggtcgtt gggcagcccg atgacagcga ccacgctctt gaagccctgt    540
gcctccaggg acttcagcag gtgggtgtag agcgtggagc ccagtcccgt ccgctggtgg    600
cggggggaga cgtacacggt cgactcggcc gtccagtcgt aggcgttgcg tgccttccag    660
gggcccgcgt aggcgatgcc ggcgacctcg ccgtccacct cggcgacgag ccagggatag    720
cgctcccgca gacggacgag gtcgtccgtc cactcctgcg gttcctgcgg ctcggtacgg    780
aagttgaccg tgcttgtctc gatgtagtgg ttgacgatgg tgcagaccgc cggcatgtcc    840
gcctcggtgg cacggcggat gtcggccggg cgtcgttctg ggtccatggt tatagagaga    900

```
gagatagatt tatagagaga gactggtgat ttcagcgtgt cctctccaaa tgaaatgaac    960
ttccttatat agaggaaggg tcttgcgaag gatagtggga ttgtgcgtca tcccttacgt   1020
cagtggagat gtcacatcaa tccacttgct ttgaagacgt ggttggaacg tcttctttt    1080
ccacgatgct cctcgtgggt gggggtccat ctttgggacc actgtcggca gaggcatctt   1140
gaatgatagc ctttccttta tcgcaatgat ggcatttgta ggagccacct tccttttcta   1200
ctgtcctttc gatgaagtga cagatagctg gcaatggaa tccgaggagg tttcccgaaa    1260
ttatcctttg ttgaaaagtc tcaatagccc tttggtcttc tgagactgta tctttgacat   1320
ttttggagta gaccagagtg tcgtgctcca ccatgttgac gaagattttc ttcttgtcat   1380
tgagtcgtaa aagactctgt atgaactgtt cgccagtctt cacggcgagt tctgttagat   1440
cctcgatttg aatcttagac tccatgcatg gccttagatt cagtaggaac tacctttta    1500
gagactccaa tctctattac ttgccttggt ttatgaagca agccttgaat cgtccatact   1560
ggaatagtac ttctgatctt gagaaatatg tcttctctg tgttcttgat gcaattagtc    1620
ctgaatcttt tgactgcatc tttaaccttc ttgggaaggt atttgatctc ctggagattg   1680
ttactcgggt agatcgtctt gatgagacct gctgcgtagg aacgcggccg ctgtacaggg   1740
cccgggcata tggcgcgcca tatgcaccat acatggagtc aaaaattcag atcgaggatc   1800
taacagaact cgccgtgaag actggcgaac agttcataca gagtctttta cgactcaatg   1860
acaagaagaa aatcttcgtc aacatggtgg agcacgacac tctcgtctac tccaagaata   1920
tcaaagatac agtctcagaa gaccaaaggg ctattgagac ttttcaacaa agggtaatat   1980
cgggaaacct cctcggattc cattgcccag ctatctgtca cttcatcaaa aggacagtag   2040
aaaaggaagg tggcacctac aaatgccatc attgcgataa aggaaaggct atcgttcaag   2100
atgcctctgc cgacagtggt cccaaagatg gacccccacc cacgaggagc atcgtggaaa   2160
aagaagacgt tccaaccacg tcttcaaagc aagtggattg atgtgatatc tccactgacg   2220
taagggatga cgcacaatcc cactatcctt cgcaagaccc ttcctctata taggaagtt    2280
catttcattt ggagaggact cgagctcatt tctctattac ttcagccata acaaaagaac   2340
tcttttctct tcttattaaa ccaaaaccat gagtgtcgta gatgtgatcg gtttgcttgc   2400
gactgcagcc tacgtgacgt tggcgagcgc atacaaggtg gtccagttca ttaacgtgtc   2460
gagcgtaacg gatgtcgctg gtctcgaaag tgatgctttg ccgctcactc caagggttga   2520
cgttatcgtg ccgacattca atgagaactc cagcacattg ctcgagtgcg tcgcttctat   2580
atgcgcacaa gactaccgcg gaccaataac gattgtcgtg gtagacgatg ggtcgaccaa   2640
caaaacatca tttcacgcag tatgcgacaa gtacgcgagc gacgaaaggt tcatatttgt   2700
cgaacttgat caaacaaggg gaagcgcgc gcgcaaatg gaggccatca ggagaacaga    2760
cggagacctg atactaaacg tagactcgga cacggttata gataaggatg ttgttacaaa   2820
gcttgcgtcg tccatgagag ccccgaatgt cggtggtgtc atgggcagc tcgttgcaaa    2880
gaatcgagaa agatcttggc ttaccagatt aatcgatatg gagtactggc ttgcgtgtaa   2940
cgaggagcgc attgcgcagt cgaggtttgg ctccgtgatg tgttgttgtg ggccgtgcgc   3000
catgtataga agatctgcaa ttacgccact attggcagaa tatgagcacc agacattcct   3060
agggcgtccg agcaactttg gtgaggatcg ccatctcaca atcctgatgc tgaaggcggg   3120
atttcggacc gggtacgtcc caggtgccgt agcgaggacg ttggttccgg atgggctggc   3180
gccgtacctg cgccagcaac tccgctgggc ccgcagcact tatcgcgaca ccgccctcgc   3240
```

```
cttacgtata aagaaaaatc taagcaaata tatcaccttt gagatatgcg cacagaattt    3300
gggtacggct ctcttacttg tgatgaccat gatttcgctt tcgctgacta catcagggtc    3360
gcaaacgccc gttatcattc tgggtgtcgt tgtggggatg tctataataa gatgttgttc    3420
tgtcgccctt atagcgaaag attttcggtt tctatacttc atcgttcact cagcgttgaa    3480
tgttctaatt ttaacgccgt taaaactcta tgccctgtta accattcggg atagtcggtg    3540
gctatcacgc gagagttcct aagctagcaa gcttggacac gctgaaatca ccagtctctc    3600
tctacaaatc tatctctctc tattttctcc ataataatgt gtgagtagtt cccagataag    3660
ggaattaggg ttcctatagg gtttcgctca tgtgttgagc atataagaaa cccttagtat    3720
gtatttgtat ttgtaaaata cttctatcaa taaaatttct aattcctaaa accaaaatcc    3780
agtactaaaa tccagatcat gcatggtaca gcggccaatt gccaattccg gggtaccggt    3840
cgacggccga gtactggcag gatatatacc gttgtaattt gtcgcgtgtg aataagtcgc    3900

<210> SEQ ID NO 11
<211> LENGTH: 4680
<212> TYPE: DNA
<213> ORGANISM: Artificial Sequence
<220> FEATURE:
<223> OTHER INFORMATION: T-DNA of pTGK44
<220> FEATURE:
<221> NAME/KEY: misc_feature
<222> LOCATION: (1)..(25)
<223> OTHER INFORMATION: Left T-DNA border (synthetic) (complement)
<220> FEATURE:
<221> NAME/KEY: misc_feature
<222> LOCATION: (56)..(316)
<223> OTHER INFORMATION: 3' UTR from nopaline synthaste gene of T-DNA
      pTIT37 (complement)
<220> FEATURE:
<221> NAME/KEY: misc_feature
<222> LOCATION: (336)..(887)
<223> OTHER INFORMATION: CDS of phosphinotricin acetyltransferase of
      Streptomyces hygroscopicus (complement)
<220> FEATURE:
<221> NAME/KEY: misc_feature
<222> LOCATION: (888)..(1720)
<223> OTHER INFORMATION: P35S3 promoter region from CaMV (complement)
<220> FEATURE:
<221> NAME/KEY: misc_feature
<222> LOCATION: (1172)..(2297)
<223> OTHER INFORMATION: P35S2 promoter region from CaMV
<220> FEATURE:
<221> NAME/KEY: misc_feature
<222> LOCATION: (2303)..(2359)
<223> OTHER INFORMATION: 5' cab22L leadersequence
<220> FEATURE:
<221> NAME/KEY: misc_feature
<222> LOCATION: (2369)..(3558)
<223> OTHER INFORMATION: nodC coding region from A.caulinodans
<220> FEATURE:
<221> NAME/KEY: misc_feature
<222> LOCATION: (3560)..(4279)
<223> OTHER INFORMATION: EGFP ORF encoding enhanced green fluorescent
      protein
<220> FEATURE:
<221> NAME/KEY: misc_feature
<222> LOCATION: (4304)..(4524)
<223> OTHER INFORMATION: 3' 35S terminator
<220> FEATURE:
<221> NAME/KEY: misc_feature
<222> LOCATION: (4608)..(4584)
<223> OTHER INFORMATION: Right T-DNA border (synthetic)

<400> SEQUENCE: 11
cggcaggata tattcaattg taaatggctc catggcgatc gctctagagg atctgcgatc      60
tagtaacata gatgacaccg cgcgcgataa tttatcctag tttgcgcgct atattttgtt    120
```

```
ttctatcgcg tattaaatgt ataattgcgg gactctaatc ataaaaaccc atctcataaa      180
taacgtcatg cattacatgt taattattac atgcttaacg taattcaaca gaaattatat      240
gataatcatc gcaagaccgg caacaggatt caatcttaag aaactttatt gccaaatgtt      300
tgaacgatct gcttcggatc ctagaacgcg tgatctcaga tctcggtgac gggcaggacc      360
ggacggggcg gtaccggcag gctgaagtcc agctgccaga aacccacgtc atgccagttc      420
ccgtgcttga agccggccgc ccgcagcatg ccgcggggggg catatccgag cgcctcgtgc      480
atgcgcacgc tcgggtcgtt gggcagcccg atgacagcga ccacgctctt gaagccctgt      540
gcctccaggg acttcagcag gtgggtgtag agcgtggagc ccagtcccgt ccgctggtgg      600
cggggggaga cgtacacggt cgactcggcc gtccagtcgt aggcgttgcg tgccttccag      660
gggcccgcgt aggcgatgcc ggcgacctcg ccgtccacct cggcgacgag ccagggatag      720
cgctcccgca gacggacgag gtcgtccgtc cactcctgcg gttcctgcgg ctcggtacgg      780
aagttgaccg tgcttgtctc gatgtagtgg ttgacgatgg tgcagaccgc cggcatgtcc      840
gcctcggtgg cacggcggat gtcggccggg cgtcgttctg ggtccatggt tatagagaga      900
gagatagatt tatagagaga gactggtgat tcagcgtgt cctctccaaa tgaaatgaac      960
ttccttatat agaggaaggg tcttgcgaag gatagtggga ttgtgcgtca tcccttacgt     1020
cagtggagat gtcacatcaa tccacttgct ttgaagacgt ggttggaacg tcttcttttt     1080
ccacgatgct cctcgtgggt gggggtccat ctttgggacc actgtcggca gaggcatctt     1140
gaatgatagc ctttcctttta tcgcaatgat ggcatttgta ggagccacct tccttttcta     1200
ctgtcctttc gatgaagtga cagatagctg gcaatggaa tccgaggagg tttcccgaaa     1260
ttatcctttg ttgaaaagtc tcaatagccc tttggtcttc tgagactgta tctttgacat     1320
ttttggagta gaccagagtg tcgtgctcca ccatgttgac gaagattttc ttcttgtcat     1380
tgagtcgtaa aagactctgt atgaactgtt cgccagtctt cacggcgagt tctgttagat     1440
cctcgatttg aatcttagac tccatgcatg gccttagatt cagtaggaac taccttttta     1500
gagactccaa tctctattac ttgccttggt ttatgaagca agccttgaat cgtccatact     1560
ggaatagtac ttctgatctt gagaaatatg tcttttctctg tgttcttgat gcaattagtc     1620
ctgaatcttt tgactgcatc tttaaccttc ttgggaaggt atttgatctc ctggagattg     1680
ttactcgggt agatcgtctt gatgagacct gctgcgtagg aacgcggccg ctgtacaggg     1740
cccgggcata tggcgcgcca tatgcaccat acatggagtc aaaaattcag atcgaggatc     1800
taacagaact cgccgtgaag actggcgaac agttcataca gagtctttta cgactcaatg     1860
acaagaagaa aatcttcgtc aacatggtgg agcacgacac tctcgtctac tccaagaata     1920
tcaaagatac agtctcagaa gaccaaaggg ctattgagac ttttcaacaa agggtaatat     1980
cgggaaacct cctcggattc cattgcccag ctatctgtca cttcatcaaa aggacagtag     2040
aaaaggaagg tggcacctac aaatgccatc attgcgataa aggaaaggct atcgttcaag     2100
atgcctctgc cgacagtggt cccaaagatg gacccccacc cacgaggagc atcgtggaaa     2160
aagaagacgt tccaaccacg tcttcaaagc aagtggattg atgtgatatc tccactgacg     2220
taagggatga cgcacaatcc cactatcctt cgcaagaccc ttcctctata taggaagtt      2280
catttcattt ggagaggact cgagctcatt tctctattac ttcagccata acaaaagaac     2340
tcttttctct tcttattaaa ccaaaaccat gagtgtcgta gatgtgatcg gtttgcttgc     2400
gactgcagcc tacgtgacgt tggcgagcgc atacaaggtg gtccagttca ttaacgtgtc     2460
gagcgtaacg gatgtcgctg gtctcgaaag tgatgctttg ccgctcactc caagggttga     2520
```

```
cgttatcgtg ccgacattca atgagaactc cagcacattg ctcgagtgcg tcgcttctat    2580
atgcgcacaa gactaccgcg gaccaataac gattgtcgtg gtagacgatg ggtcgaccaa    2640
caaaacatca tttcacgcag tatgcgacaa gtacgcgagc gacgaaaggt tcatatttgt    2700
cgaacttgat caaaacaagg ggaagcgcgc cgcgcaaatg gaggccatca ggagaacaga    2760
cggagacctg atactaaacg tagactcgga cacggttata gataaggatg ttgttacaaa    2820
gcttgcgtcg tccatgagag ccccgaatgt cggtggtgtc atggggcagc tcgttgcaaa    2880
gaatcgagaa agatcttggc ttaccagatt aatcgatatg gagtactggc ttgcgtgtaa    2940
cgaggagcgc attgcgcagt cgaggtttgg ctccgtgatg tgttgttgtg ggccgtgcgc    3000
catgtataga agatctgcaa ttacgccact attggcagaa tatgagcacc agacattcct    3060
agggcgtccg agcaactttg gtgaggatcg ccatctcaca atcctgatgc tgaaggcggg    3120
atttcggacc gggtacgtcc caggtgccgt agcgaggacg ttggttccgg atgggctggc    3180
gccgtacctg cgccagcaac tccgctgggc ccgcagcact tatcgcgaca ccgccctcgc    3240
cttacgtata aagaaaaatc taagcaaata tatcacccttt gagatatgcg cacagaattt    3300
gggtacggct ctcttacttg tgatgaccat gatttcgctt tcgctgacta catcagggtc    3360
gcaaacgccc gttatcattc tgggtgtcgt tgtggggatg tctataataa gatgttgttc    3420
tgtcgccctt atagcgaaag atttttcggtt tctatacttc atcgttcact cagcgttgaa    3480
tgttctaatt ttaacgccgt taaaactcta tgccctgtta accattcggg atagtcggtg    3540
gctatcacgc gagagttcca tggtgagcaa gggcgaggag ctgttcaccg gggtggtgcc    3600
catcctggtc gagctggacg gcgacgtaaa cggccacaag ttcagcgtgt ccggcgaggg    3660
cgagggcgat gccacctacg gcaagctgac cctgaagttc atctgcacca ccggcaagct    3720
gcccgtgccc tggcccaccc tcgtgaccac cctgacctac ggcgtgcagt gcttcagccg    3780 ctacccccgac cacatgaagc agcacgactt cttcaagtcc gccatgcccg aaggctacgt    3840
ccaggagcgc accatcttct tcaaggacga cggcaactac aagacccgcg ccgaggtgaa    3900
gttcgagggc gacaccctgg tgaaccgcat cgagctgaag ggcatcgact tcaaggagga    3960
cggcaacatc ctggggcaca agctggagta caactacaac agccacaacg tctatatcat    4020
ggccgacaag cagaagaacg gcatcaaggt gaacttcaag atccgccaca acatcgagga    4080
cggcagcgtg cagctcgccg accactacca gcagaacacc cccatcggcg acggccccgt    4140
gctgctgccc gacaaccact acctgagcac ccagtccgcc ctgagcaaag accccaacga    4200
gaagcgcgat cacatggtcc tgctggagtt cgtgaccgcc gccgggatca ctctcggcat    4260
ggacgagctg tacaagtaaa gcggccgcga ctctagcaag cttggacacg ctgaaatcac    4320
cagtctctct ctacaaatct atctctctct attttctcca taataatgtg tgagtagttc    4380
ccagataagg gaattagggt tcctataggg tttcgctcat gtgttgagca tataagaaac    4440
ccttagtatg tatttgtatt tgtaaaatac ttctatcaat aaaatttcta attcctaaaa    4500
ccaaaatcca gtactaaaat ccagatcatg catggtacag cggccaattg ccaattccgg    4560
ggtaccggtc gacggccgag tactggcagg atatataccg ttgtaatttg tcgcgtgtga    4620
ataagtcgct gtgtatgttt gtttgattgt ttctgttgga gtgcagccca tttcaccgga    4680
```

<210> SEQ ID NO 12
<211> LENGTH: 5490
<212> TYPE: DNA
<213> ORGANISM: Artificial Sequence
<220> FEATURE:

```
<223> OTHER INFORMATION: T-DNA of pTDBI5
<220> FEATURE:
<221> NAME/KEY: misc_feature
<222> LOCATION: (1)..(25)
<223> OTHER INFORMATION: Left T-DNA border (complement)
<220> FEATURE:
<221> NAME/KEY: misc_feature
<222> LOCATION: (56)..(316)
<223> OTHER INFORMATION: 3' nos: 3'UTR from nopaline synthase gene of
      T-DNA pTiT37 (complement)
<220> FEATURE:
<221> NAME/KEY: misc_feature
<222> LOCATION: (887)..(336)
<223> OTHER INFORMATION: bar: coding sequence of phosphinotricin acetyl
      transferease of Streptomyces hygroscopicus (complement)
<220> FEATURE:
<221> NAME/KEY: misc_feature
<222> LOCATION: (888)..(1720)
<223> OTHER INFORMATION: P35S3: Promoter region from CaMV35S gene
      (complement)
<220> FEATURE:
<221> NAME/KEY: misc_feature
<222> LOCATION: (1796)..(2303)
<223> OTHER INFORMATION: P35S2: Promoter region from CaMV35S gene
<220> FEATURE:
<221> NAME/KEY: misc_feature
<222> LOCATION: (2304)..(2368)
<223> OTHER INFORMATION: 5'cab22L: untranslated leader sequence of
      cab22L gene from Petunia
<220> FEATURE:
<221> NAME/KEY: misc_feature
<222> LOCATION: (2369)..(3992)
<223> OTHER INFORMATION: chs2exon1: exon 1 of the chitin synthase gene 2
      from Neurospora crassa
<220> FEATURE:
<221> NAME/KEY: misc_feature
<222> LOCATION: (3993)..(5203)
<223> OTHER INFORMATION: chs2exon2: exon 2 of the chitin synthase gene 2
      from Neurospora crassa
<220> FEATURE:
<221> NAME/KEY: misc_feature
<222> LOCATION: (5205)..(5453)
<223> OTHER INFORMATION: 3'35S: 3' untranslated region from the CaMV35S
      gene
<220> FEATURE:
<221> NAME/KEY: misc_feature
<222> LOCATION: (5488)..(5512)
<223> OTHER INFORMATION: RB: right T-DNA border (synthetic) (complement)

<400> SEQUENCE: 12
cggcaggata tattcaattg taaatggctc catggcgatc gctctagagg atctgcgatc      60
tagtaacata gatgacaccg cgcgcgataa tttatcctag tttgcgcgct atattttgtt     120
ttctatcgcg tattaaatgt ataattgcgg gactctaatc ataaaaaccc atctcataaa     180
taacgtcatg cattacatgt taattattac atgcttaacg taattcaaca gaaattatat     240
gataatcatc gcaagaccgg caacaggatt caatcttaag aaactttatt gccaaatgtt     300
tgaacgatct gcttcggatc ctagaacgcg tgatctcaga tctcggtgac gggcaggacc     360
ggacggggcg gtaccggcag gctgaagtcc agctgccaga acccacgtc atgccagttc      420 ccgtgcttga agccggccgc ccgcagcatg ccgcggggg catatccgag cgcctcgtgc      480
atgcgcacgc tcgggtcgtt gggcagcccg atgacagcga ccacgctctt gaagccctgt     540
gcctccaggg acttcagcag gtgggtgtag agcgtggagc ccagtcccgt ccgctggtgg     600
cgggggagga cgtacacggt cgactcggcc gtccagtcgt aggcgttgcg tgccttccag     660
gggcccgcgt aggcgatgcc ggcgacctcg ccgtccacct cggcgacgag ccagggatag     720
cgctcccgca gacggacgag gtcgtccgtc cactcctgcg gttcctgcgg ctcggtacgg     780
aagttgaccg tgcttgtctc gatgtagtgg ttgacgatgg tgcagaccgc cggcatgtcc     840
```

```
gcctcggtgg cacggcggat gtcggccggg cgtcgttctg ggtccatggt tatagagaga    900
gagatagatt tatagagaga gactggtgat tcagcgtgt cctctccaaa tgaaatgaac    960
ttccttatat agaggaaggg tcttgcgaag gatagtggga ttgtgcgtca tcccttacgt   1020
cagtggagat gtcacatcaa tccacttgct ttgaagacgt ggttggaacg tcttcttttt   1080
ccacgatgct cctcgtgggt ggggtccat ctttgggacc actgtcggca gaggcatctt   1140
gaatgatagc ctttccttta tcgcaatgat ggcatttgta ggagccacct tccttttcta   1200
ctgtcctttc gatgaagtga cagatagctg ggcaatggaa tccgaggagg tttcccgaaa   1260
ttatcctttg ttgaaaagtc tcaatagccc tttggtcttc tgagactgta tctttgacat   1320
ttttggagta gaccagagtg tcgtgctcca ccatgttgac gaagattttc ttcttgtcat   1380
tgagtcgtaa aagactctgt atgaactgtt cgccagtctt cacggcgagt tctgttagat   1440
cctcgatttg aatcttagac tccatgcatg gccttagatt cagtaggaac tacctttta   1500
gagactccaa tctctattac ttgccttggt ttatgaagca agccttgaat cgtccatact   1560
ggaatagtac ttctgatctt gagaaatatg tcttctctg tgttcttgat gcaattagtc   1620
ctgaatcttt tgactgcatc tttaaccttc ttgggaaggt atttgatctc ctggagattg   1680
ttactcgggt agatcgtctt gatgagacct gctgcgtagg aacgcggccg ctgtacaggg   1740
cccgggcata tggcgcgcca tatgcaccat acatggagtc aaaaattcag atcgaggatc   1800
taacagaact cgccgtgaag actggcgaac agttcataca gagtctttta cgactcaatg   1860
acaagaagaa aatcttcgtc aacatggtgg agcacgacac tctcgtctac tccaagaata   1920
tcaaagatac agtctcagaa gaccaaaggg ctattgagac ttttcaacaa agggtaatat   1980
cgggaaacct cctcggattc cattgcccag ctatctgtca cttcatcaaa aggacagtag   2040
aaaaggaagt ggcacctac aaatgccatc attgcgataa aggaaaggct atcgttcaag   2100
atgcctctgc cgacagtggt cccaaagatg gacccccacc cacgaggagc atcgtggaaa   2160
aagaagacgt tccaaccacg tcttcaaagc aagtggattg atgtgatatc tccactgacg   2220
taagggatga cgcacaatcc cactatcctt cgcaagaccc ttcctctata taggaagtt   2280
catttcattt ggagaggact cgagctcatt tctctattac ttcagccata caaaagaac   2340
tcttttctct tcttattaaa ccaaaaccat ggagtccaga atcagcaacc ggttatcgag   2400
ttccgccaca aggacggtac gagccttcag aaatcgatgt catgccaggc cagggacacc   2460
gggatcgagt tacggaaatg cgaggcgacc gcttccctcg gcaccagcgc ctttacacta   2520
caatagccca agtcgcgcag cgagtcatta tccacggtac catggaggtt atgcggacga   2580
cgtgacagtt agcatgggac cggacgacga tcgtacagat atctttggcc ccgaaaccga   2640
tctcagcgaa acgcgccacc tcaacgcgc atacgggttt cggtcatccc agatcaccct   2700
cagcgaagat ccccacggca cccacgcgcg ttccgggtac gacgacgaag acgatgtgag   2760
caccacttat tcctccaaca cgggcaccag cgcttcaggt gtcgacaagt tcgagcatta   2820
cggtcccatt ccggaggaag gcaagcacga gcggcgcggc gtgcgaccac cacagatgtc   2880
gaggaaggaa gtccagctca tcaacggcga actcgttctc gagtgcaaga ttccgactat   2940
attgtattcg ttttttgccca ggagagacga agtggagttt acgcacatgc ggtacacagc   3000
cgtcacttgt gaccctgatg actttgttgc caggggttac aagttgcgcc agaatatcgg   3060
tcgtaccgcc agggagacgg agctgttcat ctgcgtgacc atgtacaacg aggacgagtt   3120
cggattcaca cggactatgc acgcagtcat gaagaacatt tcgcattttt gttcccgaaa   3180
caagagtagg acgtggggag cggatggtg gcagaagatt gtggtctgtg tggtttcgga   3240
```

```
tggacgagag atcattcacc cccggacctt ggacgccctc gcagccatgg gcgtttacca   3300
gcacggtatc gccaagaact tgtcaacca gaaggcggtg caggcccacg tttacgagta    3360
cacgacacaa gtgtctctgg acagcgacct caagttcaag ggcgccgaga agggcatcgt   3420
gccctgccag atgattttt gcttgaagga gaagaaccaa aagaaactca actcgcatag    3480
atggttcttc aacgcctttg gcaaagcctt gaacccgaat gtgtgtatcc tcctagacgt   3540
cggcacccgc cccggcggca caagtctcta ccatctctgg aaagccttcg acacggattc   3600
caacgtggcg ggggcctgcg gggaaatcaa agcgatgaag gggcggtttg cgggaatttt   3660
gctcaaccct ctggtggcta gtcagaactt tgagtacaag atgagcaata ttctggacaa   3720
accgttggag tcggtgtttg ggtacatcac ggtgttgccg ggcgccttgt cggcgtatcg   3780
gtaccatgcg ctgcagaacg atgagacggg ccatgggccg ttgagtcagt atttcaaggg   3840
cgagacgctc catgggcagc acgcggatgt gtttacggcg aacatgtact ggccgagga    3900
ccgaattctg tgttgggagt tggtggccaa gaggggtgag aggtgggtgt tgaagtatgt   3960
gaaggggtgt acgggtgaga cggatgtgcc tgacaccgtc ccggaattcg tctcgcaacg   4020
tcgtcgttgg ctcaacggtg ccttcttcgc cgccgtctac tccctcgtcc actttcgaca   4080
aatctggaaa accgaccaca cctttatgcg caaagccctt ctccacgtcg aattcctcta   4140
ccacctcctg caactcctct tcacctactt ctccctggcc aacttctacc tgccttcta   4200
ctttatcgcc ggcggtctcg ccgatcccca cgtcgaccct tttaactcgg acggccacgt   4260
cgcgcgcatc atcttcaaca tcctccgcta cgtctgcgtc ctgctgatct gcacacaatt   4320
catcttgtcc ctcggcaacc gtccgcaggg tgccaaaaga atgtatctcg catccatgat   4380
catctacgcc gtcatcatgg tgtacaccac cttcgccacc atcttcatcg tcgtgcgaca   4440
aatccaaccc tctcaaaaat ccgacgacaa gcccgacctc gaactcggca caacgtctt    4500
caccaacctg atcgtctccg tggctagtac cctcggctc tacttcgtca tgtcctttct    4560
ctatctcgac ccctggcaca tgttcacctc ggccatccag tactttgtcc tgctgccttc   4620
ctacatctgc acgctccaga tctacgcctt ttgcaacacc cacgacgtca catggggcac   4680
caaaggcgac aacgtgatgc gcaccgatct cggaggcgcc attggcaagg gaagcaccgt   4740
cgaactggaa atgccttcgg accaactcga catcgactcg ggatacgacg aatgtctacg   4800
taatctccgc gatcgcgtca tggtccctgc cgttcccgtg tccgaggacc agctgcagca   4860
ggattactac aagtcggtgc gcacgtacat ggtggtgtcg tggatggtgg ccaacgcgac   4920
gctggccatg gcgtctcgg aagcgtatgg cgattcggaa attgggata atttttactt     4980
gcggtttatc ctgtgggcgg tggcggccct ggcgctgttt agagcgttgg ggtcgacgac   5040
gtttgcggcg attaatctgg tgagtgctct cgtggagggc aggtcaggc tgaggttgaa    5100
tatgaaaggg tttaggtgga ttaaggagaa gtgggggat gcggatgtga agggcaagtt    5160
tgaggggttg ggggatcggg cgaggggtt ggcgaggcgg tgagctagca agcttggaca    5220
cgctgaaatc accagtctct ctctacaaat ctatctctct ctatttctc cataataatg    5280
tgtgagtagt tcccagataa gggaattagg gttcctatag ggtttcgctc atgtgttgag   5340
catataagaa acccttagta tgtatttgta tttgtaaaat acttctatca ataaatttc    5400
taattcctaa aaccaaaatc cagtactaaa atccagatca tgcatggtac agcggccaat   5460
tccggggtac ggtcgacggc cgagtactgg                                    5490
```

<210> SEQ ID NO 13

```
<211> LENGTH: 5606
<212> TYPE: DNA
<213> ORGANISM: Artificial Sequence
<220> FEATURE:
<223> OTHER INFORMATION: T-DNA of ppTDBI37
<220> FEATURE:
<221> NAME/KEY: misc_feature
<222> LOCATION: (1)..(25)
<223> OTHER INFORMATION: Left T-DNA border (complement)
<220> FEATURE:
<221> NAME/KEY: misc_feature
<222> LOCATION: (56)..(316)
<223> OTHER INFORMATION: 3' nos: 3' UTR from nopaline synthase gene of
      T-DNA pTiT37 (complement)
<220> FEATURE:
<221> NAME/KEY: misc_feature
<222> LOCATION: (336)..(887)
<223> OTHER INFORMATION: bar: CDS of phosphinotricin acetyl transferase
      of Streptomyces hygroscopicus (complement)
<220> FEATURE:
<221> NAME/KEY: misc_feature
<222> LOCATION: (888)..(1720)
<223> OTHER INFORMATION: P35S3: promoter region of CaMV 35S transcript
      (complement)
<220> FEATURE:
<221> NAME/KEY: misc_feature
<222> LOCATION: (1769)..(2303)
<223> OTHER INFORMATION: P35S2: promoter region of CaMV 35S transcript
<220> FEATURE:
<221> NAME/KEY: misc_feature
<222> LOCATION: (2304)..(2368)
<223> OTHER INFORMATION: 5'cab22L: leader sequence of the cab22L gene
      from Petunia
<220> FEATURE:
<221> NAME/KEY: misc_feature
<222> LOCATION: (2373)..(2477)
<223> OTHER INFORMATION: XylT: Golgi targeting signal from beta
      1,2-xylosyltransferase protein
<220> FEATURE:
<221> NAME/KEY: misc_feature
<222> LOCATION: (2487)..(5321)
<223> OTHER INFORMATION: CHS2: coding region chitin synthase 2 of
      Neurospora crassa (exon 1 and exon 2).
<220> FEATURE:
<221> NAME/KEY: misc_feature
<222> LOCATION: (5323)..(5571)
<223> OTHER INFORMATION: 3'35S: 3' UTR fragment of the CaMV 35S
      transcript
<220> FEATURE:
<221> NAME/KEY: misc_feature
<222> LOCATION: (5630)..(5606)
<223> OTHER INFORMATION: RB: Right T-DNA border (synthetic) (complement)

<400> SEQUENCE: 13
cggcaggata tattcaattg taaatggctc catggcgatc gctctagagg atctgcgatc      60
tagtaacata gatgacaccg cgcgcgataa tttatcctag tttgcgcgct atattttgtt    120
ttctatcgcg tattaaatgt ataattgcgg gactctaatc ataaaaaccc atctcataaa    180
taacgtcatg cattacatgt taattattac atgcttaacg taattcaaca gaaattatat    240
gataatcatc gcaagaccgg caacaggatt caatcttaag aaactttatt gccaaatgtt    300
tgaacgatct gcttcggatc ctagaacgcg tgatctcaga tctcggtgac gggcaggacc    360
ggacggggcg gtaccggcag gctgaagtcc agctgccaga acccacgtc atgccagttc    420 ccgtgcttga agccggccgc ccgcagcatg ccgcggggg catatccgag cgcctcgtgc    480
atgcgcacgc tcgggtcgtt gggcagcccg atgacagcga ccacgctctt gaagccctgt    540
gcctccaggg acttcagcag gtgggtgtag agcgtggagc ccagtcccgt ccgctggtgg    600
cggggggaga cgtacacggt cgactcggcc gtccagtcgt aggcgttgcg tgccttccag    660
gggcccgcgt aggcgatgcc ggcgacctcg ccgtccacct cggcgacgag ccagggatag    720
```

```
cgctcccgca gacggacgag gtcgtccgtc cactcctgcg gttcctgcgg ctcggtacgg      780
aagttgaccg tgcttgtctc gatgtagtgg ttgacgatgg tgcagaccgc cggcatgtcc      840
gcctcggtgg cacggcggat gtcggccggg cgtcgttctg ggtccatggt tatagagaga      900
gagatagatt tatagagaga gactggtgat ttcagcgtgt cctctccaaa tgaaatgaac      960
ttccttatat agaggaaggg tcttgcgaag gatagtggga ttgtgcgtca tcccttacgt     1020
cagtggagat gtcacatcaa tccacttgct ttgaagacgt ggttggaacg tcttcttttt     1080
ccacgatgct cctcgtgggt ggggtccat ctttgggacc actgtcggca gaggcatctt      1140
gaatgatagc ctttccttta tcgcaatgat ggcatttgta ggagccacct tccttttcta     1200
ctgtcctttc gatgaagtga cagatagctg ggcaatggaa tccgaggagg tttcccgaaa     1260
ttatcctttg ttgaaaagtc tcaatagccc tttggtcttc tgagactgta tctttgacat     1320
ttttggagta gaccagagtg tcgtgctcca ccatgttgac gaagattttc ttcttgtcat     1380
tgagtcgtaa aagactctgt atgaactgtt cgccagtctt cacggcgagt tctgttagat     1440
cctcgatttg aatcttagac tccatgcatg gccttagatt cagtaggaac tacctttta     1500
gagactccaa tctctattac ttgccttggt ttatgaagca agccttgaat cgtccatact     1560
ggaatagtac ttctgatctt gagaaatatg tctttctctg tgttcttgat gcaattagtc     1620
ctgaatcttt tgactgcatc tttaaccttc ttgggaaggt atttgatctc ctggagattg     1680
ttactcgggt agatcgtctt gatgagacct gctgcgtagg aacgcggccg ctgtacaggg     1740
cccgggcata tggcgcgcca tatgcaccat acatggagtc aaaaattcag atcgaggatc     1800
taacagaact cgccgtgaag actggcgaac agttcataca gagtctttta cgactcaatg     1860
acaagaagaa aatcttcgtc aacatggtgg agcacgacac tctcgtctac tccaagaata     1920
tcaaagatac agtctcagaa gaccaaaggg ctattgagac ttttcaacaa agggtaatat     1980
cgggaaacct cctcggattc cattgcccag ctatctgtca cttcatcaaa aggacagtag     2040
aaaaggaagg tggcacctac aaatgccatc attgcgataa aggaaaggct atcgttcaag     2100
atgcctctgc cgacagtggt cccaaagatg gacccccacc cacgaggagc atcgtggaaa     2160
aagaagacgt tccaaccacg tcttcaaagc aagtggattg atgtgatatc tccactgacg     2220
taagggatga cgcacaatcc cactatcctt cgcaagaccc ttcctctata taggaagtt      2280
catttcattt ggagaggact cgagctcatt tctctattac ttcagccata acaaaagaac     2340
tcttttctct tcttattaaa ccaaaaccat ggatgagtaa acggaatccg aagattctga     2400
agatttttct gtatatgtta cttctcaact ctctctttct catcatctac ttcgtttttc     2460
actcatcgtc gttttcagcc aaaaccatgg agtccagaat cagcaaccgg ttatcgagtt     2520
ccgccacaag gacggtacga gccttcagaa atcgatgtca tgccaggcca gggacaccgg     2580
gatcgagtta cggaaatgcg aggcgaccgc ttccctcggc accagcgcct ttacactaca     2640
atagcccaag tcgcgcagcg agtcattatc cacggtacca tggaggttat gcggacgacg     2700
tgacagttag catgggaccg gacgacgatc gtacagatat ctttggcccc gaaaccgatc     2760
tcagcgaaac gcgccacctc aacgacgcat acgggtttcg gtcatcccag atcaccctca     2820
gcgaagatcc ccacggcacc cacgcgcgtt cccggtacga cgacgaagac gatgtgagca     2880
ccacttattc ctccaacacg ggcaccagcg cttcaggtgt cgacaagttc gagcattacg     2940
gtcccattcc ggaggaaggc aagcacgagc ggcgcggcgt gcgaccacca cagatgtcga     3000
ggaaggaagt ccagctcatc aacggcgaac tcgttctcga gtgcaagatt ccgactatat     3060
tgtattcgtt tttgcccagg agagacgaag tggagtttac gcacatgcgg tacacagccg     3120
```

```
tcacttgtga ccctgatgac tttgttgcca ggggttacaa gttgcgccag aatatcggtc   3180
gtaccgccag ggagacggag ctgttcatct gcgtgaccat gtacaacgag gacgagttcg   3240
gattcacacg gactatgcac gcagtcatga agaacatttc gcattttgt  tcccgaaaca   3300 agagtaggac gtggggagcg gatgggtggc agaagattgt ggtctgtgtg gtttcggatg   3360
gacgagagat cattcacccc cggaccttgg acgccctcgc agccatgggc gtttaccagc   3420
acggtatcgc caagaacttt gtcaaccaga aggcggtgca ggcccacgtt tacgagtaca   3480
cgacacaagt gtctctggac agcgacctca gttcaaggg  cgccgagaag ggcatcgtgc   3540
cctgccagat gattttttgc ttgaaggaga gaaccaaaa  gaaactcaac tcgcatagat   3600
ggttcttcaa cgcctttggc aaagccttga acccgaatgt gtgtatcctc ctagacgtcg   3660
gcacccgccc cggcggcaca agtctctacc atctctggaa agccttcgac acggattcca   3720
acgtggcggg ggcctgcggg gaaatcaaag cgatgaaggg gcggtttggc gggaatttgc   3780
tcaaccctct ggtggctagt cagaactttg agtacaagat gagcaatatt ctggacaaac   3840
cgttggagtc ggtgtttggg tacatcacgg tgttgccggg cgccttgtcg gcgtatcggt   3900
accatgcgct gcagaacgat gagacgggcc atgggccgtt gagtcagtat ttcaagggcg   3960
agacgctcca tgggcagcac gcggatgtgt ttacggcgaa catgtacttg gccgaggacc   4020
gaattctgtg ttgggagttg gtggccaaga ggggtgagag gtgggtgttg aagtatgtga   4080 agggggtgtac gggtgagacg gatgtgcctg acaccgtccc ggaattcgtc tcgcaacgtc   4140
gtcgttggct caacggtgcc ttcttcgccg ccgtctactc cctcgtccac tttcgacaaa   4200
tctggaaaac cgaccacacc tttatgcgca aagcccttct ccacgtcgaa ttcctctacc   4260
acctcctgca actcctcttc acctacttct ccctggccaa cttctacctc gccttctact   4320
ttatcgccgg cggtctcgcc gatccccacg tcgaccctt  taactcggac ggccacgtcg   4380
cgcgcatcat cttcaacatc ctccgctacg tctgcgtcct gctgatctgc acacaattca   4440
tcttgtccct cggcaaccgt ccgcagggtg ccaaaagaat gtatctcgca tccatgatca   4500
tctacgccgt catcatggtg tacaccacct tcgccaccat cttcatcgtc gtgcgacaaa   4560
tccaaccctc tcaaaaatcc gacgacaagc ccgacctcga actcggcaac aacgtcttca   4620
ccaacctgat cgtctccgtg gctagtaccc tcgggctcta cttcgtcatg tcctttctct   4680
atctcgaccc ctggcacatg ttcacctcgg ccatccagta ctttgtcctg ctgccttcct   4740
acatctgcac gctccagatc tacgcctttt gcaacaccca cgacgtcaca tggggcacca   4800
aaggcgacaa cgtgatgcgc accgatctcg gaggcgcct  tggcaaggga agcaccgtcg   4860
aactggaaat gccttcggac caactcgaca tcgactcggg atacgacgaa tgtctacgta   4920
atctccgcga tcgcgtcatg gtccctgccg ttcccgtgtc cgaggaccag ctgcagcagg   4980
attactacaa gtcggtgcgc acgtacatgg tggtgtcgtg gatggtggcc aacgcgacgc   5040
tggccatggc ggtctcggaa gcgtatgcg  attcggaaat tggggataat ttttacttgc   5100
ggtttatcct gtgggcggtg gcggcccctgg cgctgtttag agcgttgggg tcgacgacgt   5160
ttgcggcgat taatctggtg agtgctctcg tggagggcag ggtcaggctg aggttgaata   5220
tgaaagggtt taggtggatt aaggagaagt gggggggatgc ggatgtgaag gcaagtttg   5280 aggggttggg ggatcgggcg aggggggttgg cgaggcggtg agctagcaag cttggacacg   5340
ctgaaatcac cagtctctct ctacaaatct atctctctct attttctcca taataatgtg   5400
tgagtagttc ccagataagg gaattagggt tcctataggg tttcgctcat gtgttgagca   5460
```

```
tataagaaac ccttagtatg tatttgtatt tgtaaaatac ttctatcaat aaaatttcta    5520
attcctaaaa ccaaaatcca gtactaaaat ccagatcatg catggtacag cggccaattc    5580
cggggtacgg tcgacggccg agtact                                         5606

<210> SEQ ID NO 14
<211> LENGTH: 6464
<212> TYPE: DNA
<213> ORGANISM: Artificial Sequence
<220> FEATURE:
<223> OTHER INFORMATION: T-DNA of pTDBI50
<220> FEATURE:
<221> NAME/KEY: misc_feature
<222> LOCATION: (1)..(25)
<223> OTHER INFORMATION: LB: Left T-DNA border (synthetic) (complement)
<220> FEATURE:
<221> NAME/KEY: misc_feature
<222> LOCATION: (56)..(316)
<223> OTHER INFORMATION: 3'nos: 3'UTR from nopaline synthase gene of
      T-DNA pTiT37 (complement)
<220> FEATURE:
<221> NAME/KEY: misc_feature
<222> LOCATION: (336)..(887)
<223> OTHER INFORMATION: bar: CDS of phosphinothricin acetyl transferase
      of Streptomyces hygroscopicus (complement)
<220> FEATURE:
<221> NAME/KEY: misc_feature
<222> LOCATION: (888)..(1720)
<223> OTHER INFORMATION: P35S3: promoter region of CaMV 35S transcript
      (complement).
<220> FEATURE:
<221> NAME/KEY: misc_feature
<222> LOCATION: (1766)..(3173)
<223> OTHER INFORMATION: F286: fiber specific promoter region
<220> FEATURE:
<221> NAME/KEY: misc_feature
<222> LOCATION: (3189)..(3250)
<223> OTHER INFORMATION: 5' cab22L: leader sequence of the cab22L gene
      from Petunia
<220> FEATURE:
<221> NAME/KEY: misc_feature
<222> LOCATION: (3255)..(3359)
<223> OTHER INFORMATION: XylT: Golgi targeting signal of the beta 1,2
      xylosyltransferase protein
<220> FEATURE:
<221> NAME/KEY: misc_feature
<222> LOCATION: (3369)..(6203)
<223> OTHER INFORMATION: CHS2: chitin synthase coding region from
      Neurospora crassa
<220> FEATURE:
<221> NAME/KEY: misc_feature
<222> LOCATION: (3369)..(6203)
<223> OTHER INFORMATION: 3' 35S: 3' YTR fragment of the CaMV 35S
      transcript.
<220> FEATURE:
<221> NAME/KEY: misc_feature
<222> LOCATION: (6488)..(6464)
<223> OTHER INFORMATION: RB: Right T-DNA border (synthetic) (complement)

<400> SEQUENCE: 14
cggcaggata tattcaattg taaatggctc catggcgatc gctctagagg atctgcgatc      60
tagtaacata gatgacaccg cgcgcgataa tttatcctag tttgcgcgct atattttgtt    120
ttctatcgcg tattaaatgt ataattgcgg gactctaatc ataaaaaccc atctcataaa    180
taacgtcatg cattacatgt taattattac atgcttaacg taattcaaca gaaattatat    240
gataatcatc gcaagaccgg caacaggatt caatcttaag aaactttatt gccaaatgtt    300
tgaacgatct gcttcggatc ctagaacgcg tgatctcaga tctcggtgac gggcaggacc    360
ggacggggcg gtaccggcag gctgaagtcc agctgccaga aacccacgtc atgccagttc    420
ccgtgcttga agccggccgc ccgcagcatg ccgcggggg catatccgag cgcctcgtgc       480
```

| | |
|---|---|
| atgcgcacgc tcgggtcgtt gggcagcccg atgacagcga ccacgctctt gaagccctgt | 540 |
| gcctccaggg acttcagcag gtgggtgtag agcgtggagc ccagtcccgt ccgctggtgg | 600 |
| cgggggagga cgtacacggt cgactcggcc gtccagtcgt aggcgttgcg tgccttccag | 660 |
| gggcccgcgt aggcgatgcc ggcgacctcg ccgtccacct cggcgacgag ccagggatag | 720 |
| cgctcccgca gacggacgag gtcgtccgtc cactcctgcg gttcctgcgg ctcggtacgg | 780 |
| aagttgaccg tgcttgtctc gatgtagtgg ttgacgatgg tgcagaccgc cggcatgtcc | 840 |
| gcctcggtgg cacggcggat gtcggccggg cgtcgttctg ggtccatggt tatagagaga | 900 |
| gagatagatt tatagagaga gactggtgat tcagcgtgt cctctccaaa tgaaatgaac | 960 |
| ttccttatat agaggaaggg tcttgcgaag gatagtggga ttgtgcgtca tcccttacgt | 1020 |
| cagtggagat gtcacatcaa tccacttgct ttgaagacgt ggttggaacg tcttcttttt | 1080 |
| ccacgatgct cctcgtgggt ggggggtccat ctttgggacc actgtcggca gaggcatctt | 1140 |
| gaatgatagc ctttccttta tcgcaatgat ggcatttgta ggagccacct tccttttcta | 1200 |
| ctgtcctttc gatgaagtga cagatagctg ggcaatggaa tccgaggagg tttcccgaaa | 1260 |
| ttatcctttg ttgaaaagtc tcaatagccc tttggtcttc tgagactgta tctttgacat | 1320 |
| ttttggagta gaccagagtg tcgtgctcca ccatgttgac gaagattttc ttcttgtcat | 1380 |
| tgagtcgtaa aagactctgt atgaactgtt cgccagtctt cacggcgagt tctgttagat | 1440 |
| cctcgatttg aatcttagac tccatgcatg gccttagatt cagtaggaac tacctttta | 1500 |
| gagactccaa tctctattac ttgccttggt ttatgaagca agccttgaat cgtccatact | 1560 |
| ggaatagtac ttctgatctt gagaaatatg tctttctctg tgttcttgat gcaattagtc | 1620 |
| ctgaatcttt tgactgcatc tttaaccttc ttgggaaggt atttgatctc ctggagattg | 1680 |
| ttactcgggt agatcgtctt gatgagacct gctgcgtagg aacgcggccg ctgtacaggg | 1740 |
| cccgggcata tggcgcgccg gtacccaacc tctcgagctg ccatattggg ttttcacta | 1800 |
| cccacctctt cattaaatgt atcttcaacc tctcaactcc tttcaccacc agacgaatct | 1860 |
| tctttagcaa aatcaaaatg accttatgaa aatttagcac gtccacctcc agattcaaag | 1920 |
| gctgtgaatc cccaacttcg gaaattgttc atctccacat tcaagaataa tgagttcctc | 1980 |
| aatttgtttt aactgattag ccgatattaa gcgagttaga ctccatggaa ataaaatcac | 2040 |
| cctaataaat agcaacgctt ttgaacgtct ctaggttcca agcgtgctaa ggagcgccag | 2100 |
| taacttcaat ccaagttgtg cgaaaacgta tgaaatggaa ctgagaccag cgttcaacat | 2160 |
| cgatgaaaat ttgttttaac aatgagaact gcaaatcctc catagtcttc taacatttca | 2220 |
| acattcgaaa tctcgaaaag aaattggctt gatatgattt atttagggtg ttaattttat | 2280 |
| gtattataat aatgcacaaa ttgatatttt atgcatcaca tttaatattt ttaaagtata | 2340 |
| taatatcaaa tcattttatg aaaataaaaa taccaaataa tacataaatt gatagttcaa | 2400 |
| gtatttcatt aaaaattttc aaaatataaa tatcatattg aaacatttta taaaagaata | 2460 |
| gataccaaat atgacatcat ccctgttga gagtaaccaa acactgtttt catccagccc | 2520 |
| atgagaagta tttggcccaa agcaaaagt ttcagtacaa tgaattatga atcccaaaaa | 2580 |
| aaccccaagt ggtccaggtc caagccagtc tagggctgag gaaagaaatg gaaaaattga | 2640 |
| aaagtaattc cagggtctga ttcaatttta ttaaatttag tttgattttg gtttcggttc | 2700 |
| ataaatttaa aaataatttt aaaatgttat ataaaactgt ttttaaaaa taaattaatc | 2760 |
| aataatctaa aacgataaaa atggcgattt gaattaagct catattttga aaaaaaata | 2820 |
| aaaattatct catccagaac tgattaaaac cgaaccgatg aatcctagaa gccaagccaa | 2880 |

```
gtgtgcagag taagaataga acatcaacat tttgctttaa gcttttcgtt gcttgcactc   2940
taagaagcat aaaacgcaag caaaacttga cactagtgtg agtgtgagtg cccatcattc   3000
atcaaccctg aaaatcgccc ttcccctaat cagttctaac ctcactttct aacactttca   3060
ctgcagcact caaaaacatt cgccgaatct ttactataaa ctcccagtgt tggtttctcc   3120
actccaaacc caaaccacga ccaccacatt ttgcttcgta tctttgatat ctagatctcc   3180
cgggagctca tttctctatt acttcagcca taacaaaaga actcttttct cttcttatta   3240
aaccaaaacc atggatgagt aaacggaatc cgaagattct gaagattttt ctgtatatgt   3300
tacttctcaa ctctctcttt ctcatcatct acttcgtttt tcactcatcg tcgtttttcag  3360 ccaaaaccat ggagtccaga atcagcaacc ggttatcgag ttccgccaca aggacggtac   3420
gagccttcag aaatcgatgt catgccaggc cagggacacc gggatcgagt tacgaaaatg   3480
cgaggcgacc gcttccctcg gcaccagcgc ctttacacta caatagccca agtcgcgcag   3540
cgagtcatta tccacggtac catggaggtt atgcggacga cgtgacagtt agcatgggac   3600
cggacgacga tcgtacagat atctttggcc ccgaaaccga tctcagcgaa acgcgccacc   3660
tcaacgacga atacgggttt cggtcatccc agatcaccct cagcgaagat ccccacggca   3720
cccacgcgcg ttcccggtac gacgacgaag acgatgtgag caccacttat tcctccaaca   3780
cgggcaccag cgcttcaggt gtcgacaagt tcgagcatta cggtcccatt ccggaggaag   3840
gcaagcacga gcggcgcggc gtgcgaccac cacagatgtc gaggaaggaa gtccagctca   3900
tcaacgcgca actcgttctc gagtgcaaga ttccgactat attgtattcg tttttgccca   3960
ggagagacga agtggagttt acgcacatgc ggtacacagc cgtcacttgt gaccctgatg   4020
actttgttgc caggggttac aagttgcgcc agaatatcgg tcgtaccgcc agggagacgg   4080
agctgttcat ctgcgtgacc atgtacaacg aggacgagtt cggattcaca cggactatgc   4140
acgcagtcat gaagaacatt tcgcattttt gttcccgaaa caagagtagg acgtggggag   4200
cggatgggtg gcagaagatt gtggtctgtg tggtttcgga tggacgagag atcattcacc   4260
cccggacctt ggacgccctc gcagccatgg gcgtttacca gcacggtatc gccaagaact   4320
ttgtcaacca gaaggcggtg caggcccacg tttacgagta cacgacacaa gtgtctctgg   4380
acagcgacct caagttcaag ggcgccgaga agggcatcgt gccctgccag atgatttttt   4440
gcttgaagga gaagaaccaa aagaaactca actcgcatag atggttcttc aacgcctttg   4500
gcaaagcctt gaacccgaat gtgtgtatcc tcctagacgt cggcacccgc cccggcggca   4560
caagtctcta ccatctctgg aaagccttcg acacggattc caacgtggcg ggggcctgcg   4620
gggaaatcaa agcgatgaag gggcggtttg cgggaatttt gctcaaccct ctggtggcta   4680
gtcagaactt tgagtacaag atgagcaata ttctggacaa accgttggag tcggtgtttg   4740
ggtacatcac ggtgttgccg ggcgccttgt cggcgtatcg gtaccatgcg ctgcagaacg   4800
atgagacggg ccatgggccg ttgagtcagt atttcaaggg cgagacgctc catgggcagc   4860
acgcggatgt gtttacggcg aacatgtact tggccgagga ccgaattctg tgttgggagt   4920
tggtggccaa gaggggtgag aggtgggtgt tgaagtatgt gaagggggtgt acgggtgaga   4980 cggatgtgcc tgacaccgtc ccggaattcg tctcgcaacg tcgtcgttgg ctcaacggtg   5040
ccttcttcgc cgccgtctac tccctcgtcc actttcgaca aatctggaaa accgaccaca   5100
cctttatgcg caaagccctt ctccacgtcg aattcctcta ccacctcctg caactcctct   5160
tcacctactt ctccctggcc aacttctacc tcgccttcta ctttatcgcc ggcggtctcg   5220
```

-continued

```
ccgatcccca cgtcgaccct tttaactcgg acggccacgt cgcgcgcatc atcttcaaca    5280
tcctccgcta cgtctgcgtc ctgctgatct gcacacaatt catcttgtcc ctcggcaacc    5340
gtccgcaggg tgccaaaaga atgtatctcg catccatgat catctacgcc gtcatcatgg    5400
tgtacaccac cttcgccacc atcttcatcg tcgtgcgaca aatccaaccc tctcaaaaat    5460
ccgacgacaa gcccgacctc gaactcggca acaacgtctt caccaacctg atcgtctccg    5520
tggctagtac cctcgggctc tacttcgtca tgtccttcct ctatctcgac ccctggcaca    5580
tgttcacctc ggccatccag tactttgtcc tgctgccttc ctacatctgc acgctccaga    5640
tctacgcctt ttgcaacacc cacgacgtca catggggcac caaaggcgac aacgtgatgc    5700
gcaccgatct cggaggcgcc attggcaagg gaagcaccgt cgaactggaa atgccttcgg    5760
accaactcga catcgactcg ggatacgacg aatgtctacg taatctccgc gatcgcgtca    5820
tggtccctgc cgttcccgtg tccgaggacc agctgcagca ggattactac aagtcggtgc    5880
gcacgtacat ggtggtgtcg tggatggtgg ccaacgcgac gctggccatg gcggtctcgg    5940
aagcgtatgg cgattcggaa attggggata attttactt gcggtttatc ctgtgggcgg    6000
tggcggccct ggcgctgttt agagcgttgg ggtcgacgac gtttgcggcg attaatctgg    6060
tgagtgctct cgtggagggc agggtcaggc tgaggttgaa tatgaaaggg tttaggtgga    6120
ttaaggagaa gtgggggggat gcggatgtga agggcaagtt tgaggggttg ggggatcggg    6180 cgaggggggtt ggcgaggcgg tgagctagca agcttggaca cgctgaaatc accagtctct    6240
ctctacaaat ctatctctct ctattttctc cataataatg tgtgagtagt cccagataa     6300 gggaattagg gttcctatag ggtttcgctc atgtgttgag catataagaa acccttagta    6360
tgtatttgta tttgtaaaat acttctatca ataaaatttc taattcctaa aaccaaaatc    6420
cagtactaaa atccagatca tgcatggtac agcggccgcg ttct                    6464
```

<210> SEQ ID NO 15
<211> LENGTH: 982
<212> TYPE: PRT
<213> ORGANISM: Artificial Sequence
<220> FEATURE:
<223> OTHER INFORMATION: Chitin synthase operably linked to XylT Golgi
      targeting signal

<400> SEQUENCE: 15

```
Met Ser Lys Arg Asn Pro Lys Ile Leu Lys Ile Phe Leu Tyr Met Leu
1               5                   10                  15

Leu Leu Asn Ser Leu Phe Leu Ile Ile Tyr Phe Val Phe His Ser Ser
            20                  25                  30

Ser Phe Ser Ala Lys Thr Met Glu Ser Arg Ile Ser Asn Arg Leu Ser
        35                  40                  45

Ser Ser Ala Thr Arg Thr Val Arg Ala Phe Arg Asn Arg Cys His Ala
    50                  55                  60

Arg Pro Gly Thr Pro Gly Ser Ser Tyr Gly Asn Ala Arg Arg Pro Leu
65                  70                  75                  80

Pro Ser Ala Pro Ala Pro Leu His Tyr Asn Ser Pro Ser Arg Ala Ala
                85                  90                  95

Ser His Tyr Pro Arg Tyr His Gly Gly Tyr Ala Asp Asp Val Thr Val
            100                 105                 110

Ser Met Gly Pro Asp Asp Arg Thr Asp Ile Phe Gly Pro Glu Thr
        115                 120                 125

Asp Leu Ser Glu Thr Arg His Leu Asn Asp Ala Tyr Gly Phe Arg Ser
    130                 135                 140
```

-continued

```
Ser Gln Ile Thr Leu Ser Glu Asp Pro His Gly Thr His Ala Arg Ser
145                 150                 155                 160

Arg Tyr Asp Asp Glu Asp Val Ser Thr Thr Tyr Ser Ser Asn Thr
            165                 170                 175

Gly Thr Ser Ala Ser Gly Val Asp Lys Phe Glu His Tyr Gly Pro Ile
            180                 185                 190

Pro Glu Glu Gly Lys His Glu Arg Arg Gly Val Arg Pro Pro Gln Met
            195                 200                 205

Ser Arg Lys Glu Val Gln Leu Ile Asn Gly Glu Leu Val Leu Glu Cys
210                 215                 220

Lys Ile Pro Thr Ile Leu Tyr Ser Phe Leu Pro Arg Arg Asp Glu Val
225                 230                 235                 240

Glu Phe Thr His Met Arg Tyr Thr Ala Val Thr Cys Asp Pro Asp Asp
                245                 250                 255

Phe Val Ala Arg Gly Tyr Lys Leu Arg Gln Asn Ile Gly Arg Thr Ala
                260                 265                 270

Arg Glu Thr Glu Leu Phe Ile Cys Val Thr Met Tyr Asn Glu Asp Glu
            275                 280                 285

Phe Gly Phe Thr Arg Thr Met His Ala Val Met Lys Asn Ile Ser His
290                 295                 300

Phe Cys Ser Arg Asn Lys Ser Arg Thr Trp Gly Ala Asp Gly Trp Gln
305                 310                 315                 320

Lys Ile Val Val Cys Val Val Ser Asp Gly Arg Glu Ile Ile His Pro
                325                 330                 335

Arg Thr Leu Asp Ala Leu Ala Ala Met Gly Val Tyr Gln His Gly Ile
            340                 345                 350

Ala Lys Asn Phe Val Asn Gln Lys Ala Val Gln Ala His Val Tyr Glu
            355                 360                 365

Tyr Thr Thr Gln Val Ser Leu Asp Ser Asp Leu Lys Phe Lys Gly Ala
            370                 375                 380

Glu Lys Gly Ile Val Pro Cys Gln Met Ile Phe Cys Leu Lys Glu Lys
385                 390                 395                 400

Asn Gln Lys Lys Leu Asn Ser His Arg Trp Phe Phe Asn Ala Phe Gly
                405                 410                 415

Lys Ala Leu Asn Pro Asn Val Cys Ile Leu Leu Asp Val Gly Thr Arg
            420                 425                 430

Pro Gly Gly Thr Ser Leu Tyr His Leu Trp Lys Ala Phe Asp Thr Asp
            435                 440                 445

Ser Asn Val Ala Gly Ala Cys Gly Glu Ile Lys Ala Met Lys Gly Arg
450                 455                 460

Phe Gly Gly Asn Leu Leu Asn Pro Leu Val Ala Ser Gln Asn Phe Glu
465                 470                 475                 480

Tyr Lys Met Ser Asn Ile Leu Asp Lys Pro Leu Glu Ser Val Phe Gly
                485                 490                 495

Tyr Ile Thr Val Leu Pro Gly Ala Leu Ser Ala Tyr Arg Tyr His Ala
            500                 505                 510

Leu Gln Asn Asp Glu Thr Gly His Gly Pro Leu Ser Gln Tyr Phe Lys
            515                 520                 525

Gly Glu Thr Leu His Gly Gln His Ala Asp Val Phe Thr Ala Asn Met
            530                 535                 540

Tyr Leu Ala Glu Asp Arg Ile Leu Cys Trp Glu Leu Val Ala Lys Arg
545                 550                 555                 560
```

```
Gly Glu Arg Trp Val Leu Lys Tyr Val Lys Gly Cys Thr Gly Glu Thr
                565                 570                 575

Asp Val Pro Asp Thr Val Pro Glu Phe Val Ser Gln Arg Arg Arg Trp
                580                 585                 590

Leu Asn Gly Ala Phe Phe Ala Ala Val Tyr Ser Leu Val His Phe Arg
                595                 600                 605

Gln Ile Trp Lys Thr Asp His Thr Phe Met Arg Lys Ala Leu Leu His
        610                 615                 620

Val Glu Phe Leu Tyr His Leu Leu Gln Leu Leu Phe Thr Tyr Phe Ser
625                 630                 635                 640

Leu Ala Asn Phe Tyr Leu Ala Phe Tyr Phe Ile Ala Gly Gly Leu Ala
                645                 650                 655

Asp Pro His Val Asp Pro Phe Asn Ser Asp Gly His Val Ala Arg Ile
                660                 665                 670

Ile Phe Asn Ile Leu Arg Tyr Val Cys Val Leu Leu Ile Cys Thr Gln
                675                 680                 685

Phe Ile Leu Ser Leu Gly Asn Arg Pro Gln Gly Ala Lys Arg Met Tyr
        690                 695                 700

Leu Ala Ser Met Ile Ile Tyr Ala Val Ile Met Val Tyr Thr Thr Phe
705                 710                 715                 720

Ala Thr Ile Phe Ile Val Val Arg Gln Ile Gln Pro Ser Gln Lys Ser
                725                 730                 735

Asp Asp Lys Pro Asp Leu Glu Leu Gly Asn Asn Val Phe Thr Asn Leu
                740                 745                 750

Ile Val Ser Val Ala Ser Thr Leu Gly Leu Tyr Phe Val Met Ser Phe
                755                 760                 765

Leu Tyr Leu Asp Pro Trp His Met Phe Thr Ser Ala Ile Gln Tyr Phe
        770                 775                 780

Val Leu Leu Pro Ser Tyr Ile Cys Thr Leu Gln Ile Tyr Ala Phe Cys
785                 790                 795                 800

Asn Thr His Asp Val Thr Trp Gly Thr Lys Gly Asp Asn Val Met Arg
                805                 810                 815

Thr Asp Leu Gly Gly Ala Ile Gly Lys Gly Ser Thr Val Glu Leu Glu
                820                 825                 830

Met Pro Ser Asp Gln Leu Asp Ile Asp Ser Gly Tyr Asp Glu Cys Leu
                835                 840                 845

Arg Asn Leu Arg Asp Arg Val Met Val Pro Ala Val Pro Val Ser Glu
                850                 855                 860

Asp Gln Leu Gln Gln Asp Tyr Tyr Lys Ser Val Arg Thr Tyr Met Val
865                 870                 875                 880

Val Ser Trp Met Val Ala Asn Ala Thr Leu Ala Met Ala Val Ser Glu
                885                 890                 895

Ala Tyr Gly Asp Ser Glu Ile Gly Asp Asn Phe Tyr Leu Arg Phe Ile
                900                 905                 910

Leu Trp Ala Val Ala Leu Ala Leu Phe Arg Ala Leu Gly Ser Thr
                915                 920                 925

Thr Phe Ala Ala Ile Asn Leu Val Ser Ala Leu Val Glu Gly Arg Val
                930                 935                 940

Arg Leu Arg Leu Asn Met Lys Gly Phe Arg Trp Ile Lys Glu Lys Trp
945                 950                 955                 960

Gly Asp Ala Asp Val Lys Gly Lys Phe Glu Gly Leu Gly Asp Arg Ala
                965                 970                 975

Arg Gly Leu Ala Arg Arg
```

-continued

```
                980
```

<210> SEQ ID NO 16
<211> LENGTH: 413
<212> TYPE: PRT
<213> ORGANISM: Rhizobium sp.

<400> SEQUENCE: 16

```
Met Asp Leu Leu Gly Thr Thr Gly Ala Val Ala Ile Ser Leu Tyr Ala
1               5                   10                  15

Ala Leu Ser Thr Ala Tyr Lys Gly Met Gln Ala Ile Tyr Ala Leu Pro
            20                  25                  30

Thr Asn Thr Thr Ala Ala Ser Thr Pro Val Thr Gly Ser Gly Ala Pro
        35                  40                  45

Pro Ser Val Asp Val Ile Val Pro Cys Tyr Asn Glu Asp Pro Arg Ala
    50                  55                  60

Leu Ser Ala Cys Leu Ala Ser Ile Ala Lys Gln Asp Tyr Ala Gly Glu
65                  70                  75                  80

Leu Arg Val Tyr Val Val Asp Asp Gly Ser Gly Asn Arg Asn Ala Ile
                85                  90                  95

Ile Pro Val His Asp His Tyr Ala Cys Asp Pro Arg Phe Arg Phe Ile
            100                 105                 110

Leu Met Pro Lys Asn Val Gly Lys Arg Lys Ala Gln Ile Val Ala Ile
        115                 120                 125

Arg Glu Ser Ser Gly Asp Leu Val Leu Asn Val Asp Ser Asp Thr Thr
    130                 135                 140

Ile Ala Pro Asp Val Val Thr Lys Leu Ala Leu Lys Met Tyr Ser Pro
145                 150                 155                 160

Ala Val Gly Ala Ala Met Gly Gln Leu Thr Ala Ser Asn Arg Ser Asp
                165                 170                 175

Thr Trp Leu Thr Arg Leu Ile Asp Met Glu Tyr Trp Leu Ala Cys Asn
            180                 185                 190

Glu Glu Arg Ala Ala Gln Ala Arg Phe Gly Ala Val Met Cys Cys Cys
        195                 200                 205

Gly Pro Cys Ala Met Tyr Arg Arg Ser Ala Leu Leu Leu Leu Leu Asp
    210                 215                 220

Lys Tyr Glu Thr Gln Leu Phe Arg Gly Arg Pro Ser Asp Phe Gly Glu
225                 230                 235                 240

Asp Arg His Leu Thr Ile Leu Met Leu Asn Ala Gly Phe Arg Thr Glu
                245                 250                 255

Tyr Val Pro Glu Ala Ile Ala Ala Thr Val Val Pro Asn Ser Met Gly
            260                 265                 270

Ala Tyr Leu Arg Gln Gln Leu Arg Trp Ala Arg Ser Thr Phe Arg Asp
        275                 280                 285

Thr Leu Leu Ala Leu Arg Leu Leu Pro Gly Leu Asp Arg Tyr Leu Thr
    290                 295                 300

Leu Asp Val Ile Gly Gln Asn Leu Gly Pro Leu Leu Ala Leu Ser
305                 310                 315                 320

Val Leu Thr Gly Leu Ala Gln Leu Ala Leu Thr Ala Thr Val Pro Trp
                325                 330                 335

Ser Thr Ile Leu Met Ile Ala Ser Met Thr Met Val Arg Cys Gly Val
            340                 345                 350

Ala Ala Phe Arg Ala Arg Glu Leu Arg Phe Leu Gly Phe Ser Leu His
        355                 360                 365
```

```
Thr Leu Leu Asn Val Ala Leu Leu Pro Leu Lys Ala Tyr Ala Leu
        370                 375                 380

Cys Thr Leu Ser Asn Ser Asp Trp Leu Ser Arg Gly Ser Pro Ala Ala
385                 390                 395                 400

Ala Pro Asn Gly Val Lys Asp Ser Pro Glu Pro His Cys
                405                 410

<210> SEQ ID NO 17
<211> LENGTH: 12
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 17

Pro Xaa Val Asp Val Ile Xaa Pro Xaa Xaa Asn Glu
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Conserved residues between different NODC
      proteins
<220> FEATURE:
<221> NAME/KEY: misc_feature
<222> LOCATION: (6)..(6)
<223> OTHER INFORMATION: Xaa can be any naturally occurring amino acid

<400> SEQUENCE: 18

Val Asp Asp Gly Ser Xaa Asn
1               5

<210> SEQ ID NO 19
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid

<400> SEQUENCE: 19

Gly Asp Xaa Xaa Leu Asp Val Asp Ser Asp Thr Xaa Xaa Xaa Xaa Asp
1               5                   10                  15

Val

<210> SEQ ID NO 20
<211> LENGTH: 6
<212> TYPE: PRT
```

```
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(3)
<223> OTHER INFORMATION: Xaa can be any naturally occurring amino acid

<400> SEQUENCE: 20

Gly Xaa Xaa Met Gly Gln
1               5

<210> SEQ ID NO 21
<211> LENGTH: 32
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 21

Asp Met Glu Tyr Trp Leu Ala Cys Asn Glu Glu Arg Xaa Xaa Gln Xaa
1               5                   10                  15

Arg Phe Gly Xaa Val Met Xaa Cys Xaa Gly Xaa Cys Xaa Met Tyr Arg
            20                  25                  30

<210> SEQ ID NO 22
<211> LENGTH: 16
<212> TYPE: PRT
<213> ORGANISM: Artificial Sequence
<220> FEATURE:
<223> OTHER INFORMATION: Conserved residues between different NODC
      proteins
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
```

```
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 22

Phe Arg Thr Xaa Tyr Xaa Pro Xaa Ala Xaa Ala Xaa Thr Xaa Val Pro
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: Conserved residues between the different NODC
      proteins
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 23

Tyr Leu Xaa Gln Gln Leu Arg Trp Ala Arg Ser Thr Xaa Arg Xaa Thr
1               5                   10                  15

Xaa Leu

<210> SEQ ID NO 24
<211> LENGTH: 8
<212> TYPE: PRT
<213> ORGANISM: Artificial Sequence
<220> FEATURE:
<223> OTHER INFORMATION: Conserved residues between the different NODC
      proteins
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 24

Gln Asn Xaa Gly Xaa Xaa Leu Leu
1               5

<210> SEQ ID NO 25
<211> LENGTH: 26
<212> TYPE: PRT
<213> ORGANISM: Artificial Sequence
<220> FEATURE:
<223> OTHER INFORMATION: Conserved residues between different NODC
      proteins
```

```
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 25

Arg Phe Xaa Phe Xaa Xaa Xaa His Xaa Xaa Xaa Asn Xaa Xaa Xaa Leu
1               5                   10                  15

Xaa Pro Leu Lys Xaa Tyr Ala Leu Xaa Thr
            20                  25

<210> SEQ ID NO 26
<211> LENGTH: 40
<212> TYPE: PRT
<213> ORGANISM: Artificial Sequence
<220> FEATURE:
<223> OTHER INFORMATION: Conserved residues between different NODC
      proteins
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 26

Trp Leu Thr Arg Leu Ile Asp Met Glu Tyr Trp Leu Ala Cys Asn Glu
1               5                   10                  15

Glu Arg Xaa Xaa Gln Xaa Arg Phe Gly Xaa Val Met Cys Cys Cys Gly
            20                  25                  30

Pro Cys Ala Met Tyr Arg Arg Ser
        35                  40

<210> SEQ ID NO 27
<211> LENGTH: 47
<212> TYPE: PRT
<213> ORGANISM: Artificial Sequence
<220> FEATURE:
<223> OTHER INFORMATION: Conserved residues between different NODC
      proteins
```

```
-continued

<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 27

Leu Leu Xaa Xaa Tyr Glu Xaa Gln Xaa Phe Xaa Gly Xaa Pro Ser Xaa
1               5                   10                  15

Phe Gly Glu Asp Arg His Leu Thr Ile Leu Met Leu Xaa Ala Gly Phe
            20                  25                  30

Arg Thr Xaa Tyr Val Pro Xaa Ala Xaa Ala Xaa Thr Xaa Val Pro
        35                  40                  45

<210> SEQ ID NO 28
<211> LENGTH: 19
<212> TYPE: PRT
<213> ORGANISM: Artificial Sequence
<220> FEATURE:
<223> OTHER INFORMATION: Conserved residues between different NODC
      proteins
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
```

```
<400> SEQUENCE: 28

Tyr Leu Arg Gln Gln Leu Arg Trp Ala Arg Ser Thr Xaa Arg Asp Thr
1               5                   10                  15

Xaa Leu Ala

<210> SEQ ID NO 29
<211> LENGTH: 5
<212> TYPE: PRT
<213> ORGANISM: Artificial Sequence
<220> FEATURE:
<223> OTHER INFORMATION: Arabidopsis DAGAT1 protein

<400> SEQUENCE: 29

Tyr Tyr His Asp Leu
1               5

<210> SEQ ID NO 30
<211> LENGTH: 5
<212> TYPE: PRT
<213> ORGANISM: Artificial Sequence
<220> FEATURE:
<223> OTHER INFORMATION: Arabidopsis DAGAT2 protein

<400> SEQUENCE: 30

Leu Lys Leu Glu Ile
1               5
```